US007807877B2

(12) United States Patent
Brugliera et al.

(10) Patent No.: US 7,807,877 B2
(45) Date of Patent: Oct. 5, 2010

(54) GENETIC SEQUENCES HAVING METHYLTRANSFERASE ACTIVITY AND USES THEREFOR

(75) Inventors: Filippa Brugliera, Preston (AU); Linda Demelis, Bundoora (AU); Ronald Koes, Amsterdam (NL); Yoshikazu Tanaka, Shiga (JP)

(73) Assignee: International Flower Developments Pty. Ltd., Victoria (AU)

( * ) Notice: Subject to any disclaimer, the term of this patent is extended or adjusted under 35 U.S.C. 154(b) by 733 days.

(21) Appl. No.: 10/502,515

(22) PCT Filed: Jan. 24, 2003

(86) PCT No.: PCT/AU03/00079

§ 371 (c)(1),
(2), (4) Date: May 27, 2005

(87) PCT Pub. No.: WO03/062428

PCT Pub. Date: Jul. 31, 2003

(65) Prior Publication Data

US 2007/0150984 A1 Jun. 28, 2007

(30) Foreign Application Priority Data

Jan. 25, 2002 (AU) .................................. PS0174

(51) Int. Cl.
C12N 15/29 (2006.01)
C12N 15/82 (2006.01)
A01H 5/00 (2006.01)
A01H 5/10 (2006.01)

(52) U.S. Cl. ................ 800/298; 800/323; 536/23.1; 536/23.6; 435/320.1

(58) Field of Classification Search .................. None
See application file for complete search history.

(56) References Cited

U.S. PATENT DOCUMENTS 5,034,323 A * 7/1991 Jorgensen et al. ........... 800/282

FOREIGN PATENT DOCUMENTS

WO  WO 01/34817 A2  5/2001
WO  WO 01/73090 A2  10/2001

OTHER PUBLICATIONS

Christensen et al. A flavonoid 7-O-methyltransferase is expressed in barley leaves in response to pathogen attack. (1998) PMB, vol. 36, pp. 219-227.*
Wells (Biochemistry 29:8509-8517, 1990).*
Ngo et al., (The Protein Folding Problem and Tertiary Structure Prediction, K. Merz., and S. Le Grand (eds.) pp. 492-495,1994).*
Keskin et al. (Protein Science, 13:1043-1055, 2004).*
Thornton et al. (Nature structural Biology, structural genomics supplement, Nov. 2000).*

Guo et al. (PNAS, 101: 9205-9210, 2004).*
Maniatis et al. (Molecular Cloning: A Laboratory Manual, Cold Spring Harbor Laboratory, 1982).*
Joshi et al. (Plant Molecular Biology, 37:663-674, 1998, Applicant's IDS).*
Gauthier et al. (GenBank Sequence Accession No. U16794, pp. 1-2, published Nov. 8, 1995).*
Jonsson et al. (Planta, 160:174-179, 1984).*
Pommerrenig et al., 2006, NCBI Accession No. AM159091.*
Bowie et al, Science 247:1306-1310, 1990.*
McConnell et al, Nature 411 (6838):709-713, 2001.*
Fourgoux-Nicol et al (1999, Plant Molecular Biology 40 :857-872).*
Gauthier et al. (GenBank Sequence Accession No. U16794, pp. 1-2, published Nov. 8, 1995).*
Joshi et al. (Plant Molecular Biology, 37:663-674, 1998).*
UniProt Database Accession No. P93711, (1998), Kawai S. et al., XP-002406602.
Joshi C.P. et al., "Conserved Sequence Motifs in Plant S-Adenosyl-L-Methionine-Dependent Methyltransferases", *Plant Molecular Biology* 37:663-674 (1998), XP-002988491.
Holton T.A., "Genetics and Biochemistry of Anthocyanin Biosynthesis", *The Plant Cell* 7(7):1071-1083 (1995), XP-002406599.
UniProt Database Accession No. Q43095, (1998), Meng H. et al., XP-002418608.
Geneseq Database Accession No. AAY05676, (1999), Helentjaris TG et al., XP-002418609.
GenPept Accession No. AAG52015, (2001), Lin, X. et al.
GenPept Accession No. CAC40584, (2001), Jaris, H.
GenPept Accession No. AAC26191, (1998), De Melis, L. E. et al.

(Continued)

*Primary Examiner*—Stuart F. Baum
(74) *Attorney, Agent, or Firm*—Scully, Scott, Murphy & Presser, P.C.

(57) ABSTRACT

The present invention relates generally to a genetic sequence encoding a polypeptide having methyltransferase activity and the use of the genetic sequence and/or the polypeptide to modify one or more phenotypic characteristics of a plant. More particularly, the methyltransferase of the present invention acts on flavonoids, preferably wherein the flavonoid is an anthocyanin. Even more particularly, the present invention relates to a polypeptide having S-adenosyl-L-methionine:anthocyanin 3'-O-methyl-transferase or S-adenosyl-L-methionine:anthocyanin 3',5'-O-methyltransferase activity. The present invention still further provides a genetic sequence encoding a polypeptide having methyltransferase activity derived from *Petunia*, *Torenia Fuchsia* or *Plumbago* or botanically related plants. The instant invention further relates to antisense and sense molecules corresponding to all or part of the subject genetic sequence as well as genetically modified plants as well as cut flowers, parts, extracts and reproductive tissue from such plants.

22 Claims, 31 Drawing Sheets

OTHER PUBLICATIONS

Jonsson L. M. V. et al., "Methylation of Anthocyanins By Cell-Free Extracts of Flower Buds of *Petunia hybrida*", *Phytochemistry* 21(10): 2457-2459 (1982).

Jonsson L. M. V. et al., "Genetic control of anthocyanin-*O*-methyltransferase activity in flowers of *Petunia hybrida*", *Theor Appl Genet 66:* 349-355 (1983).

Gauthier A. et al., "Characterization of Two cDNA Clones Which Encode *O*-Methyltransferases for the Methylation of both Flavonoid and Phenylpropanoid Compounds", *Archives of Biochemistry and Biophysics 351*(2): 243-249 (1998).

Ibrahim R. K. et al., "Plant *O*-methyltransferases: molecular analysis, common signature and classification", *Plant Molecular Biology 36:* 1-10 (1998).

Partial European Search Report, dated Jul. 30, 2009 issued in respect to corresponding European Patent Application No. EP 09 00 4548.

* cited by examiner

Replicon: pBluescript SKII vector 2.95kb

Insert: *difE* cDNA ~0.9kb from *P. hybrida* cv. V26

Replicon: pBluescript SK II (+)vector 2.95kb

Insert: *E20* cDNA ~0.9kb from *P. hybrida* cv. OGB

Replicon: pBluescript SK II (+)vector 2.95kb

Insert: *E33* cDNA ~0.9kb from *P. hybrida* cv. OGB

Replicon: pQE30 3.4kb

Insert: mutE20 cDNA ~0.7kb from P. hybrida cv. OGB

Replicon: pWTT2132 SmaI ~20.7kb

Insert: ~2.8kb Bgl II (blunted) fragment from pCGP1910

Replicon: pWTT2132 SmaI ~20.7kb

Insert: ~2.8kb Bgl II (blunted) fragment from pCGP1911

Replicon: pBluescript SK II (+)vector 2.95kb

Insert: *TFMT* cDNA ~1kb from *Torenia hybrida* cv. Summerwave

Replicon: pQE30 3.4kb

Insert: mut-*TFMT* cDNA ~0.7kb from *Torenia hybrida* cv. Summerwave

Replicon: pRTppoptc XbaI (blunted)/EcoRI 3.3kb

Insert: ~1.0kb Asp718 (blunted)/EcoRI fragment from pTMT5

Replicon: pCGP1988 PstI ~18.6kb

Insert: ~1.7kb PstI fragment from pCGP3097

Replicon: pWTT2132 ~18.7kb

Insert: Multi-cloning region from pNEB193

Replicon: pCGP3099 SmaI ~20.2kb

Insert: ~2.4kb PstI(blunted) fragment from pCGP2092

Replicon: pRTppoptc XbaI (blunted)/EcoRI ~3.3kb

Insert: ~1.8kb Asp718 (blunted)/EcoRI fragment from pCGP1961

Replicon: pSPB1531 AscI ~14.3kb

Insert: ~3.1kb AscI fragment from pSPB580

Replicon: pUCAPAsc BamHI/EcoRI ~2.7kb

Insert: e35S 5': Viola F3'5'H cDNA : petD8 3' ~3.1kb

Replicon: pSPB176 BamHI/SalI fragment ~13.5kb

Insert: Petunia FMT cDNA BamHI/XhoI fragment (derived from pCGP1907)~0.9kb

Replicon: pSPB1530 AscI ~14.3kb

Insert: ~3.1kb AscI fragment from pSPB580

Replicon: pSPB176 BamHI/SalI fragment ~13.4kb

Insert: Torenia FMT cDNA BamHI/XhoI fragment (derived from pTMT5)~0.9kb

Replicon: pBINPLUS HindIII/EcoRI ~12.4kb

Insert: HindIII/EcoRI fragment (derived from pBE2113-ΔGUS)~2.8kb

Replicon: pCR 2.1 3.9kb

Insert: *Fuchsia FMT* 3'RACE ~0.8kb fragment

Replicon: pCR 2.1 3.9kb

Insert: *Fuchsia FMT* full cDNA ~1.0kb

Replicon: pRTppoptc XbaI (blunted)/EcoRI 3.3kb

Insert: ~1.0kb SpeI (blunted)/EcoRI fragment from pCGP3289

Replicon: pCGP3254 PstI ~20.9kb

Replicon: pCGP2788 PstI ~20.9kb

Insert: ~1.7kb PstI fragment from pCGP3290

GENETIC SEQUENCES HAVING METHYLTRANSFERASE ACTIVITY AND USES THEREFOR

BACKGROUND OF THE INVENTION

1. Field of the Invention

The present invention relates generally to a genetic sequence encoding a polypeptide having methyltransferase activity and the use of the genetic sequence and/or the polypeptide to modify one or more phenotypic characteristics of a plant. More particularly, the methyltransferase of the present invention acts on flavonoids, preferably wherein the flavonoid is an anthocyanin. Even more particularly, the present invention relates to a polypeptide having S-adenosyl-L-methionine:anthocyanin 3'-O-methyltransferase or S-adenosyl-L-methionine:anthocyanin 3',5'-O-methyltransferase activity. The present invention still further provides a genetic sequence encoding a polypeptide having methyltransferase activity derived from *Petunia, Torenia, Fuchsia* or *Plumbago* or botanically related plants. The instant invention further relates to antisense and sense molecules corresponding to all or part of the subject genetic sequence as well as genetically modified plants as well as cut flowers, parts, extracts and reproductive tissue from such plants.

2. Description of the Prior Art

Bibliographic details of the publications referred to by author in this specification are collected at the end of the description.

Reference to any prior art in this specification is not, and should not be taken as, an acknowledgment or any form of suggestion that this prior art forms part of the common general knowledge in any country.

The flower or ornamental plant industry strives to develop new and different varieties of flowers and/or plants. An effective way to create such novel varieties is through the manipulation of flower color. Classical breeding techniques have been used with some success to produce a wide range of colors for most of the commercial varieties of flowers and/or plants available today. This approach has been limited, however, by the constraints of a particular species' gene pool and for this reason it is rare for a single species to have the full spectrum of colored varieties. For example, the development of novel colored varieties of plants or plant parts such as flowers, foliage and stems would offer a significant opportunity in both the cut flower and ornamental markets. In the flower or ornamental plant industry, the development of novel colored varieties of major flowering species such as rose, chrysanthemum, tulip, lily, carnation, gerbera, orchid, lisianthus, begonia, torenia, geranium, petunia, nierembergia, pelargonium, impatiens and cyclamen would be of great interest. A more specific example would be the development of a blue rose or gerbera for the cut flower market.

In addition, the development of novel colored varieties of plant parts such as vegetables, fruits and seeds would offer significant opportunities in agriculture. For example, novel colored seeds would be useful as proprietary tags for plants. Furthermore modifications to flavonoids common to berries including grapes and their juices including wine have the potential to impart altered style characteristics of value to such fruit and byproduct industries.

Flower color is predominantly due to three types of pigment: flavonoids, carotenoids and betalains. Of the three, the flavonoids are the most common and contribute a range of colors from yellow to red to blue. The flavonoid molecules that make the major contribution to flower color are the anthocyanins, which are glycosylated derivatives of cyanidin and its methylated derivative peonidin, delphinidin and its methylated derivatives petunidin and malvidin and pelargonidin. Anthocyanins are localised in the vacuole of the epidermal cells of petals or vacuole of sub epidermal cells of leaves.

The flavonoid pigments are secondary metabolites of the phenylpropanoid pathway. The biosynthetic pathway for the flavonoid pigments (flavonoid pathway) is well established, (Holton and Cornish, *Plant Cell* 7: 1071-1083, 1995; Mol et al., *Trends Plant Sci.* 3: 212-217, 1998; Winkel-Shirley, *Plant Physiol.* 126: 485-493, 2001a and Winkel-Shirley, *Plant Physiol.* 127: 1399-1404, 2001b) and is shown in FIGS. 1A and B. Three reactions and enzymes are involved in the conversion of phenylalanine to p-coumaryl-CoA, one of the first key substrates in the flavonoid pathway. The enzymes are phenylalanine ammonia-lyase (PAL), cinnamate 4-hydroxylase (C4H) and 4-coumarate:CoA ligase (4CL). The first committed step in the pathway involves the condensation of three molecules of malonyl-CoA (provided by the action of acetyl CoA carboxylase (ACC) on acetyl CoA and $CO_2$) with one molecule of p-coumaryl-CoA. This reaction is catalysed by the enzyme chalcone synthase (CHS). The product of this reaction, 2',4,4',6', tetrahydroxy-chalcone, is normally rapidly isomerized by the enzyme chalcone flavanone isomerase (CHI) to produce naringenin. Naringenin is subsequently hydroxylated at the 3 position of the central ring by flavanone 3-hydroxylase (F3H) to produce dihydrokaempferol (DHK).

The B-ring of DHK can be hydroxylated at either the 3', or both the 3' and 5' positions, to produce dihydroquercetin (DHQ) and dihydromyricetin (DHM), respectively. The pattern of hydroxylation of the B-ring plays a key role in determining petal color, with DHK generally leading to the production of the brick red pelargonidin-based pigments, DHQ generally leading to the red/pink cyanidin-based pigments and DHM generally leading to the blue/violet delphinidin-based pigments.

The dihydroflavonols (DHK, DHQ and DHM) can also be acted upon by flavonol synthase to produce the flavonols kaempferol, quercetin and myricetin. The flavonols are colorless but act as copigments with the anthocyanins to enhance flower color.

The next step in the pathway, leading to the production of the colored anthocyanins from the dihydroflavonols, involves dihydroflavonol 4-reductase (DFR) with the production of the leucoanthocyanidins. These flavonoid molecules are unstable under normal physiological conditions and glycosylation at the 3-position, through the action of glycosyltransferases, stabilizes the anthocyanidin molecule thus allowing accumulation of the anthocyanins. In general, the glycosyltransferases transfer the sugar moieties from UDP sugars and show high specificities for the position of glycosylation and relatively low specificities for the acceptor substrates (Seitz and Hinderer, Anthocyanins. In: *Cell Culture and Somatic Cell Genetics of Plants*. Constabel, F. and Vasil, I. K. (eds.), Academic Press, New York, USA, 5: 49-76, 1988). Anthocyanins can occur as 3-monosides, 3-biosides and 3-triosides as well as 3,5-diglycosides and 3,7-diglycosides associated with the sugars glucose, galactose, rhamnose, arabinose and xylose (Strack and Wray, In: *The Flavonoids—Advances in Research since* 1986. Harborne, J. B. (ed), Chapman and Hall, London, UK, 1-22, 1993).

Glycosyltransferases involved in the stabilization of the anthocyanidin molecule include UDP glucose:flavonoid 3-glucosyltransferase (3GT), which transfers a glucose moiety from UDP glucose to the 3-O-position of the anthocyanidin molecule to produce anthocyanidin 3-O-glucoside.

In petunia and pansy (amongst others), these anthocyanins can then be glycosylated by another glycosyltransferase, UDP rhamnose:anthocyanidin 3-glucoside rhamnosyltransferase (3RT), which adds a rhamnose group to the 3-O-bound glucose of the anthocyanin molecule to produce the anthocyanidin 3-rutinosides, and once acylated, can be further modified by UDP: glucose anthocyanin 5 glucosyltransferase (5GT).

Many anthocyanidin glycosides exist in the form of polyacylated derivatives. Acylation may be important for uptake of anthocyanins into the vacuoles as was demonstrated by Hopp and Seitz (*Planta* 170: 74-85, 1987). The acyl groups that modify the anthocyanidin glycosides can be divided into two major classes based upon their structure. The aliphatic acyl groups include malonic acid or succinic acid and the aromatic class includes the hydroxy cinnamic acids such as p-coumaric acid, caffeic acid and ferulic acid and the benzoic acids such as p-hydroxybenzoic acid.

Acylation of the anthocyanidin 3-rutinosides with either p-coumaric acid or caffeic acid (Griesbach et al., *Phytochemistry* 30: 1729-1731, 1991) occurs in *Petunia hybrida*. In other plant systems, acylation of flavonoids by aliphatic acids, such as malonic acid, succinic acid and acetic acid also occur (Goto, *Tetrahedron* 27: 2413-2416, 1987; Stafford, *Flavonoid Metabolism*. CRC Press, Inc. Boca Raton, Fla., USA, 1990).

Methylation at the 3' and 3', 5' positions of the B-ring of anthocyanidin 3-(p-coumaryl)rutinoside-5-glucosides occurs in petunia. It has been demonstrated in cell-free extract of flower buds of *P. hybrida* that S-adenosyl-L-methionine is the methyl donor and O-methyltransferase acts on anthocyanidin 3(p-coumaryl)rutinoside-5-glucoside. Under the conditions used, no methylating activity was detected when anthocyanidins, anthocyanidin 3-glucosides, anthocyanidin 3-rutinosides, caffeic acid or p-coumaric acid were used as substrates (Jonsson et al., *Phytochemistry* 21(10): 2457-2460, 1982).

Methylation of the B ring of anthocyanins is controlled by the Mt1, Mt2, Mf1 and Mf2 loci in petunia (Jonsson et al., *Theor. Appl. Genet.* 68: 459-466, 1984b). The four enzymes thought to be encoded by each gene have been described. They catalyze both 3' and 5' O-methylation of the B ring. The 3'5' methylation activity is more pronounced with the Mf1 and Mf2 encoded enzymes (Jonsson et al., 1984b, supra).

The Mt loci were thought to encode S-adenosyl-L-methionine:anthocyanin 3'-O-methyltransferase (3'FMT) and the Mf loci to encode S-adenosyl-L-methionine:anthocyanin 3',5'-O-methyltransferase activity (3'5'FMT) and that the enzymes only methylate the anthocyanin 3-(p-coumaryl)rutinoside-5-glucoside. (Jonsson et al., 1982 supra; Jonsson et al., *Planta* 160: 174-179, 1984a; Jonsson et al., 1984b, supra). It was originally thought that the genes Mf1 and Mf2 could only express themselves if at least one of the genes Mt1 or Mt2 is represented by its dominant allele. However, biochemical studies have since contradicted these findings by showing that both enzymes were capable of methylating delphinidin 3-(p-coumaryl)-rutinoside-5-glucosides to the corresponding malvidin pigment in in vitro assays (Jonsson et al., *Theor. Appl. Genet.* 66: 349-355, 1983). Furthermore, the action of Mf1 and Mf2 was thought to be restricted to the corolla limb (Wiering, *Hort. Genen. Phaenen.* 17: 117-134, 1974).

The presence of methylated anthocyanin pigments have been reported in *Petunia* sp. (Sink (ed), *Petunia*, Springer-Verlag, Berlin, 1984; Ando et al., *Biochemical systematics and ecology*, 27: 623-650, 1999), *Plumbago* sp. (inter alia, Harborne, *Phytochemistry*, 6: 1415-1428, 1967; Harborne, *Arch Biochem Biophys*, 96: 171-178, 1962), *Vitis* sp. (Cachio et al., *American J of Ecology and Viticulture*, 43: 244-248, 1992), *Babiana stricta* (Toki et al., *Phytochemistry*, 37: 885-88-7, 1994), *Pinus* sp. (Andersen, *Biochemical systematics and ecology*, 20: 145-148, 1992), *Picea* sp., *Larix* sp., *Phaseolus* sp. (Hungria et al., *Plant Physiology*, 97: 751-758, 1991; Takeoka et al., *Journal of Agricultural and Food Chemistry*, 45: 3395-3400, 1997), *Solanum* sp. (Lewis et al., *J. of the Science of Food and Agriculture*, 77: 45-57, 1998), *Vaccinium* sp. (Ballington et al., *Can. J. of Plant Sci.*, 68: 241-246, 1988; Skrede et al., *J of Food Science*, 65: 357-364, 2000), *Cyclamen* sp. (Webby and Boase, *Phytochemistry*, 52: 939-941, 1999), *Iris* sp. (Yabuya et al., *Euphytica*, 98: 163-167, 1997; Yabuya and Noda, *Euphytica*, 103: 325-328, 1998), *Pelargonium* sp. (Mitchell et al., *Phytochemistry*, 47: 355-361, 1998; Kobayashi et al., *Breeding Science*, 48: 169-176, 1998), *Geranium* sp. (Andersen et al., *Phytochemistry*, 38: 1513-1517, 1995), *Pisum* sp. (Crowden, *Phytochemistry*, 21: 2989-2990, 1982), *Lathyrus* sp. (Rat'kin et al., *Zh Obshch Biol*, 41: 685-699, 1980), *Clitoria* sp (Srivastava and Pande, *Planta Med*, 32: 138-140, 1977), *Catharanthus* sp. (Carew and Krueger, *Phytochemistry*, 15: 442, 1976), *Malvia* sp. (Takeda et al., *Phytochemistry*, 28: 499-500, 1989), *Mucuna* sp. (Ishikura and Shibata, *Bot Mag (Tokyo)*, 86: 1-4, 1973), *Vicia* sp. (Catalano et al., *J. Agricultural and Food Chemistry*, 49: 4568-4570, 1998; Nozzolillo et al., *Canadian Journal of Botany*, 67: 1600-1604, 1989), *Saintpaulia* sp. (Griesbach, *Phytochemistry*, 48: 829-830, 1998), *Lagerstroemia* sp. (Toki and Katsuyama, *J. Jap Soc Hortic. Sci.*, 63: 853-861, 1995), *Tibouchina* sp. (Francis et al., *J Am Soc Hortic Sci*, 107: 789-791, 1982, Terahara et al., *J. Natural Products*, 56: 335-340, 1993), *Hypocalyptus* sp. (Van Wyk et al., *Biochemical systematics and ecology*, 23: 295-297, 1995), *Rhododendron* sp., *Linum* sp., *Macroptilium* sp. (Imrie and Hutton, *J. Hered.*, 69: 54-56 1978), *Hibiscus* sp. (Kim et al., *Phytochemistry*, 28: 1503-1506, 1989; Kim and Fujieda, *J. Kor. Soc. Hortic. Sci.*, 32: 247-255, 1991), *Hydrangea* sp. (Takeda et al., *Phytochemistry*, 29: 1089-1091, 1990), *Ipomoea* sp. (Saito et al., *Phytochemistry* 41: 1607-1611, 1996), *Cymbidium* sp. (Woltering and Somhorst, *J. Plant Physiol.*, 136: 295-299, 1990), *Millettia* sp. (Parvez and Ogbeide, *Phytochemistry*, 29: 2043-2044, 1990), *Hedysarum* sp. (Chriki and Harborne, *Phytochemistry*, 22: 2322-2323, 1983; Chriki, *Agronomie*, 10: 553-540, 1990), *Lespedeza* sp., *Antigonon* sp. (Tiwari and Minocha, *Vijnana Parishad Anusandhan Patrika*, 23: 305-308, 1980) and *Pisum* sp. (Crowden, *Phytochemistry*, 21: 2989-2990, 1982).

This list describes the species from which methylated anthocyanin pigments have been reported. However, it is expected that these pigments will be present in many other species.

Plant S-adenosyl-L-methionine-dependent O-methyltransferases (SAM-OMTs) are key enzymes in metabolic pathways such as phenylpropanoid and flavonoid synthesis. These enzymes facilitate the transfer of the methyl group of S-adenosyl-L-methionine (SAM) to the hydroxyl group of an acceptor molecule with the formation of its methyl ether derivative and S-adenosyl-L-homocysteine as products. The chemical mechanisms of methyl transfer reactions are identical. However, SAM-OMTs differ in their selectivity with respect to the stereochemistry of the methyl acceptor molecules, as well as the substitution pattern of their phenolic hydroxyl groups. Methylation of different substrates is generally catalysed by distinct SAM-OMTs. However, some enzymes have a broad substrate range although they will usually have a preference for a specific substrate or group of compounds.

Currently, there are over 87 plant-derived sequences encoding SAM-OMTs in the GenBank database. Practically all of these sequences contain three highly conserved consensus motifs (motifs A, B and C) exhibiting a specific spatial arrangement (Joshi and Chiang, *Plant Mol. Biol.* 37: 663-674, 1998; Ibrahim and Muzac, In *Recent advances of phytochemistry*. Evolution of metabolic pathways. Elsevier Science Ltd. 34: 349-385, 2000). Since these motifs are present in most plant SAM-OMTs regardless of substrate specificity, it is thought that they are essential for SAM binding.

By considering the length of the encoded protein and the spatial relationships between motifs A and B and motifs B and C, the plant SAM-OMTs can be grouped into two distinct classes. Group I contains all the CCoAOMTs (caffeoyl-CoA SAM-OMTs) and exhibits a specific spatial arrangement of 19 amino acids between motifs A and B, and 24 amino acids between motifs B and C. Group II contains proteins with a distance of 52 residues between motifs A and B and 30 residues between B and C. Group II SAM-OMTs include COMTs (caffeic acid OMTs), F3'OMT (flavonoid 3'-OMT) (Gauthier et al., *Plant Mol. Biol.* 32: 1163-1169, 1996), IOMTs (isoflavone OMTs) (He and Dixon, *Plant Mol. Biol.* 36: 43-54, 1998), 2'OMTs (isoliquiritigenin 2'-OMT) (Maxwell, *Plant J.* 4(6): 971-981, 1993), IMT (inositol OMT) (Rammesmeyer et al., *Arch. Biochem. Biophys.* 322(1): 183-188, 1995), and F7OMT (flavonoid 7-OMT) (Christensen et al., *Plant Mol. Biol.* 36: 219-227, 1998), among others. It is important to note at this point that those enzymes for which substrate analysis has been undertaken and for which function has been assigned are usually tested with a limited range of substrates. The flavonoid SAM-OMT sequences that have been isolated to date have all been implicated in defense responses with none being shown to have activity on anthocyanins and belong to the Group II SAM-OMTs.

CCoAOMT proteins, or Group I SAM-OMTs, vary in length between 231-248 amino acids and usually require divalent cations, such as $Mg^{2+}$, for catalytic activity. Group II SAM-OMTs are generally around 344-383 amino acids in length and do not require divalent cations. The two groups share approximately 20-30% amino acid identity.

In addition to the above modifications, pH and copigmentation with other flavonoids such as flavonols and flavones can affect petal color. Flavonols and flavones can also be aromatically acylated (Brouillard and Dangles, In: *The Flavonoids—Advances in Research* since 1986. Harborne, J. B. (ed), Chapman and Hall, London, UK, 1-22, 1993).

The ability to control the activity of flavonoid methyltransferases (herein after referred to as "FMT") specifically anthocyanin methyltransferases would provide a means of manipulating petal color thereby enabling a single species to express a broader spectrum of flower colors. Such control may be by modulating the level of production of an indigenous enzyme or by introducing a non-indigenous enzyme.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

In accordance with the present invention, it has been determined that malvidin-based pigments appear "bluer" than delphinidin-based pigments in the same petal background. A class of methyltransferases that act on flavonoids and in particular anthocyanins have been isolated and surprisingly found to belong to the Class I SAM-OMT group instead of the Class II SAM-OMT as may have been predicted from the literature. These are referred to herein as flavonoid methyltransferases (FMT or FMTs). Examples of these novel methyltransferases include, but are not limited to, 3' FMT and 3'5' FMT. These novel FMTs can be derived from many species, for example, *Petunia* sp., *Torenia* sp. *Plumbago* sp. and *Fuchsia* sp.

The present invention provides, therefore, isolated nucleic acid molecules comprising sequences of nucleotides encoding, or complementary to sequences encoding, an FMT or a mutant, derivative, part, fragment, homolog or analog thereof.

The mutants, derivatives, parts, fragments, homologs and analogs may or may not be functional. Preferably, however, they are functional.

The isolated nucleic acid molecules encoding the FMTs of the present invention are proposed to be useful in manipulating the color of plants or plant parts such as flowers, fruits, nuts, roots, stems, leaves and seeds. Genetic modification of plants with the nucleic acid molecules of the present invention further permit altered plants wherein extracts thereof are useful as flavoring or food additives or health products including beverage or juice products. Such beverages include but are not limited to wines, spirits, teas, coffee, milk and dairy products.

Particularly, exemplified nucleic acid molecules are from *Petunia* (SEQ ID NO: 1, SEQ ID NO: 4, SEQ ID NO: 6 and SEQ ID NO: 26), *Torenia* (SEQ ID NO: 11) and *Fuchsia* (SEQ ID NO: 21, SEQ ID NO: 41 and SEQ ID NO: 43). The corresponding amino acid sequences are represented by SEQ ID NO: 2, SEQ ID NO: 5 and SEQ ID NO: 7 (all *Petunia*), SEQ ID NO: 12 (*Torenia*) and SEQ ID NO: 42 and SEQ ID NO: 44 (both *Fuchsia*).

Accordingly, in a preferred embodiment, the present invention provides nucleic acid molecules comprising nucleotide sequences as defined in SEQ ID NO:1 or SEQ ID NO:4 or SEQ BD NO:6 or SEQ ID NO:11 or SEQ ID NO:21 or SEQ ID NO:26 SEQ ID NO:41 or SEQ ID NO:43 or a nucleotide sequence having at least about 50% similarity thereto or capable of hybridizing to one or more of these sequences.

The nucleic acid molecules of the present invention preferably encode an amino acid sequence substantially as set forth in SEQ ID NO:2 or SEQ ID NO:5 or SEQ ID NO:7 or SEQ ID NO:12 or SEQ ID NO:22 or SEQ ID NO:42 or SEQ ID NO:44 or an amino acid sequence having at least about 50% similarity thereto.

The present invention further provides an oligonucleotide of 5-50 nucleotides having substantial similarity or complementarity to a part or region of a molecule with a nucleotide sequence set forth in SEQ ID NO:1 or SEQ BD NO:4 or SEQ ID NO:6 or SEQ ID NO:11 or SEQ ID NO:21 or SEQ ID NO:26 or SEQ ID NO:41 or SEQ ID NO:43 or a complementary form thereof.

A summary of sequence identifiers used throughout the specification is provided in Table 1. A further aspect of the present invention provides a method for producing a transgenic plant capable of synthesizing FMT, said method comprising stably transforming a cell of a suitable plant with a nucleic acid sequence which comprises a sequence of nucleotides encoding said FMT under conditions permitting the eventual expression of said nucleic acid sequence, regenerating a transgenic plant from the cell and growing said transgenic plant for a time and under conditions sufficient to permit the expression of the nucleic acid sequence. The transgenic plant may thereby produce non-indigenous FMT at elevated levels relative to the amount expressed in a comparable non-transgenic plant.

Another aspect of the present invention contemplates a method for producing a transgenic plant with reduced indigenous or existing FMT activity, said method comprising stably transforming a cell of a suitable plant with a nucleic acid molecule which comprises a sequence of nucleotides encoding or complementary to a sequence encoding an FMT activity, regenerating a transgenic plant from the cell and where necessary growing said transgenic plant under conditions sufficient to permit the expression of the nucleic acid.

Yet another aspect of the present invention contemplates a method for producing a genetically modified plant with reduced indigenous or existing FMT activity, said method comprising altering the FMT gene through modification of the indigenous sequences via homologous recombination from an appropriately altered FMT gene or derivative or part thereof introduced into the plant cell, and regenerating the genetically modified plant from the cell.

Still another aspect of the present invention contemplates a method for producing a transgenic plant exhibiting altered inflorescence properties, said method comprising stably transforming a cell of a suitable plant with a nucleic acid sequence of the present invention, regenerating a transgenic plant from the cell and growing said transgenic plant for a time and under conditions sufficient to permit the expression of the nucleic acid sequence into an FMT.

Still a further aspect of the present invention contemplates a method for producing a plant exhibiting altered inflorescence properties, said method comprising alteration of the FMT gene through modification of the indigenous sequences via homologous recombination from an appropriately altered FMT gene or derivative or part thereof introduced into the plant cell, and regenerating the genetically modified plant from the cell.

Even yet another aspect of the present invention extends to a method for producing a transgenic plant capable of expressing a recombinant gene encoding an FMT or part thereof or which carries a nucleic acid sequence which is substantially complementary to all or a part of a mRNA molecule optionally transcribable where required to effect regulation of an FMT, said method comprising stably transforming a cell of a suitable plant with the isolated nucleic acid molecule comprising a sequence of nucleotides encoding, or complementary to a sequence encoding, an FMT, where necessary under conditions permitting the eventual expression of said isolated nucleic acid molecule, and regenerating a transgenic plant from the cell.

Even still another aspect of the present invention extends to all transgenic plants or parts of transgenic plants or progeny of the transgenic plants containing all or part of the nucleic acid sequences of the present invention, or antisense forms thereof and/or any homologs or related forms thereof and, in particular, those transgenic plants which exhibit altered inflorescence properties.

Even still another aspect of the present invention extends to all transgenic plants or parts of transgenic plants or progeny of the transgenic plants containing all or part of the nucleic acid sequences of the present invention, or antisense forms thereof and/or any homologs or related forms thereof and, in particular, those transgenic plants which exhibit altered aerial parts of the plant such as sepal, bract, petiole, peduncle, ovaries, anthers or stem properties.

Another aspect of the present invention contemplates the use of the extracts from transgenic plants or plant parts transgenic plants or progeny of the transgenic plants containing all or part of the nucleic acid sequences of the present invention and, in particular, the extracts from those transgenic plants when used as a flavoring or food additive or health product or beverage or juice or coloring.

A further aspect of the present invention is directed to recombinant forms of FMT.

Another aspect of the present invention contemplates the use of the genetic sequences described herein in the manufacture of a genetic construct capable of expressing an FMT or down-regulating an indigenous FMT enzyme in a plant.

Yet another aspect of the present invention is directed to a prokaryotic or eukaryotic organism carrying a genetic sequence encoding an FMT extrachromosomally in plasmid form.

Still another aspect of the present invention extends to a recombinant polypeptide comprising a sequence of amino acids substantially as set forth in SEQ ID NO:2 or SEQ ID NO:5 or SEQ ID NO:7 or SEQ ID NO:12 or SEQ ID NO:22 or SEQ ID NO:42 or SEQ ID NO:44 or an amino acid sequence having at least about 50% similarity to SEQ ID NO:2 or SEQ ID NO:5 or SEQ ID NO:7 or SEQ ID NO:12 or SEQ ID NO:22 or SEQ ID NO:42 or SEQ ID NO:44 or a derivative of said polypeptide.

TABLE 1

Summary of sequence identifiers

| SEQUENCE ID NO: | NAME | DESCRIPTION |
|---|---|---|
| 1 | *Petunia* difE nt sequence | cDNA nucleotide |
| 2 | *Petunia* difE aa seq | cDNA translated sequence |
| 3 | 'GAGATTT' | oligonucleotide |
| 4 | *Petunia* E20 nt seq | cDNA nucleotide |
| 5 | *Petunia* E20 aa | cDNA translated sequence |
| 6 | *Petunia* E33 nt | cDNA nucleotide |
| 7 | *Petunia* E33 corrected aa | cDNA amino acid (corrected) |
| 8 | 1903 F | FMT specific oligonucleotide |
| 9 | 1907BamHI F | FMT specific oligonucleotide |
| 10 | 1907Pst R | FMT specific oligonucleotide |
| 11 | *Torenia* TMT5.nt | cDNA nucleotide |
| 12 | *Torenia* TMT5.aa | cDNA translated sequence |
| 13 | TMT5.BamHI.F | oligonucleotide |
| 14 | TMT5.PstI.R | oligonucleotide |
| 15 | OMTIf2 | FMT specific oligonucleotide |
| 16 | OMTIf4 | FMT specific oligonucleotide |
| 17 | OMTIr3 | FMT specific oligonucleotide |
| 18 | OMTIr5 | FMT specific oligonucleotide |
| 19 | dT(17)Ad2Ad1 | oligonucleotide |
| 20 | GI-anchor | oligonucleotide |
| 21 | *Fuchsia* FMT nt | cDNA nucleotide |
| 22 | *Fuchsia* FMT aa | cDNA amino acid |
| 23 | OMT1f1 | FMT specific oligonucleotide |
| 24 | OMT1f3 | FMT specific oligonucleotide |
| 25 | OMT1r4 | FMT specific oligonucleotide |
| 26 | *Petunia* E33 nt (corrected) | cDNA nucleotide |
| 27 | Ad1 | oligonucleotide |
| 28 | petD8#1 | oligonucleotide |
| 29 | petD8#2 | oligonucleotide |
| 30 | PMT-F | FMT specific oligonucleotide |
| 31 | PMT-R | FMT specific oligonucleotide |
| 32 | TMT-F | FMT specific oligonucleotide |
| 33 | TMT-R | FMT specific oligonucleotide |
| 34 | FucR1 | FMT specific oligonucleotide |
| 35 | FucR3 | FMT specific oligonucleotide |
| 36 | FucR5 | FMT specific oligonucleotide |
| 37 | FucR6 | FMT specific oligonucleotide |
| 38 | FucF1 | FMT specific oligonucleotide |
| 39 | Tor 5' pos | FMT specific oligonucleotide |
| 40 | Tor 5' neg | FMT specific oligonucleotide |
| 41 | *Fuchsia* FMT (3282).nt | cDNA nucleotide |

TABLE 1-continued

Summary of sequence identifiers

| SEQUENCE ID NO: | NAME | DESCRIPTION |
|---|---|---|
| 42 | *Fuchsia* FMT (3282).aa | cDNA translated sequence |
| 43 | *Fuchsia* FMT full (3289).nt | cDNA nucleotide |
| 44 | *Fuchsia* FMT full (3289).aa | cDNA translated sequence |
| 45 | BamHI linker | oligonucleotide linker |
| 46 | AscII linker | oligonucleotide linker |
| 47 | SalI linker | oligonucleotide linker |

DETAILED DESCRIPTION OF THE PREFERRED EMBODIMENTS

Figure 1A:
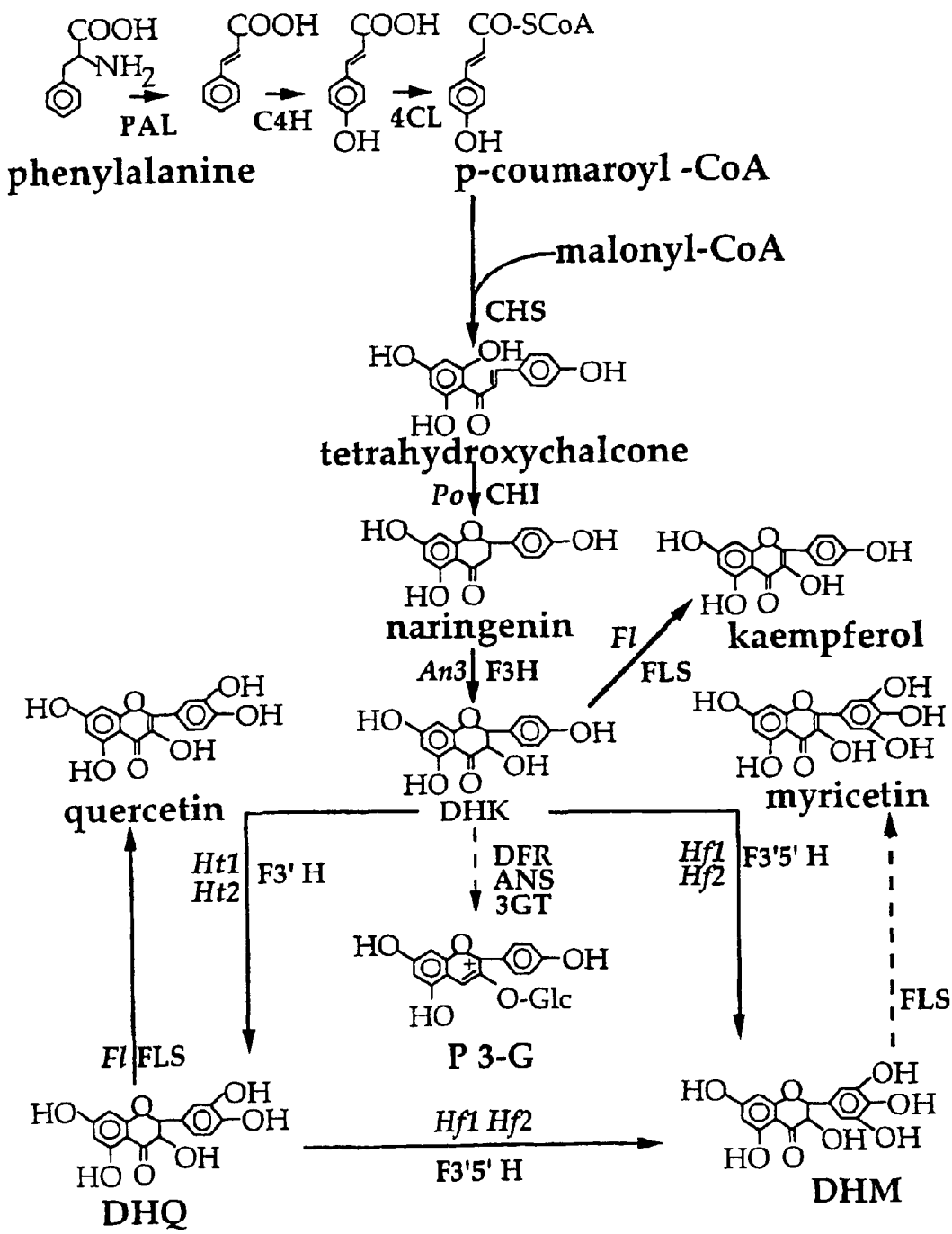
FIGS. 1A and 1B are schematic representations of the biosynthesis pathway for the flavonoid pigments in petunia. Enzymes involved in the pathway have been indicated as follows: PAL=Phenylalanine ammonia-lyase; C4H=Cinnamate 4-hydroxylase; 4CL=4-coumarate:CoA ligase; CHS=Chalcone synthase; CHI=Chalcone flavanone isomerase; F3H=Flavanone 3-hydroxylase; DFR=Dihydroflavonol 4-reductase; ANS=Anthocyanidin synthase, 3GT=UDP-glucose:flavonoid 3-O-glucosyltransferase; 3RT=UDP rhamnose:anthocyanidin 3-glucoside rhamnosyltransferase, AR-AT=Anthocyanidin rutinoside acyltransferase, 5GT=Anthocyanin 5-glucosyltransferase; 3' FMT=Flavonoid 3' O-methyltransferase, 3'5' FMT=Flavonoid 3', 5' O-methyltransferase. Other abbreviations include: DHK=dihydrokaempferol, DHQ=dihydroquercetin, DHM=dihydromyricetin, P 3-G=pelargonidin 3-glucoside. Some of the genetic loci that control these reactions in petunia are shown in italics alongside the enzymes. Myricetin and pelargonidin based pigments occur rarely in petunia.
Figure 1B:
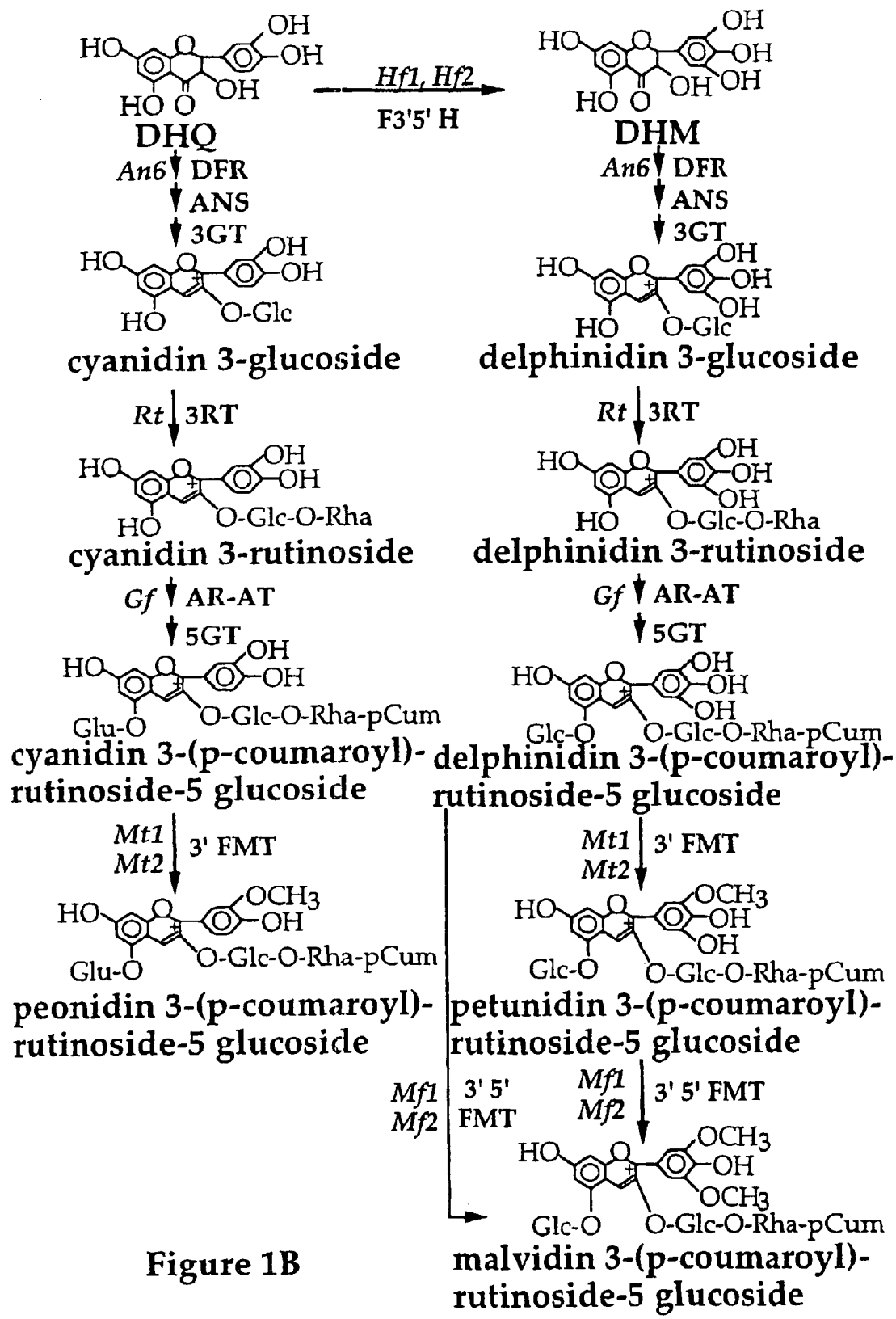

In accordance with the present invention, a genetic sequence encoding a methyltransferase and, more particularly, a flavonoid methyltransferase (hereinafter referred to as "FMT") has been identified and cloned. The recombinant sequence permits the modulation of methyltransferase when it is attached to a flavonoid molecule. Substrates include anthocyanins with a hydroxyl group attached to the molecule such as anthocyanins based on the anthocyanidins delphinidin, cyanidin and petunidin including but not limited to delphinidin 3-glucoside, cyanidin 3-glucoside, petunidin 3-glucoside, delphinidin 3,5-diglucoside, cyanidin 3,5-diglucoside, petunidin 3,5-diglucoside thereby providing a means to manipulate petal color. Accordingly, the present invention relates to the altering of FMT activity in plants, which encompasses elevating or reducing (i.e. modulating) levels of existing FMT activity by introducing a sequence of the present invention. Reduction in levels of FMT activity may also be referred to as down-regulation. Moreover, the present invention extends to plants and reproductive or vegetative parts thereof including flowers, seeds, vegetables, leaves, stems, etc., and more particularly, genetically modified or ornamental transgenic plants.

A "transgenic plant" includes any genetically modified plant and the terms "transgenic" and "genetically modified" may be used interchangeably through the subject specification.

Accordingly, one aspect of the present invention provides an isolated nucleic acid molecule comprising a sequence of nucleotides encoding, or complementary to a sequence encoding FMT or a functional derivative of the enzyme.

The present invention is described and exemplified herein by reference to the identification, cloning and manipulation of genetic sequences encoding FMT which, up to the present time, is a particularly convenient and useful flavonoid methyltransferase enzyme for the practice of the invention herein disclosed. This is done, however, with the understanding that the present invention extends to all novel FMT enzymes and their functional derivatives.

For convenience and by way of short hand notation only, reference herein to a flavonoid methylating enzyme includes FMTs acting on flavonoids such as anthocyanins, flavonols and/or flavones. Preferably, the flavonoid methylating enzyme is FMT. The FMT enzyme may also be considered to include a polypeptide or protein having FMT activity or FMT-like activity. The latter encompasses derivatives having altered FMT activities.

A preferred aspect of the present invention, therefore, is directed to an isolated nucleic acid molecule comprising a sequence of nucleotides encoding, or complementary to a sequence encoding FMT or a functional mutant, derivative, part, fragment, homolog or analog of FMT.

By the term "nucleic acid molecule" is meant a genetic sequence in a non-naturally occurring condition. Generally, this means isolated away from its natural state or synthesized or derived in a non-naturally-occurring environment. More specifically, it includes nucleic acid molecules formed or maintained in vitro, including genomic DNA fragments recombinant or synthetic molecules and nucleic acids in combination with heterologous nucleic acids. It also extends to the genomic DNA or cDNA or part thereof encoding FMT or a part thereof in reverse orientation relative to its own or another promoter. It further extends to naturally occurring sequences following at least a partial purification relative to other nucleic acid sequences.

The term "genetic sequences" is used herein in its most general sense and encompasses any contiguous series of nucleotide bases specifying directly, or via a complementary series of bases, a sequence of amino acids in an FMT enzyme. Such a sequence of amino acids may constitute a partial FMT such as set forth in SEQ ID NO:22 or SEQ ID NO:42 or a full-length FMT such as is set forth in SEQ ID NO:2 or SEQ ID NO:5 or SEQ ID NO:7 or SEQ ID NO:12 or SEQ ID NO:44 or an active truncated form thereof or may correspond to a particular region such as an N-terminal, C-terminal or internal portion of the enzyme. A genetic sequence may also be referred to as a sequence of nucleotides or a nucleotide sequence and include a recombinant fusion of two or more sequences.

The genetic sequence of the present invention may also be subject to modified codon usage to improve or otherwise facilitate expression in a particular host cell.

In accordance with the above aspects of the present invention there is provided a nucleic acid molecule comprising a nucleotide sequence or complementary nucleotide sequence substantially as set forth in SEQ ID NO:1 or SEQ ID NO:4 or SEQ ID NO:6 or SEQ ID NO:11 or SEQ ID NO:21 or SEQ ID NO:26 SEQ ID NO:41 or SEQ ID NO:43 or having at least about 50% similarity thereto or capable of hybridizing to the sequence set forth in SEQ ID NO:1 under low stringency conditions.

Alternative percentage similarity encompassed by the present invention include at least about 60% or at least about 70% or at least about 80% or at least about 90% or above, such as about 95% or about 96% or about 97% or about 98% or about 99%.

In a particularly preferred embodiment, there is provided an isolated nucleic acid molecule comprising a nucleotide sequence or complementary nucleotide sequence substantially as set forth in SEQ ID NO:1 or SEQ ID NO:4 or SEQ ID NO:6 or SEQ ID NO:11 or SEQ ID NO:21 or SEQ ID NO:26 or SEQ ID NO:41 or SEQ ID NO:43 having at least about 50% similarity thereto or capable of hybridising to the sequence set forth in SEQ ID NO:1 or SEQ ID NO:4 or SEQ ID NO:6 or SEQ ID NO:11 or SEQ ID NO:21 or SEQ ID NO:26 or SEQ ID NO:41 or SEQ ID NO:43 or complementary strands of either under low stringency conditions, wherein said nucleotide sequence encodes a polypeptide having FMT activity.

For the purposes of determining the level of stringency to define nucleic acid molecules capable of hybridizing to SEQ ID NO:1 or SEQ ID NO: 4 or SEQ ID NO: 6 or SEQ ID NO: 11 or SEQ ID NO: 21 or SEQ ID NO: 26 or SEQ ID NO:41 or SEQ ID NO:43 reference herein to a low stringency includes and encompasses from at least about 0% to at least about 15% v/v formamide and from at least about 1 M to at least about 2 M salt for hybridization, and at least about 1 M to at least about 2 M salt for washing conditions. Generally, low stringency is from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m = 69.3 + 0.41$ (G+C) % (Marmur and Doty, *J. Mol. Biol.* 5:109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 1.0% w/v SDS at 25-42° C.; a moderate stringency is 2×SSC buffer, 1.0% w/v SDS at a temperature in the range 20° C. to 65° C.; high stringency is 0.1×SSC buffer, 0.1% w/v SDS at a temperature of at least 65° C.

Another aspect of the present invention provides a nucleic acid molecule comprising a sequence of nucleotides encoding or complementary to a sequence encoding an amino acid sequence substantially as set forth in SEQ ID NO:2 or SEQ ID NO:5 or SEQ ID NO:7 or SEQ ID NO:12 or SEQ ID NO:22 or SEQ ID NO:42 or SEQ ID NO:44 or an amino acid sequence having at least about 50% similarity thereto.

The term similarity as used herein includes exact identity between compared sequences at the nucleotide or amino acid level. Where there is non-identity at the nucleotide level, similarity includes differences between sequences which result in different amino acids that are nevertheless related to each other at the structural, functional, biochemical and/or conformational levels. Where there is non-identity at the amino acid level, similarity includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al. (*Nucl. Acids Res.* 25: 3389, 1997). A detailed discussion of sequence analysis can be found in Unit 19.3 of Ausubel et al. (Current Protocols in Molecular Biology, John Wiley & Sons Inc, 1994-1998, Chapter 15, 1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

The nucleic acid sequences contemplated herein also encompass oligonucleotides useful as genetic probes for amplification reactions or as antisense or sense molecules capable of regulating expression of the corresponding gene in a plant. An antisense molecule as used herein may also encompass a genetic construct comprising the structural genomic or cDNA gene or part thereof in reverse orientation relative to its or another promoter. It may also encompass a homologous genetic sequence. An antisense or sense molecule may also be directed to terminal or internal portions of the gene encoding a polypeptide having FMT activity or to combinations of the above such that the expression of the gene is reduced or eliminated.

With respect to this aspect of the invention, there is provided an oligonucleotide of 5-50 nucleotides having substantial similarity or complementarity to a part or region of a molecule with a nucleotide sequence set forth in SEQ ID NO:1 or SEQ ID NO:4 or SEQ ID NO:6 or SEQ ID NO:11 or SEQ ID NO:21 or SEQ ID NO:26 or SEQ ID NO:41 or SEQ ID NO:43 or a complementary form thereof. By substantial similarity or complementarity in this context is meant a hybridizable similarity under low, alternatively and preferably medium and alternatively and most preferably high stringency conditions specific for oligonucleotide hybridization (Sambrook et al., *Molecular Cloning: A Laboratory Manual*. (2nd edition), Cold Spring Harbor Laboratory Press, USA, 1989). Such an oligonucleotide is useful, for example, in screening FMT genetic sequences from various sources or for monitoring an introduced genetic sequence in a transgenic plant. The preferred oligonucleotide is directed to a conserved FMT genetic sequence or a sequence conserved within a plant genus, plant species and/or plant variety.

In one aspect of the present invention, the oligonucleotide corresponds to the 5' or the 3' end of the FMT genetic sequence. For convenience, the 5' end is considered herein to define a region substantially between the start codon of the structural gene to a centre portion of the gene, and the 3' end is considered herein to define a region substantially between the centre portion of the gene and the terminating codon of the structural gene. It is clear, therefore, that oligonucleotides or probes may hybridize to the 5' end or the 3' end or to a region common to both the 5' and the 3' ends. The present invention extends to all such probes.

In one embodiment, the nucleic acid sequence encoding an FMT or various functional derivatives thereof is used to reduce the level of an endogenous FMT (e.g. via co-suppression) or other post transcriptional gene silencing (PTGS) processes including RNAi or alternatively the nucleic acid sequence encoding this enzyme or various derivatives or parts thereof is used in the antisense orientation to reduce the level of FMT. The use of sense strands, double or partially single stranded such as constructs with hairpin loops is particularly useful in inducing a PTGS response. In a further alternative, ribozymes could be used to inactivate target nucleic acid sequences.

Still a further embodiment encompasses post-transcriptional inhibition to reduce translation into polypeptide material.

Reference herein to the altering of FMT activity relates to an elevation or reduction in activity of up to 30% or more preferably of 30-50%, or even more preferably. 50-75% or still more preferably 75% or greater above or below the normal endogenous or existing levels of activity. Such elevation or reduction may be referred to as modulation of FMT enzyme activity. Generally, modulation is at the level of transcription or translation of FMT genetic sequences.

The nucleic acids of the present invention may be a ribonucleic acid or deoxyribonucleic acids, single or double stranded and linear or covalently closed circular molecules. Preferably, the nucleic acid molecule is cDNA. The present invention also extends to other nucleic acid molecules which hybridize under low, preferably under medium and most preferably under high stringency conditions with the nucleic acid molecules of the present invention and in particular to the sequence of nucleotides set forth in SEQ ID NO:1 or SEQ ID NO:4 or SEQ ID NO:6 or SEQ ID NO:11 or SEQ ID NO:21 or SEQ ID NO:26 or SEQ ID NO:41 or SEQ ID NO:43 or a part or region thereof. In its most preferred embodiment, the present invention extends to a nucleic acid molecule having a nucleotide sequence set forth in SEQ ID NO:1 or SEQ ID NO:4 or SEQ ID NO:6 or SEQ ID NO:11 or SEQ ID NO:21 or SEQ ID NO:26 or SEQ ID NO:41 or SEQ ID NO:43 or to a molecule having at least 40%, more preferably at least 45%, even more preferably at least 55%, still more preferably at least 65%-70%, and yet even more preferably greater than 85% similarity at the level of nucleotide or amino acid sequence to at least one or more regions of the sequence set forth in SEQ ID NO:1 or SEQ ID NO:4 or SEQ ID NO:6 or SEQ ID NO:11 or SEQ ID NO:21 or SEQ ID NO:26 or SEQ ID NO:41 or SEQ ID NO:43 and wherein the nucleic acid encodes or is complementary to a sequence which encodes an enzyme having FMT activity. It should be noted, however, that nucleotide or amino acid sequences may have similarities below the above given percentages and yet still encode FMT activity and such molecules may still be considered in the scope of the present invention where they have regions of sequence conservation. The present invention further extends to nucleic acid molecules in the form of oligonucleotide primers or probes capable of hybridizing to a portion of the nucleic acid molecules contemplated above, and in particular those set forth in SEQ ID NO:1 and/or SEQ ID NO:4 and/or SEQ ID NO:6 and/or SEQ ID NO:11 and/or SEQ ID NO:21 and/or SEQ ID NO:26 and/or SEQ ID NO:41 and/or SEQ ID NO:43, under low, preferably under medium and most preferably under high stringency conditions. Preferably the portion corresponds to the 5' or the 3' end of the gene. For convenience the 5' end is considered herein to define a region substantially between the start codon of the structural genetic sequence to a centre portion of the gene, and the 3' end is considered herein to define a region substantially between the centre portion of the gene and the terminating codon of the structural genetic sequence. It is clear, therefore, that oligonucleotides or probes may hybridize to the 5' end or the 3' end or to a region common to both the 5' and the 3' ends. The present invention extends to all such probes.

The term gene is used in its broadest sense and includes cDNA corresponding to the exons of a gene. Accordingly, reference herein to a gene is to be taken to include:—

(i) a classical genomic gene consisting of transcriptional and/or translational regulatory sequences and/or a coding region and/or non-translated sequences (i.e. introns, 5'- and 3'-untranslated sequences); or (ii) mRNA or cDNA corresponding to the coding regions (i.e. exons) and 5'- and 3'-untranslated sequences of the gene.

The term "gene" is also used to describe synthetic or fusion molecules encoding all or part of an expression product. In particular embodiments, the term "nucleic acid molecule" and "gene" may be used interchangeably.

The nucleic acid or its complementary form may encode the full-length enzyme or a part or derivative thereof. By "derivative" is meant any single or multiple amino acid substitutions, deletions, and/or additions relative to the naturally occurring enzyme and which retains FMT activity. In this regard, the nucleic acid includes the naturally occurring nucleotide sequence encoding FMT or may contain single or multiple nucleotide substitutions, deletions and/or additions to said naturally occurring sequence. The nucleic acid of the present invention or its complementary form may also encode a "part" of the FMT, whether active or inactive, and such a nucleic acid molecule may be useful as an oligonucleotide probe, primer for polymerase chain reactions or in various mutagenic techniques, or for the generation of antisense molecules.

Reference herein to a "part" of a nucleic acid molecule, nucleotide sequence or amino acid sequence, preferably relates to a molecule which contains at least about 10 contiguous nucleotides or five contiguous amino acids, as appropriate.

Amino acid insertional derivatives of the FMT of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Typical substitutions are those made in accordance with Table 2.

TABLE 2

Suitable residues for amino acid substitutions

| ORIGINAL RESIDUE | EXEMPLARY SUBSTITUTIONS |
|---|---|
| Ala | Ser |
| Arg | Lys |
| Asn | Gln; His |
| Asp | Glu |
| Cys | Ser |
| Gln | Asn; Glu |
| Glu | Asp |
| Gly | Pro |
| His | Asn; Gln |
| Ile | Leu; Val |
| Leu | Ile; Val |
| Lys | Arg; Gln; Glu |
| Met | Leu; Ile; Val |
| Phe | Met; Leu; Tyr |
| Ser | Thr |
| Thr | Ser |
| Trp | Tyr |
| Tyr | Trp; Phe |
| Val | Ile; Leu; Met |

Where the FMT is derivatized by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1-10 amino acid residues and deletions will range from about 1-20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield, *J. Am. Chem. Soc.* 85: 2149, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al., (1989), supra.

Other examples of recombinant or synthetic mutants and derivatives of the FMT enzyme of the present invention include single or multiple substitutions, deletions and/or additions of any molecule associated with the enzyme such as carbohydrates, lipids and/or proteins or polypeptides.

The terms "analogs" and "derivatives" also extend to any functional chemical equivalent of FMT and also to any amino acid derivative described above. For convenience, reference to FMT herein includes reference to any functional mutant, derivative, part, fragment, homolog or analog thereof.

The present invention is exemplified using nucleic acid sequences derived from *Petunia*, *Torenia* or *Fuchsia* since this represents the most convenient and preferred source of material to date. However, one skilled in the art will immediately appreciate that similar sequences can be isolated from any number of sources such as other plants or certain microorganisms. All such nucleic acid sequences encoding directly or indirectly an FMT are encompassed by the present invention regardless of their source. Examples of other suitable sources of genes encoding FMTs include, but are not limited to *Petunia* sp., *Plumbago* sp., *Vitis* sp., *Babiana stricta*, *Pinus* sp., *Picea* sp., *Larix* sp., *Phaseolus* sp., *Solanum* sp., *Vaccinium* sp., *Cyclamen* sp., *Iris* sp., *Pelargonium* sp., *Geranium* sp., *Pisum* sp., *Lathyrus* sp., *Clitoria* sp., *Catharanthus* sp., *Malvia* sp., *Mucuna* sp., *Vicia* sp., *Saintpaulia* sp., *Lagerstroemia* sp., *Tibouchina* sp., *Hypocalyptus* sp., *Rhododendron* sp, *Linum* sp., *Macroptilium* sp., *Hibiscus* sp., *Hydrangea* sp., *Ipomoea* sp., *Cymbidium* sp., *Millettia* sp., *Hedysarum* sp., *Lespedeza* sp., *Antigonon* sp., *Pisum* sp., etc.

In accordance with the present invention, a nucleic acid sequence encoding FMT may be introduced into and expressed in a transgenic plant in either orientation thereby providing a means either to convert suitable substrates, if synthesized in the plant cell, ultimately into peonidin, petunidin or malvidin derivatives or other methyl-flavonoids, or alternatively to inhibit such conversion of metabolites by reducing or eliminating endogenous or existing FMT activity. The production of these anthocyanins or other flavonoids will modify petal color and may contribute to the production of a bluer color. Expression of the nucleic acid sequence in the plant may be constitutive, inducible or developmental and may also be tissue-specific. The word "expression" is used in its broadest sense to include production of RNA or of both RNA and protein. It also extends to partial expression of a nucleic acid molecule.

The terms "genetically modified plant" and "transgenic plant" refer to any plant or progeny or subsequent offspring therefrom or vegetatively propagated new plant that has become transformed after the introduction of novel nucleic acid sequence using appropriate molecular biology techniques. The two terms are used interchangeably through out the specification. The nucleic acid sequence may be derived from the same or a different species of plant to that which is being transformed. It is contemplated that the nucleic acid could encode a polypeptide or be complementary to a sequence encoding a polypeptide or a mutant, derivative, part, fragment or portion thereof. Alternatively the nucleic acid sequence may be from the non-coding region of a genome.

The genetically modified or transgenic plants of the present invention include horticultural and agricultural species.

The term "horticultural plant species" includes but is not limited to floricultural plants (for example, cut-flowers, potted flowering plants), ornamental plants (for example, ornamental foliage plants) and all other forms of horticulture (such as, bedding plants, pot-plants, garden-plants).

The term "agricultural plant species" includes but is not limited to broad acre food and non-food crops (for example, wheat, corn, cotton, maize, pasture), fruit, nut and vegetable crops (for example apples, oranges, bananas, almonds, walnuts, macadamias, carrots, peas, potatoes, eggplants, grapes, tomatoes) and viticulture.

According to current understanding there will be some overlap between horticultural and agricultural plant species.

According to this aspect of the present invention, there is provided a method for producing a transgenic plant, such as but not limited to a transgenic flowering plant, capable of synthesizing FMT, said method comprising stably transforming a cell of a suitable plant with a nucleic acid sequence which comprises a sequence of nucleotides encoding said FMT under conditions permitting the eventual expression of said nucleic acid sequence, regenerating a transgenic plant from the cell and growing said transgenic plant for a time and under conditions sufficient to permit the expression of the nucleic acid sequence. The transgenic plant may thereby produce non-indigenous FMT at elevated levels relative to the amount expressed in a comparable non-transgenic plant.

Another aspect of the present invention contemplates a method for producing a transgenic plant with reduced indigenous or existing FMT activity, said method comprising stably transforming a cell of a suitable plant with a nucleic acid molecule which comprises a sequence of nucleotides encoding or complementary to a sequence encoding an FMT activity, regenerating a transgenic plant from the cell and where necessary growing said transgenic plant under conditions sufficient to permit the expression of the nucleic acid.

Yet another aspect of the present invention contemplates a method for producing a genetically modified plant with reduced indigenous or existing FMT activity, said method comprising altering the FMT gene through modification of the indigenous sequences via homologous recombination from an appropriately altered FMT gene or derivative or part thereof introduced into the plant cell, and regenerating the genetically modified plant from the cell.

As used herein an "indigenous" enzyme is one, which is native to or naturally expressed in a particular cell. A "non-indigenous" enzyme is an enzyme not native to the cell but expressed through the introduction of genetic material into a plant cell; for example, through a transgene. An "endogenous" enzyme is an enzyme produced by a cell but which may or may not be indigenous to that cell.

In a preferred embodiment, the present invention contemplates a method for producing a transgenic plant, such as but not limited to a transgenic flowering plant, exhibiting altered inflorescence properties, said method comprising stably transforming a cell of a suitable plant with a nucleic acid sequence of the present invention, regenerating a transgenic plant from the cell and growing said transgenic plant for a time and under conditions sufficient to permit the expression of the nucleic acid sequence into an FMT. Alternatively, said method may comprise stably transforming a cell of a suitable plant with a nucleic acid sequence of the present invention or its complementary sequence, regenerating a transgenic plant from the cell and growing said transgenic plant for a time and under conditions sufficient to alter the level of activity of the indigenous or existing FMT. Preferably the altered level would be less than the indigenous or existing level of FMT activity in a comparable non-transgenic plant. Without wishing to limit the present invention, one theory of mode of action is that reduction of the indigenous FMT activity requires the expression of the introduced nucleic acid sequence or its complementary sequence. However, expression of the introduced genetic sequence or its complement may not be required to achieve the desired effect: namely, a flowering plant exhibiting altered inflorescence properties.

The term "inflorescence" as used herein refers to the flowering part of a plant. As indicated above, reference to a "transgenic plant" may also be read as a "genetically modified plant".

In a related embodiment, the present invention contemplates a method for producing a plant such as but not limited to a transgenic flowering plant exhibiting altered inflorescence properties, said method comprising alteration of the FMT gene through modification of the indigenous sequences via homologous recombination from an appropriately altered FMT gene or derivative or part thereof introduced into the plant cell, and regenerating the genetically modified plant from the cell.

Preferably, the altered inflorescence includes the production of different shades of blue or red flowers or other colors, depending on the genotype and physiological conditions of the recipient plant.

Accordingly, the present invention extends to a method for producing a transgenic plant capable of expressing a recombinant gene encoding an FMT or part thereof or which carries a nucleic acid sequence which is substantially complementary to all or a part of a mRNA molecule optionally transcribable where required to effect regulation of an FMT, said method comprising stably transforming a cell of a suitable plant with the isolated nucleic acid molecule comprising a sequence of nucleotides encoding, or complementary to a sequence encoding, an FMT, where necessary under conditions permitting the eventual expression of said isolated nucleic acid molecule, and regenerating a transgenic plant from the cell. By "suitable plant" is meant a plant capable of producing anthocyanidin 3-glucosides and possessing the appropriate physiological properties required for the development of the color desired. Examples of suitable plants include but are not limited to *Torenia, Begonia, Cyclamen, Nierembergia, Catharanthus, Pelogonium, Orchid*, grape, *Euphorbia* or *Fuchsia*

One skilled in the art will immediately recognize the variations applicable to the methods of the present invention, such as increasing or decreasing the expression of the enzyme naturally present in a target plant leading to differing shades of colors such as different shades of blue, purple or red.

The present invention, therefore, extends to all transgenic plants or parts of transgenic plants or progeny of the transgenic plants containing all or part of the nucleic acid sequences of the present invention, or antisense forms thereof and/or any homologs or related forms thereof and, in particular, those transgenic plants which exhibit altered inflorescence properties. The transgenic plants may contain an introduced nucleic acid molecule comprising a nucleotide sequence encoding or complementary to a sequence encoding an FMT. Generally, the nucleic acid would be stably introduced into the plant genome, although the present invention also extends to the introduction of an FMT nucleotide sequence within an autonomously-replicating nucleic acid sequence such as a DNA or RNA virus capable of replicating within the plant cell. The invention also extends to seeds from such transgenic plants. Such seeds, especially if colored, are useful as proprietary tags for plants. Any and all methods for introducing genetic material into plant cells are encompassed by the present invention.

Another aspect of the present invention contemplates the use of the extracts from transgenic plants or plant parts of transgenic plants or progeny of the transgenic plants containing all or part of the nucleic acid sequences of the present invention and, in particular, the extracts from those transgenic plants when used as a flavoring or food additive or health product or beverage or juice or coloring.

Plant parts contemplated by the present invention includes, but is not limited to flowers, fruits, nuts, roots, stems, leaves or seeds.

The extracts of the present invention may be derived from the plants or plant part in a number of different ways including chemical extraction or heat extraction or filtration or squeezing or pulverization.

The plant, plant part or extract can be utilized in any number of different ways such as for the production of a flavoring (e.g. a food essence), a food additive (e.g. a stabilizer, a colorant) a health product (e.g. an antioxidant, a tablet) a beverage (e.g. wine, spirit, tea) or a juice (e.g. fruit juice) or coloring (e.g. food coloring, fabric coloring, dye, paint).

A further aspect of the present invention is directed to recombinant forms of FMT. The recombinant forms of the enzyme will provide a source of material for research to develop, for example, more active enzymes and may be useful in developing in vitro systems for production of colored compounds.

Still a further aspect of the present invention contemplates the use of the genetic sequences described herein in the manufacture of a genetic construct capable of expressing an FMT or down-regulating an indigenous FMT enzyme in a plant.

Another aspect of the present invention is directed to a prokaryotic or eukaryotic organism carrying a genetic sequence encoding an FMT extrachromosomally in plasmid form.

The present invention further extends to a recombinant polypeptide comprising a sequence of amino acids substantially as set forth in SEQ ID NO:2 or SEQ ID NO:5 or SEQ ID NO:7 or SEQ ID NO:12 or SEQ ID NO:22 or SEQ ID NO:42 or SEQ ID NO:43 or an amino acid sequence having at least about 50% similarity to SEQ ID NO:2 or SEQ ID NO:5 or SEQ ID NO:7 or SEQ ID NO:12 or SEQ ID NO:22 or SEQ ID NO:42 or SEQ ID NO:43 or a derivative of said polypeptide.

A "recombinant polypeptide" means a polypeptide encoded by a nucleotide sequence introduced into a cell directly or indirectly by human intervention or into a parent or other relative or precursor of the cell. A recombinant polypeptide may also be made using cell-free, in vitro transcription systems. The term "recombinant polypeptide" includes an isolated polypeptide or when present is a cell or cell preparation. It may also be in a plant or parts of a plant regenerated from a cell which produces said polypeptide.

A "polypeptide" includes a peptide or protein and is encompassed by the term "enzyme".

The recombinant polypeptide may also be a fusion molecule comprising two or more heterologous amino acid sequences.

The present invention is further described by the following non-limiting Examples.

Example 1

Plant Material

The *Petunia hybrida* cultivars used are presented in Table 3.

TABLE 3

Genotypes of *Petunia hybrida* cultivars

| Plant variety | Properties | Source/Reference |
|---|---|---|
| V23 | An1, An2, An3, An4, An6, An8, An9, An10, ph1, Hf1, Hf2, ht1, Rt, po, Bl, Fl | Wallroth et al. (Mol. Gen. Genet. 202: 6-15, 1986) Doodeman et al. (Theor. Appl. Genet. 67: 357-366, 1984) |
| R51 | An1, An2, An3, an4, An6, An8, An9, An10, An11, Ph1, hf1, hf2, Ht1, rt, Po, bl, fl | Wallroth et al. (1986), supra Doodeman et al. (1984), supra |
| VR | V23 × R51 F1 Hybrid | |
| Br140 | An1, An2, an4, an6/An6*, Ph1, Ph2, Ph5, Hf1, Ht1, Rt, po, Mt1, mf1, mf2, Gf, fl | INRA |
| Br140w | An1, An2, an4, an6*, Ph1, Ph2, Ph5, Hf1, Ht1, Rt, po, Mt1, mf1, mf2, Gf, fl | white flowering plants of a Br140 self |
| Br140p | An1, An2, an4, an6/An6*, Ph1, Ph2, Ph5, Hf1, Ht1, Rt, po, Mt1, mf1, mf2, Gf, fl | purple flowering plants of a Br140 self |
| Old Glory Blue (OGB) | $F_1$ Hybrid (commercial cultivar) | Ball Seed, USA |
| V26 | An1, An2, An3, an4, An6, An8, An9, An10, An11, Ph1, ph2, Ph5, Hf1, hf2, Ht1, Rt, po, Bl, Gf, Mt1, Mt2, mf1, mf2, Fl | INRA |
| W162 | an1 | Vrije Universiteit, Amsterdam |

INRA = Institut National de la Recherche Agronomique, Cedex, France

OGB petunia plants were grown in specialized growth rooms with a 14 hr day length at a light intensity of 10,000 lux and a temperature of 22 to 26° C. OGB flowers were harvested at developmental stages defined as follows:—

Stage 1: Unpigmented, closed bud (<25 mm in length).

Stage 2: Pigmented, closed bud (25-35 mm in length).

Stage 3: Dark purple bud with emerging corolla (>35 mm in length).

Stage 4: Dark purple opened flower pre-anther dehiscence (>50 mm in length).

Stage 5: Fully opened flower with all anthers dehisced.

Example 2

General Methods

In general, the methods followed were as described in Sambrook et al. (1989), supra.

*E. coli* Transformation

The *Escherichia coli* strains used were:—

DH5α supE44, Δ(lacZYA-ArgF)U169, (ø80lacZΔM15), hsdR17($r_k^-$, $m_k^+$), recA1, endA1, gyrA96, thi-1, relA1, deoR. (Hanahan, *J. Mol. Biol.* 166: 557, 1983 and. *Bethesda Res. Lab. Focus.* 8(2): 9, 1986).

XL1-Blue supE44, hsdR17($r_k^-$, $m_k^+$), recA1, endA1, gyrA96, thi-1, relA1, lac⁻, [F'proAB, lacI$^q$, lacZΔM15, Tn10(tet$^R$)] (Bullock et al., *Biotechniques* 5: 376, 1987).

PLK-F' recA, hsdR17($r_k^-$, $m_k^+$), mcrA⁻, mcrB⁻, lac⁻, supE44, galK2, galT22, metB1, [F' proAB, lacI$^q$, lacZΔM15, Tn10(tet$^R$)] (Stratagene).

M15 *E. coli* is derived from *E. coli* K12 and has the phenotype Nal$^s$, Str$^s$, Rif$^s$, Thi⁻, Ara⁺, Gal⁺, Mtl⁻, F⁻, RecA⁺, Uvr⁺, Lon⁺

The cloning vectors pBluescript, pBluescribe and PCR-script were obtained from Stratagene. pCR 2.1 was obtained from Invitrogen.

The bacterial expression vectors pQE-30 and pREP4 were obtained from QIAGEN.

Transformation of the *E. coli* strains was performed according to the method of Inoue et al., (*Gene* 96: 23-28, 1990).

DNA Ligations

DNA ligations were carried out using the Amersham Ligation Kit according to procedures recommended by the manufacturer.

Isolation and Purification of Fragments

Fragments were generally isolated on a 1% w/v agarose gel and purified using the QIAEX II Gel Extraction kit (QIAGEN).

Reparation of Overhanging Ends after Restriction Digestion

Overhanging 5' ends were repaired using DNA polymerase (Klenow fragment) according to standard protocols (Sambrook et al., 1989, supra). Overhanging 3' ends were repaired using T4 DNA polymerase according to standard protocols (Sambrook et al, 1989, supra).

Removal of Phosphoryl Groups from Nucleic Acids

Shrimp alkaline phosphatase (SAP) (USB) was typically used to remove phosphoryl groups from cloning vectors to prevent re-circularization according to the manufacturer's recommendations.

$^{32}$P-Labelling of DNA Probes

DNA fragments (50 to 100 ng) were radioactively labelled with 50 μCi of [α-$^{32}$P]-dCTP using a Gigaprime kit (Geneworks). Unincorporated [α-$^{32}$P]-dCTP was removed by chromatography on a Sephadex G-50 (Fine) column.

Plasmid Isolation

Helper phage R408 (Stratagene) was used to excise pBluescript phagemids containing petunia cDNA inserts from the amplified λZAP cDNA libraries using methods described by the manufacturer. *E. coli* XL1-Blue were transfected with the phagemid mixture and the colonies were plated out on LB plates (Sambrook et al., 1989, supra) containing 100 µg/mL ampicillin. Single colonies were analyzed for cDNA inserts by growing in LB broth (Sambrook et al., 1989, supra) with ampicillin (100 µg/mL) (or other appropriate antibiotic) and isolating the plasmid using the alkali-lysis procedure (Sambrook et al., 1989, supra) or using the WizardPlus SV minipreps DNA purification system (PROMEGA). Once the presence of a cDNA insert had been determined, larger amounts of plasmid DNA were prepared from 50 mL overnight cultures using a QIAfilter Plasmid midi kit (QIAGEN).

DNA Sequence Analysis

DNA sequencing was performed using the ABI PRISM® BigDye™ Primer Cycle Sequencing Kits from Applied Biosystems. The protocols supplied by the manufacturer were followed. The cycle sequencing reactions were performed using a Perkin Elmer PCR machine (GeneAmp PCR System 9600). Sequencing runs were performed by AGRF (Australian, Genome Research Facility) at WEHI (The Walter and Eliza Hall Institute of Medical Research) in Melbourne, Australia.

Homology searches against Genbank, SWISS-PROT and EMBL databases were performed using the FASTA and TFASTA programs (Pearson and Lipman, *Proc. Natl. Acad. Sci. USA* 85: 2444-2448, 1988) or BLAST programs (Altschul et al., *J. Mol. Biol.* 215: 403-410, 1990). Percentage sequence similarities were obtained using the LFASTA program (Pearson and Lipman, 1988, supra). In all cases, ktup values of 6 for nucleotide sequence comparisons and two for amino acid sequence comparisons were used, unless otherwise specified.

Multiple sequence alignments and dendogram plots were produced using ClustalW (Thompson et al., *Nucl. Acids Res.* 2: 4673-4680, 1994).

Example 3

Plant Transformations

*Agrobacterium rumefaciens* Transformations

The disarmed *Agrobacterium tumefaciens* strain used was AGL0 (Lazo et al., *Bio/technology* 9: 963-967, 1991).

Plasmid DNA was introduced into the *Agrobacterium tumefaciens* strain AGL0 by adding 5 µg of plasmid DNA to 100 µL of competent AGL0 cells prepared by inoculating a 50 mL LB culture (Sambrook et al., 1989, supra) and incubation for 16 hours with shaking at 28° C. The cells were then pelleted and resuspended in 0.5 mL of 85% v/v 100 mM $CaCl_2$/15% v/v glycerol. The DNA-Agrobacterium mixture was frozen by incubation in liquid $N_2$ for 2 minutes and then allowed to thaw by incubation at 37° C. for 5 minutes. The DNA/bacterial mix was then placed on ice for a further 10 minutes. The cells were then mixed with 1 mL of LB (Sambrook et al., 1989 supra) media and incubated with shaking for 16 hours at 28° C. Cells of *A. tumefaciens* carrying the plasmid were selected on LB agar plates containing appropriate antibiotics such as 50 µg/mL tetracycline or 100 µg/mL gentamycin or 30 µg/mL kanamycin. The confirmation of the plasmid in *A. tumefaciens* was done by restriction endonuclease mapping of DNA isolated from the antibiotic-resistant transformants.

*Petunia hybrida* Transformations

As described in Holton et al. (*Nature*, 366: 276-279, 1993) or Brugliera et al., (*Plant J.* 5, 81-92, 1994) by any other method well known in the art.

(a) Plant Material

Leaf tissue from mature plants of *P. hybrida* cv VR was treated with 1.25% w/v sodium hypochlorite for 2 minutes and then rinsed three times in sterile water. The leaf tissue was then cut into 25 $mm^2$ squares and precultured on MS media (Murashige and Skoog, *Physiol. Plant* 15: 73-97, 1962) supplemented with 0.05 mg/L kinetin and 1.0 mg/L 2,4-dichlorophenoxyacetic acid (2,4-D) for 24 hours.

(b) Co-Cultivation of *Agrobacterium* and *Petunia* Tissue

*A. tumefaciens* strain AGL0 (Lazo et al., 1991, supra) containing the binary vector were maintained at 4° C. on MG/L (Garfinkel and Nester, *J. Bacteriol.* 144:732-743, 1980) or LB agar (Sambrook et al., 1989, supra) plates containing the appropriate antibiotic. A single colony used to inoculate an overnight liquid culture containing 1% w/v Bacto-peptone, 0.5% w/v Bacto-yeast extract and 1% w/v NaCl. A final concentration of $5\times10^8$ cells/mL was prepared the next day by dilution in liquid MS medium containing B5 vitamins (Gamborg et al., *Exp. Cell Res.* 50: 151-158, 1968) and 3% w/v sucrose (BPM). The leaf discs were dipped for 2 minutes into BPM containing the transformed AGL0 as described above. The leaf discs were then blotted dry and placed on co-cultivation media for 4 days. The co-cultivation medium consisted of SH medium (Schenk and Hildebrandt, *Can. J. Bot.* 50: 199-204, 1972) supplemented with 0.05 mg/L kinetin and 1.0 mg/L 2,4-D and included a feeder layer of tobacco cell suspension spread over the co-cultivation medium with a filter paper placed on top of the tobacco cell suspension.

(c) Recovery of Transgenic *Petunia* Plants

After co-cultivation, the leaf discs were transferred to MS medium supplemented with 3% w/v sucrose, 1 mg/L α-benzylaminopurine (BAP), 0.1 mg/L α-naphthalene acetic acid (NAA), 2 µg/L Chlorsulfuron (Chem Service), 350 mg/L cefotaxime and 0.3% w/v Gelrite Gellan Gum (Schweizerhall) (selection medium). Regenerating explants were transferred to fresh selection medium after 4 weeks. Adventitious shoots which survived the Chlorsulfuron selection were isolated and transferred to BPM containing 2 µg/L Chlorsulfuron (Chem Service) and 200 mg/L cefotaxime for root induction. All cultures were maintained under a 16 hr photoperiod (60 µmol. $m^{-2}$, $s^{-1}$ cool white fluorescent light) at 23±2° C. When roots reached 2-3 cm in length the transgenic petunia plantlets were transferred to autoclaved Debco 51410/2 potting mix in 8 cm tubes. After 4 weeks plants were transferred into 15 cm pots using the same potting mix and maintained at 23° C. under a 14 hour photoperiod (300 µmol $m^{-2}$, $s^{-1}$ mercury halide light).

*Rosa hybrida* Transformations

As described in U.S. Pat. No. 6,542,841 (PCT/US91/04412) or Robinson and Firoozabady (*Scientia Horticulturae*, 55: 83-99, 1993), Rout et al. (*Scientia Horticulturae*, 81: 201-238, 1999) or Marchant et al. (*Molecular Breeding* 4: 187-194, 1998) or by any other method well known in the art.

Cuttings of *Rosa hybrida* were generally obtained from Van Wyk and Son Flower Supply, Victoria, Australia or Keisei Roses, Japan Color Coding The Royal Horticultural Society's Color Chart (Kew, UK) was used to provide a description of color observed. They provide an alternative means by which to describe the color phenotypes observed. The designated numbers, however, should be taken only as a guide to the perceived colors and should not be regarded as limiting the possible colors, which may be obtained.

Construct Preparations

TABLE 4

Abbreviations used in construct preparations

| ABBREVIATION | DESCRIPTION |
|---|---|
| 35S 5' | ~0.2 kb incorporating BglII fragment containing the promoter region from the Cauliflower Mosaic Virus 35S gene (CaMV 35S) (Franck et al., Cell 21: 285-294, 1980, Guilley et al., Cell, 30: 763-773. 1982) |
| e35S 5' | ~0.7 kb fragment incorporating an enhanced CaMV 35S promoter (Mitsuhashi et al. Plant Cell Physiol. 37: 49-59, 1996) |
| GUS | β-glucuronidase coding sequence (Jefferson, et al., EMBO J. 6: 3901-3907, 1987) |
| Mac | Hybrid promoter consisting of the promoter from the mas gene and a CaMV 35S enhancer region (Comai et al., Plant Mol. Biol. 15: 373-381, 1990) |
| nos 5' | Promoter region from nopaline synthase gene of *A. tumefaciens* (Depicker, A. et al., J Mol. and Appl. Genetics, 1: 561-573, 1982) |
| nos 3' | Terminator region from nopaline synthase gene of A. tumefaciens (Depicker, A. et al., 1982, supra) |
| nptII | Kanamycin-resistance gene (encodes neomycin phosophotransferase which deactivates aminoglycoside antibiotics such as kanamycin, neomycin and G418) |
| ocs 3' | Terminator region from octopine synthase gene of A. tumefaciens (described in Klee et al., Bio/Technology 3: 637-642, 1985) |
| petD8 3' | ~0.8 kb fragment incorporating the terminator region from phospholipid transfer protein gene (D8) of Petunia hybrida cv. OGB (Holton, 1992, supra) |
| SuRB | Chlorsulfuron-resistance gene (encodes Acetolactate Synthase) with its own terminator from *Nicotiana tabacum* (Lee et al., EMBO J. 7: 1241-1248, 1988 |
| BP#40 or Viola F3'5'H | ~1.7 kb fragment containing F3'5'H cDNA clone from Viola sp. cultivar black pansy. (Australian Provisional Patent Applications No. 2002951088 and 2002952835 entitled "Genetic Sequences and uses therefor", 2002) |
| PFMT | ~1.0 kb fragment incorporating the *Petunia* flavonoid methyltransferase E20 cDNA clone (inter alia) |
| TFMT | ~1.0 kb fragment incorporating the *Torenia* flavonoid methyltransferase cDNA clone (inter alia) |
| FFMT | ~1.0 kb fragment incorporating the *Fuchsia* flavonoid methyltransferase cDNA clone (inter alia) |

Example 4

Incubation of Excised Petals with Precursors or End Products

Reports in the literature suggest that of the six principally occurring anthocyanidins found in nature (Table 5), the degree of "blueness" of an individual anthocyanidin is influenced by the hydroxylation and/or methylation pattern in the anthocyanin "B" ring. However, in 0.01% HCl/MeOH (v/v) solutions delphinidin has a higher $\lambda_{max}$ value than peonidin or malvidin and so appears the bluest of the six anthocyanidins.

TABLE 5

$\lambda_{max}$ values (in nm) of major anthocyanidins

| ANTHOCYANIDIN | $\lambda_{max}$ nm* |
|---|---|
| Pelargonidin | 520 |
| Cyanidin | 535 |
| Peonidin | 532 |
| Delphinidin | 546 |
| Petunidin | 543 |
| Malvidin | 542 |

$\lambda_{max}$ nm* wavelength of maximum absorption in 0.01% HCl/MeOH (v/v)

Data reviewed by Haslam (Practical Phenolics. From structure to molecular recognition and physiological action. Cambridge University Press, UK, 1998).

Experiments were set up to determine whether the production of delphinidin or its methylated derivative, malvidin would lead to novel colors in rose petals. To determine whether rose petals contained the enzymes necessary for conversion of dihydromyricetin to delphinidin, precursor-feeding experiments with dihydromyricetin were initiated.

Petal segments of a selection of commercial cultivars of roses (Toplesse, Lambada, Medeo, Pamela, Sonia, Oceana, Mystique) were placed in solutions of 1-2 mg/mL dihydromyrectin or water only and incubated for around 16 hours in a growth room at a temperature of around 23° C. Pink/purple colors were observed near the cut edges of the petals (Table 6). TLC analysis of the anthocyanidins in the pink/purple segments revealed the production of delphinidin. These results confirmed that the anthocyanin pathway enzymes of roses were able to convert dihydromyricetin to delphinidin.

TABLE 6

Colors produced in rose petals after incubation in dihydromyricetin (the precursor of delphinidin-based pigments)

| Rose cultivar | Color of rose petal | Color at cut edge after incubation in DHM |
|---|---|---|
| Toplesse | pink | pink/purple |
| Lambada | orange | pink/purple |
| Medeo | pale apricot | pink/purple |

TABLE 6-continued

Colors produced in rose petals after incubation in dihydromyricetin (the precursor of delphinidin-based pigments)

| Rose cultivar | Color of rose petal | Color at cut edge after incubation in DHM |
|---|---|---|
| Pamela | white/pale pink | pink/purple |
| Sonia | apricot/pink | pink/purple |
| Oceana | cream | pink/purple |
| Mystique | apricot | pink/purple |

DHM = dihydromyricetin

Rose petals from Toplesse and Lambada were subsequently incubated with malvidin 3,5-diglucoside to determine the color that may be obtained if this novel anthocyanin were to be produced in rose via introduction of a flavonoid 3'5' hydroxylase gene for production of delphinidin-based pigments and an flavonoid 3'5' methyltransferase gene (or flavonoid 3' methyltransferase and flavonoid 5' methyltransferase genes) for the subsequent conversion to malvidin-based pigments.

Petal segments of roses were placed in solutions of 1-2 mg/mL malvidin 3,5-diglucoside, 1-2 mg/mL dihydromyrectin or water only and incubated for around 16 hours in a growth room at a temperature of around 23° C. The production of colors in the purple range were observed near the cut edges of the petals upon incubation with dihydromyrectin or malvidin 3,5-diglucoside (Table 7). However a direct comparison of the colors observed with the production of delphinidin in the rose petals to the accumulation of malvidin in the same rose background surprisingly revealed that malvidin pigments resulted in bluer colors.

TABLE 7

Colors observed in rose petals after incubation in dihydromyricetin (the precursor of delphinidin-based pigments) or in malvidin 3,5-diglucoside

| Rose cultivar | Petal color | Color at cut edge upon production of delphinidin | Color at cut edge after incubation with malvidin |
|---|---|---|---|
| Toplesse | pink | pink/purple | violet/purple |
| Lambada | orange | pink/purple | violet/purple |

Reconstruction Experiments

Reconstruction experiments with rose petal extracts and various anthocyanins were performed to predict the color that would be produced in roses upon production of delphinidin or malvidin-based pigments.

The rose cultivar Medeo generally produces cream-colored to pale apricot flowers (RHSCC 158C to 159A). HPLC analysis of the anthocyanidins and flavonols accumulating in Medeo rose petals revealed that the petals accumulate high levels of flavonols (2.32 mg/g kaempferol, 0.03 mg/g quercetin) and very low levels of anthocyanins (0.004 mg/g cyanidin, 0.004 mg/g pelargonidin). The estimated vacuolar pH of Medeo petals is around 4.6. The petal juice of Medeo roses was extracted by grinding one petal with 50 µL of water using a mortar and pestle. The petal juice was collected and mixed with 10-20 µL of 1-2 mg/g delphinidin 3-glucoside, delphinidin 3,5-diglucoside and malvidin 3,5-diglucoside. The colors observed were described according to the Royal Horticultural Society Color Charts (RHSCC) (The Royal Horticultural Society, London) (Table 8).

TABLE 8

Colors observed upon addition of delphinidin 3-glucoside, delphinidin 3,5-diglucoside or malvidin 3,5-diglucoside to petal juice extracted from Medeo rose petals

| ANTHOCYANIN | pH | RHSCC# | COLOR |
|---|---|---|---|
| D3G | 4.9 | 74A | red-purple |
| D35G | 4.9 | 88A | violet |
| D35G | 4.6 | 88A | violet |
| M35G | 4.9 | 90A | violet-blue |
| M35G | 4.6 | 88A/90A | violet-blue |

D3G = delphinidin 3-glucoside,
D35G = delphinidin 3,5-diglucoside
M35G = malvidin 3,5-diglucoside Based on the $\lambda_{max}$ value (Table 5), it was assumed that the production of delphinidin pigments in rose petals would result in a bluer color than the production of malvidin pigments. However, from the feeding and reconstruction experiments detailed above it is clear that the production of malvidin-based pigments in rose petals will lead to bluer colors than that of delphinidin-based pigments.

Example 5

Isolation of a Partial
S-adenosyl-L-methionine:Flavonoid
Methyltransferase (FMT) cDNA Clone from *Petunia hybrida*

Construction and Screening of a *P. hybrida* cv. V26 Petal cDNA Library

A cDNA library was constructed based on mRNA from corolla limb tissue of the line V26 (An1+) (Kroon et al., *Plant J* 5: 69-80, 1994). Around 30,000 pfu of the V26 floral cDNA library were plated at a density of 800 pfu per 90 mm plate. Duplicate lifts of these were taken onto Hybond-N membranes (Amersham) and treated as recommended by the manufacturer. The filters were hybridized with first strand cDNA from an An1+ (V26) and an an1− line (W162). Hybridization conditions included a prehybridization step in 50% v/v formamide, 5×SSPE, 5×Denhardt's, 0.1% w/v SDS, 100 µg/mL herring sperm DNA at 42° C. for 3 hours. For hybridization 1.0×10$^8$ cpm $^{32}$P-labeled first strand cDNA and 100 µg of poly (A) were added and incubation was continued for 16-48 hours at 42° C. The filters were washed in 1×SSC/0.1% w/v SDS at 60° C. for 30 minutes and then exposed to Kodak XAR film for 3 to 4 days. Two hundred and seventy plaque forming units (pfu) out of 30,000 showed substantially stronger hybridization to the An1+ cDNA probe than to the an1− cDNA probe. Of these, 35 which did not hybridize to previously cloned pigmentation genes (chs, chi and dfr) were purified to homogeneity. Pairwise cross-hybridizations demonstrated that these 35 clones represented 7 distinct classes of genes-difA, difC, difE, difF, difG, difH and difI. The difG gene has subsequently been shown to represent the Rt gene of *Petunia hybrida* (Kroon et al., 1994, supra). The expression profiles of the remaining 6 classes were shown to display a spatial, temporal and genetic control similar to that of difG (Kroon et al., 1994, supra).

The difC clone was subsequently shown to represent the anthocyanidin 3-rutinoside acyltransferase (AR-AT) gene of *Petunia hybrida* (International Application No. PCT/AU01/00358; International Publication No. WO 01/72984).

Figure 2:
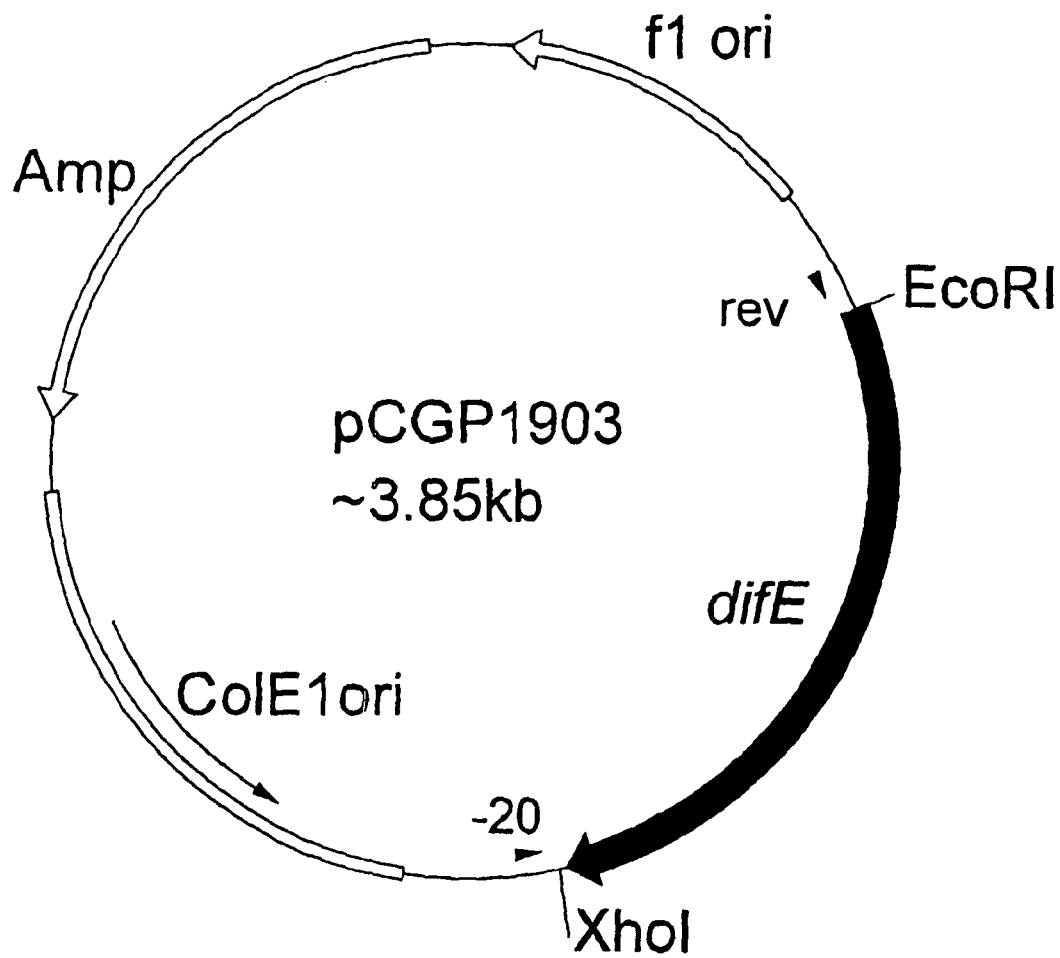
FIG. 2 is a diagrammatic representation of the plasmid pCGP1903 containing the difE cDNA clone from *P. hybrida* cv. V26. $^{32}$P-labelled fragments of the 0.9 kb EcoRI/XhoI fragment were used to probe the Old Glory Blue petal cDNA library. Abbreviations are as follows: Amp=the ampicillin resistance gene which confers resistance to the antibiotic ampicillin, f1 ori (+)=f1 filamentous phage origin of replication, ColE1ori=plasmid origin of replication, rev=approximate location of the M13 reverse primer site used in sequence analysis, -20=approximate location of the M13-20 primer site used in sequence analysis. Selected restriction enzyme sites are also marked.

The difE clone was shown to be around 1 kb and the plasmid was assigned the designation pCGP1903 (FIG. 2).

The complete sequence of the difE cDNA clone (SEQ ID NO:1) (contained in pCGP1903) was determined by compilation of sequence from different pUC18 subclones obtained using standard procedures for the generation of randomly-overlapping clones (Sambrook et al., 1989, supra). Blast searches against sequences in the GenBank database revealed similarities to caffeoyl-CoA O-methyltransferase mRNAs. (e.g. 84% identity over a 92 bp span of *Mesembryanthemum crystallinum* caffeoyl-CoA O-methyltransferase (AF053553)).

RFLP analysis indicated that the difE clone was linked to the Hf2 and Po loci (5 cross overs out of 33 plants with the Po locus and 8 cross overs with Hf2 out of 34 plants) on chromosome V and so was a candidate for the Mt2 or Mf2 gene. RNA gel blots were subsequently performed on various Mf and Mt mutants and it was shown that four-double mutants (mf1−, mf2−, mt1−, mt2−) lacked transcripts hybridising to difE, while lines dominant for one or more of these loci did contain difE transcripts. This suggested that the difE clone encoded a flavonoid methyltransferase and that the different FMT transcripts cross-hybridise. The difE clone was selected for further analysis.

Example 6

Isolation of a Full-Length FMT cDNA Clone from *Petunia hybrida* cv Old Glory Blue (OGB)

Construction of OGB Petal cDNA Library

Total RNA was isolated from the petal tissue of *P. hybrida* cv Old Glory Blue (OGB) stage 3 to 4 flowers using the method of Turpen and Griffith (*BioTechniques* 4: 11-15, 1986). Poly(A)$^+$ RNA was selected from the total RNA by three cycles of oligo-dT cellulose chromatography (Aviv and Leder, *Proc. Natl. Acad. Sci. USA* 69: 1408, 1972).

Two micrograms of poly(A)$^+$ RNA were reverse transcribed in a 20 µL reaction volume containing 1× Superscript™ reaction buffer, 10 mM dithiothreitol, 500 µM dATP, 500 µM dGTP, 500 µM dTTP, 500 µM 5-methyl-dCTP, 0.75 µg oligonucleotide (5' GAGAGAGAGAGAGAGAGAGATCTC-GAGTTTTTTTTTTTTTTTTTT) [SEQ ID NO:3] and 2 µL Superscript™ reverse transcriptase (BRL). The reaction mix was incubated at 37° C. for 50 minutes, 44° C. for 10 minutes and then placed on ice.

A second strand reaction mix (140 µL) was added to the first strand reaction mix. The second strand reaction mix consisted of 21 mM Tris-HCl, 104 mM KCl, 5.3 mM MgCl$_2$, 171 µM β-NAD, 11.4 mM (NH$_4$)$_2$SO$_4$, 214 µM dATP, 642 µM dCTP, 214 µM dGTP, 214 µM dTTP, 4 mM DTT, 10 µCi $^{32}$P-dCTP (3000 Ci/mMole), 15 units *E. coli* DNA ligase, 40 units *E. coli* DNA polymerase I (Boehringer) and 0.8 units RNAse H. The final mixture was incubated for 150 minutes at 16° C. To make the double-stranded cDNA blunt-ended, 10 units T4 DNA polymerase was added, and the reaction continued for a further 15 minutes at 16° C. The reaction was stopped and the cDNA purified by phenol/chloroform extraction, followed by chloroform extraction and ethanol precipitation.

EcoRI adaptors (Promega) were ligated with the cDNA and then kinased using conditions recommended by the manufacturer. The enzymes were denatured by heat (70° C., 20 minutes) and the DNA was purified by phenol/chloroform extraction and ethanol precipitation. The cDNA was digested with 50 units of XhoI restriction endonuclease (Boehringer Mannheim) in a reaction volume of 100 µL, using conditions recommended by the manufacturer. The enzyme was heat killed (70° C., 20 minutes) and the mixture passed through an S400 spin column (Pharmacia) which had been equilibrated in STE buffer (Sambrook et al., 1989, supra). The eluate was phenol/chloroform extracted and ethanol precipitated. After microcentrifugation at 4° C. for 30 minutes the resulting cDNA pellet was rinsed with 70% v/v ethanol, air dried and resuspended in 10 µL of TE buffer (1 mM Tris-HCl (pH 7.5), 1 mM EDTA).

A 2.5 µL aliquot of the resuspended cDNA mixture was ligated with 1 µg λZAPII EcoRI/XhoI/CIAP (calf intestinal alkaline phosphatase) treated vector (Stratagene) in 5 µL of reaction buffer consisting of 50 mM Tris-HCl (pH 7.0), 10 mM MgCl$_2$, 10 mM dithiothreitol, 1 mM ATP and 2 units of T4 DNA ligase. The reaction was carried out at 4° C. for 4 days.

After a subsequent incubation at room temperature for two hours, the ligation reaction mixture was packaged using the Packagene system (Promega). The total number of recombinants was 1×10$^6$ pfu.

After transfecting PLK-F' cells, the packaged λZAPII/cDNA was plated at 50,000 pfu per 15 cm diameter petri plate. The plates were incubated at 37° C. for eight hours, and the phage were eluted in 100 mM NaCl, 8 mM MgSO$_4$, 50 mM Tris-HCl pH 8.0, 0.01% gelatin (Phage Storage Buffer (PSB)). Chloroform was added and the phage stored at 4° C. as an amplified library.

40,000 pfu of the amplified library were plated onto NZY plates (Sambrook et al., 1989, supra) at a density of 20,000 pfu per 15 cm plate after transfecting XL1-Blue MRF' cells, and incubated at 37° C. for 8 hours. After a subsequent incubation at 4° C. overnight, duplicate lifts were taken onto Colony/Plaque Screen™ filters (DuPont) which were then treated as recommended by the manufacturer.

Screening of OGB Library

Prior to hybridization, the duplicate plaque lifts were washed in pre-washing solution (50 mM Tris-HCl pH 7.5, 1 M NaCl, 1 mM EDTA, 0.1% w/v sarcosine) at 65° C. for 30 minutes; stripped in 0.4 M sodium hydroxide at 65° C. for 30 minutes; then washed in a solution of 0.2 M Tris-HCl pH 8.0, 0.1×SSC, 0.1% w/v SDS at 65° C. for 30 minutes and finally rinsed in 2×SSC, 1.0% w/v SDS.

The duplicate lifts from the OGB petal cDNA library were screened with $^{32}$P-labelled fragments of an EcoRI/XhoI difE fragment from pCGP1903 (FIG. 2).

Hybridization conditions included a prehybridization step in 50% v/v formamide, 1 M NaCl, 10% w/v dextran sulphate, 1% w/v SDS at 42° C. for at least 1 hour. The $^{32}$P-labeled fragments (at 1×10$^6$ cpm/mL) were then added to the hybridization solution and hybridization was continued at 42° C. for a further 16 hours. The filters were then washed in 2×SSC, 1% w/v SDS at 42° C. for 2×30 minutes followed by a wash in 0.2×SSC, 1% w/v SDS at 65° C. for 30 minutes and exposed to Kodak XAR film with an intensifying screen at −70° C. for 4 hours.

Figure 3:
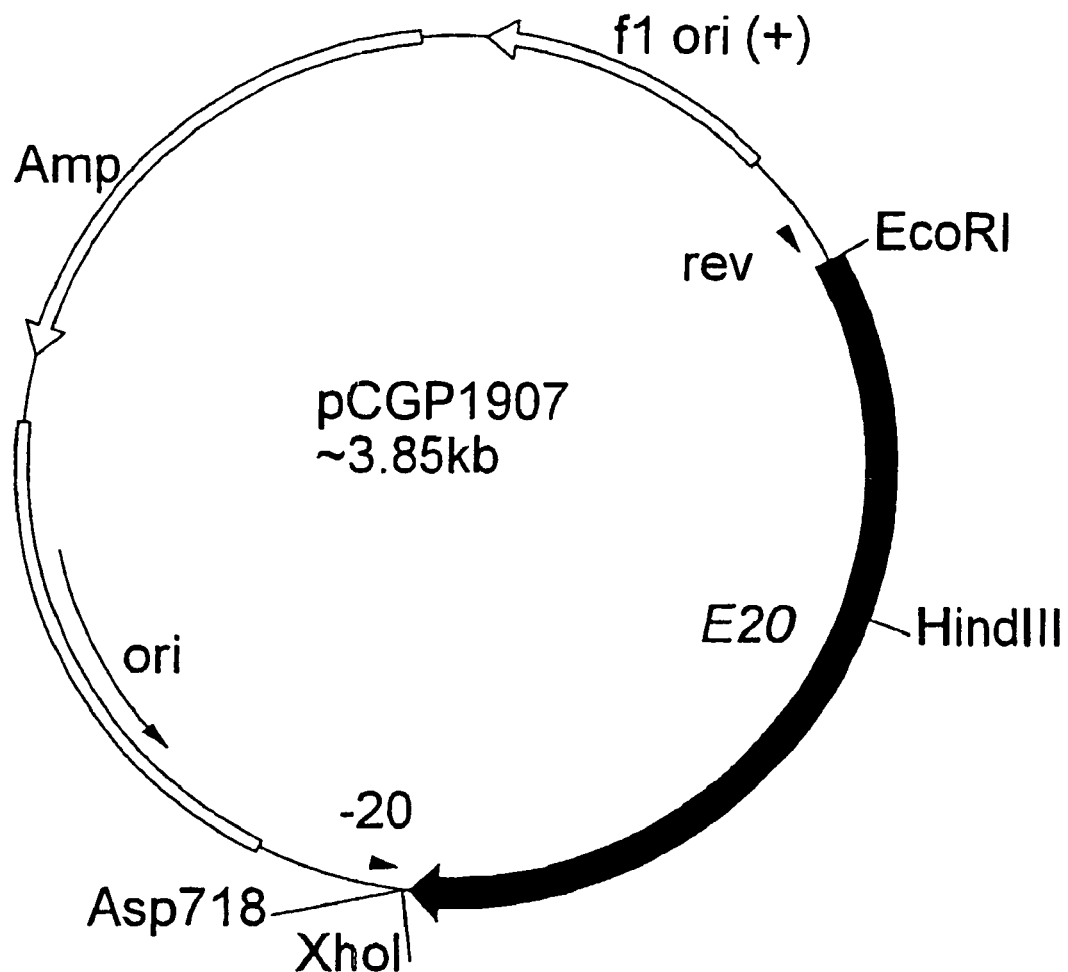
FIG. 3 is a diagrammatic representation of the plasmid pCGP1907 containing the E20 cDNA clone from *P. hybrida* cv. OGB. Abbreviations are as follows: Amp=the ampicillin resistance gene which confers resistance to the antibiotic ampicillin, f1 ori (+)=f1 filamentous phage origin of replication, ori=plasmid origin of replication, rev=approximate location of the M13 reverse primer site used in sequence analysis, -20=approximate location of the M13-20 primer site used in sequence analysis. Selected restriction enzyme sites are also marked.
Figure 4:
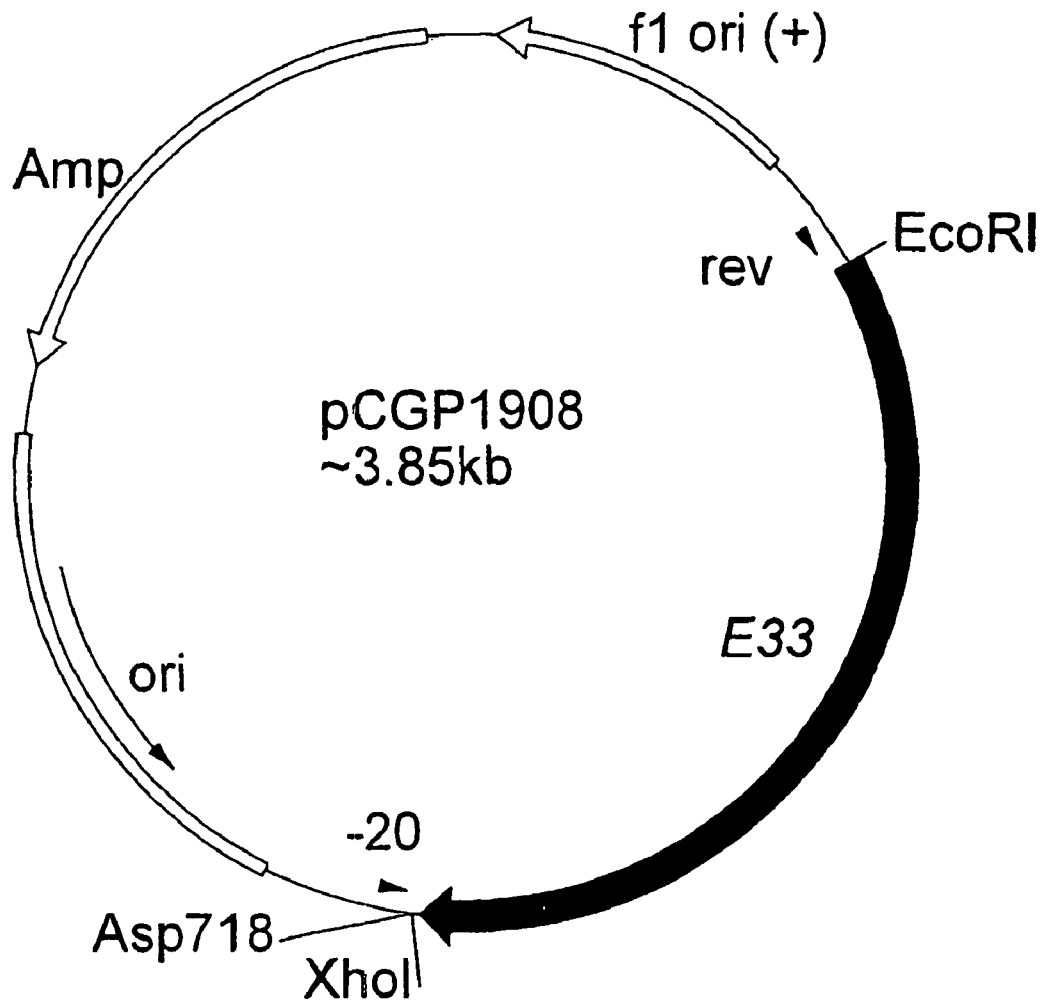
FIG. 4 is a diagrammatic representation of the plasmid pCGP1908 containing the E33 cDNA clone from *P. hybrida* cv. OGB. Abbreviations are as follows: Amp=the ampicillin resistance gene which confers resistance to the antibiotic ampicillin, f1 ori (+) f1 filamentous phage origin of replication, ori=plasmid origin of replication, rev=approximate location of the M13 reverse primer site used in sequence analysis, -20=approximate location of the M13-20 primer site used in sequence analysis. Selected restriction enzyme sites are also marked.

Forty-five hybridizing plaques (designated as E1 to E45) were picked into PSB. These were rescreened to isolate pure clones, using the hybridization conditions as described for the initial screening of the cDNA library. The plasmids contained in the λZAP bacteriophage vector were rescued and sequence data was generated from the 3' and 5' ends of the cDNA inserts. Of these E20 and E33 represented the longest cDNA clones (~1.0 kb and 0.9 kb, respectively) and the plasmids were designated pCGP1907 and pCGP1908 (FIGS. 3 and 4, respectively).

The complete nucleotide sequence of the E20 and E33 cDNA clones (SEQ ID NOs:4 and 6) (contained in pCGP1907 and pCGP1908, respectively) was determined by compilation of sequence generated using commercially available M13 reverse and M13-21 primers along with a specific *Petunia* MT primer 1903F (5'CTT GCT TTG CCA GAA GAT GG 3') [SEQ ID NO:8]. The E20 cDNA clone was 888 bp in length and contained a putative open reading frame of 789 bases which encoded a putative polypeptide of 263 amino acids (SEQ ID NO:5). The E20 sequence was identical to the difE sequence over 822 bp with the E20 cDNA clone having an extra 27 bp of 5' untranslated sequence and a reduction of 96 bp of 3' untranslated sequence as compared to the difE sequence.

The E33 sequence was 1076 bp in length and contained an in-frame stop codon at position 469 (SEQ ID NO:6). The E20 sequence shared 82% identity over 797 bp with the E33 sequence at the nucleotide level. An alignment of the E33 nucleotide sequence with that of the E20 sequence revealed an apparent 2 nucleotide ("CT") deletion in the E33 sequence resulting in an in-frame stop codon. It may be that the E33 clone in the OGB cultivar was derived from a mutated gene. In order to examine the presumed deduced amino acid sequence of the non-mutated gene represented by the E33 clone, 2 nucleotides ("CT") were added to the E33 sequence to produce the E33-corrected nucleotide sequence (SEQ ID NO:26). The deduced amino acid sequence is represented by SEQ ID NO:7. The E33-corrected amino acid sequence shared an 82% identity with the E20 sequence over a 243 amino acid overlap.

A comparison of the translated nucleotide sequence of E20 to sequences in the GenBank database revealed similarity to various caffeoyl-CoA 3-O-methyltransferases. For example, 60% identity over 227 amino acids with Caffeoyl-CoA 3-O-methyltransferase from *Populus kitakamiensis* (Genbank accession number AB000408) and 53% identity over 238 amino acids of a trans-caffeoyl-CoA 3-O-methyltransferase (CCOFMT) (CCOAOMT) from *Petroselinum crispum* (Genbank accession number A40975).

Example 7

Methyltransferase Activity of the *Petunia* FMT (E20) cDNA Clone Expressed in *E. coli*

To confirm whether the *Petunia* E20 cDNA clone encoded a functional FMT it was expressed in an *E. coli* expression system and assayed for FMT activity.

Cloning of E20 into pQE30 *E. coli* Expression Vector (Construction of pCGP3086)

In order to clone the *Petunia* E20 clone (PFMT) into an *E. coli* expression vector, pQE30 (QIAGEN), a BamHI restriction endonuclease site was required at the translation initiating ATG and a PstI restriction endonuclease site was required immediately 3' to the putative stop codon.

The oligonucleotides 1907BamHI F [SEQ ID NO:9] and 1907PstI R (SEQ ID NO:10) (Table 9) were used as primers with pCGP1907 as template to amplify the *Petunia* FMT clone (E20) with a BamHI restriction endonuclease recognition site in place of the initiating AUG and a PstI restriction endonuclease recognition site just after the putative stop codon. PCR conditions included 5 µL 10×PfuTurbo DNA Polymerase buffer (Stratagene), 2 µL 10 mM dNTPs, 2 µL 20 µ/µL 1907BamHI F [SEQ ID NO:9], 2 µL 20 µ/µL 1907PstI R [SEQ ID NO:10], 1 µL 1 µg/µL pCGP1907 template, 37 µL pure water and 1 µL PfuTurbo DNA Polymerase (Stratagene).

The PCR was incubated at 95° C. for 5 minutes, followed by 30 cycles of 94° C. for 30 seconds, 60° C. for 30 seconds and 72° C. for 1 minute and then a final incubation at 72° C. for 10 minutes with subsequent storage at 4° C.

TABLE 9

Oligonucleotides used in the cloning of the E20 cDNA clone into pQE30 bacterial expression vector

| SEQ ID NO: | NAME | SEQUENCE |
|---|---|---|
| 9 | 1907BamHI F | GCAT GGA TCC ACA GGC AAA ACC GCC CAC CCT G |
| 10 | 1907PstI R | GCAT CTG CAG CTA GGA GAG ACG CCT GCA AAG |

Figure 5:
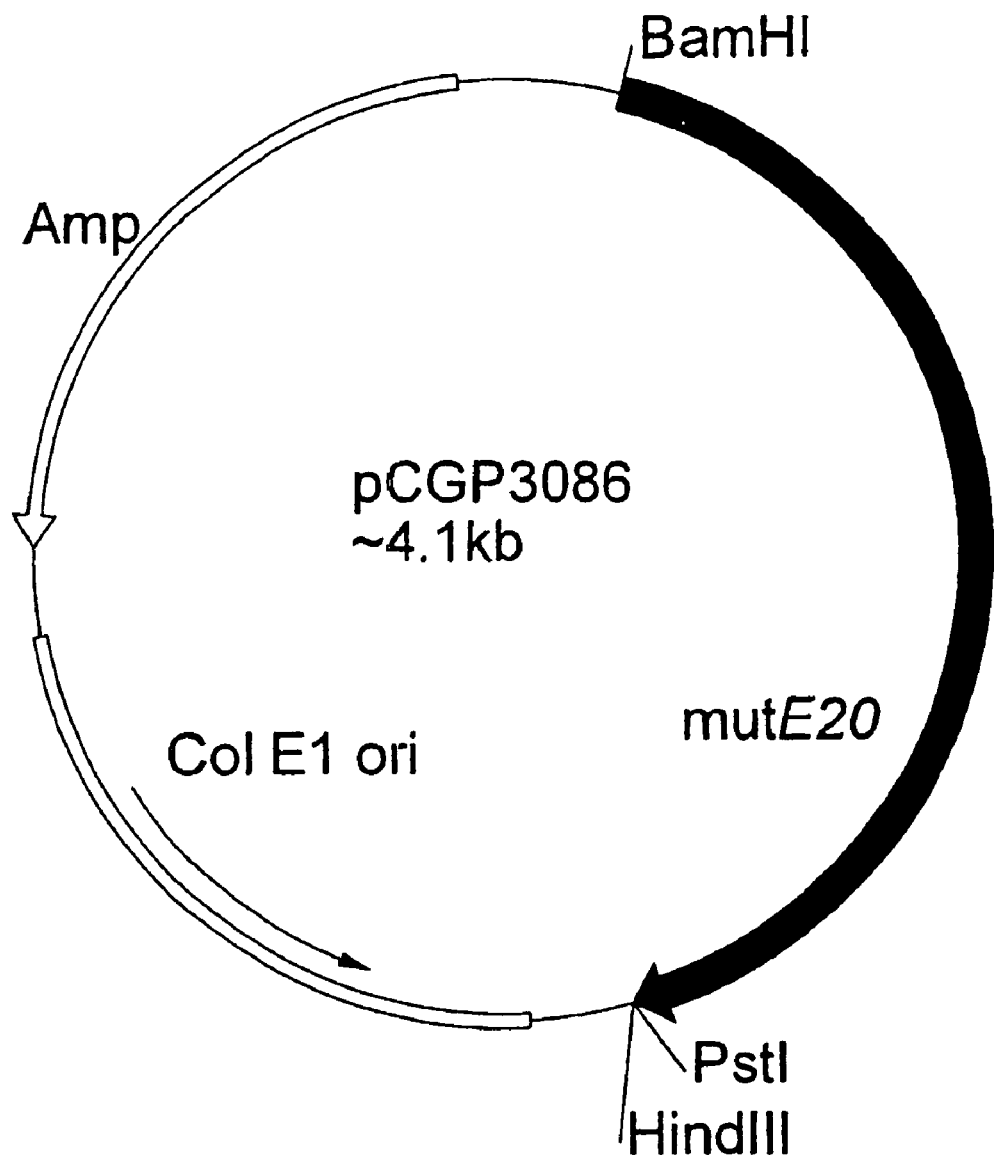
FIG. 5 is a diagrammatic representation of the plasmid pCGP3086 (mut E20 in pQE30) containing the mutated E20 cDNA clone from *P. hybrida* in the bacterial expression vector pQE30. Abbreviations are as follows: Amp=the ampicillin resistance gene which confers resistance to the antibiotic ampicillin, Col E1 ori=*E. coli* plasmid origin of replication. Selected restriction enzyme sites are also marked.

The resulting PCR products were electrophoresed through a 1% w/v agarose gel and a 0.72 kb band was isolated and purified using a QIAEX II Gel Extraction kit (QIAGEN) according to manufacturer's recommendation. The isolated products were then digested the restriction endonuclease PstI. The digestion product was purified using a QIAquick PCR purification kit (QIAGEN) and then digested with the restriction endonuclease BamHI. The BamHI/PstI digested products were finally purified using a QIAquick PCR purification kit (QIAGEN) and subsequently ligated with the BamHI/PstI ends of the pQE30 vector (QIAGEN) using a DNA Ligation Kit (Amersham) according to the manufacturer's recommendations. Transformants were analyzed for the presence of the specific 0.72 kb insert using BamHI/PstI restriction endonuclease digests. The sequence of the insert was confirmed by sequence analysis using a pQE Sequencing-Primer Set (QIAGEN). The resulting plasmid was designated pCGP3086 (mut-E20 in pQE30) (FIG. 5).

As a consequence of using the 1907BamHI F (SEQ ID NO:9) and 1907PstR (SEQ ID NO: 10) oligonucleotides as primers in the PCR and of the subsequent cloning of the product into pQE30, the sequence of the *Petunia* E20 clone was altered around the putative initiating methionine of the encoded polypeptide. As a consequence the expected amino acids around the putative initiating methionine were changed from "M T G K T A H P" (SEQ ID NO:48) to "M R G S H H H H H H G S T G K T A H P" (SEQ ID NO:49).

According to the manufacturer, "the 6×His-tag is much smaller than most other affinity tags and is uncharged at physiological pH. It rarely alters or contributes to protein immunogenicity, rarely interferes with protein structure or function, does not interfere with secretion, does not require removal by protease cleavage, and is compatible with denaturing buffer systems". (QIAGEN website).

For analysis of methyltransferase activity of the E20 clone, pCGP3086 was subsequently introduced into *E. coli* M15 (pREP$_4$) (QIAGEN) cells according to the method of Inoue et al., 1990, supra 10 mL of LB containing ampicillin at 100 µg/mL (LB/Amp100) was inoculated with a single colony of pCGP3086 in M15/pREP$_4$ cells and incubated at 37° C. with shaking for 16 hours. One millilitre of this culture was then used to inoculate 25 mL LB/Amp100. The culture was incubated at 37° C. with shaking for around 2 hours until the Absorbance at 600 nm ($A_{600}$) was between 0.5 to 0.7. IPTG (iso-propyl-β-D-thiogalactoside) was then added to a final concentration of 1 mM and the culture was further incubated at 37° C. with shaking with 1.5 mL aliquots being removed at 0, 1, 2 and 5 hours after addition of IPTG.

The cells contained in each aliquot were subsequently pelleted by centrifugation and then resuspended in 50 μL 8 M urea denaturing buffer (8 M urea, 0.1 M NaH$_2$PO$_4$, 0.01M Tris-HCl, pH8). The lysates were centrifuged at 14,000 rpm for 10 minutes at room temperature to pellet cell debris. The crude protein extracts were denatured by boiling in 10% glycerol, 3% w/v sodium dodecyl sulphate (SDS), 3%, β-mercaptoethanol (BME) and 0.025% bromophenol blue and then electrophoresed through precast SDS PAGE gels (12% resolving, 4% stacking gel) (Ready Gels, BIORAD) in a running buffer made up of 25 mM Tris-HCl, pH 8.3, 192 mM glycine, 0.1% w/v SDS at 120V for 80 min. Standards included prestained Low Range markers (BIORAD) which contained standard protein samples of 116 kDa, 80 kDa, 51.8 kDa and 34.7 kDa.

Proteins were visualized by staining with Coomassie Brilliant Blue (CBB) (0.25% w/v CBB, 45% v/v methanol. 10% v/v acetic acid). A strongly staining band of the size expected for a His-Tag fusion of *Petunia* FMT (E20) protein was detected at 27.5 kDa. Proteins on a duplicate SDS-PAGE gel to that described above were also electro-transferred to Immun-blot PVDF membrane (BIORAD) at 4° C. in a buffer of 25 mM Tris-HCl pH 8.3, 20% methanol and 192 mM glycine at 100V for 60 min. The presence of the His-tag fused to the specific protein encoded by the E20 cDNA clone in pCGP3086 was confirmed by detection with a Ni-NTA-AP conjugate (QIAGEN) according to the manufacturer's instructions. A strongly staining protein band estimated to be 27.5 kDa was detected confirming the presence and high level expression of the recombinant E20 protein. No bands were visible in a pQE30 control under these detection conditions.

Preparation of Crude Protein Extracts 10 mLs of LB containing ampicillin at 100 μg/mL and kanamycin at 25 μg/mL. (LB/Amp100+Kan25) were inoculated with a single colony of pCGP3086 or pQE30 in M15 (pREP$_4$) cells. The culture was incubated at 30° C. with shaking for 16 hours. 2.5 mL of this culture was then added to 25 mL fresh LB/Amp100+Kan25 and the freshly inoculated culture was incubated at 30° C. with shaking until an A$_{600}$ of 0.5 to 0.7 was reached. IPTG was then added to a final concentration of 1 mM and the culture was further incubated at 30° C. with shaking for 8 hours. The cells were pelleted by centrifugation at 3500 rpm for 10 minutes at 4° C. The pellet was resuspended in 1 mL of 0.1 M NaPi, pH 7.5, 4 mM MgCl$_2$. Freshly prepared lysozyme was then added to a final concentration of 1 mg/mL and the mixture was incubated on ice for 30 minutes. The mixture was then sonicated for two bursts of 10 seconds at output 2-3 and then incubated on ice for 30 minutes. The cell debris was pelleted by centrifugation at 14,000 rpm for 20 minutes at 4° C. The supernatant was passed through a NAP-10 column (Pharmacia) and 1.5 mL of the sample collected in 0.1 M NaPi, pH 7.5, 4 mM MgCl$_2$.

Methyltransferase Activity

The enzyme activity of the *Petunia* E20 clone contained in pCGP3086 was initially assessed using the substrates delphinidin 3-glucoside and delphinidin 3-rutinoside under assay conditions as described in Jonsson et al. (1983), supra.

Methyltransferase assays were set up according to Table 10 in a total reaction volume of 50 μL.

TABLE 10

Composition of methyltransferase assays using crude homogenates from bacterial cultures containing the plasmids pCGP3086 (E20) or pQE30 (control).

| # | Plasmid | Crude homogenate (μL) | 3 mg/mL D3R (μL) | 3 mg/mL D3G (μL) | $^{14}$C-SAM (μL) | Buffer (μL) |
|---|---------|------------------------|-------------------|-------------------|---------------------|-------------|
| 1 | pQE30 | 20 | 5 | 0 | 5 | 20 |
| 2 | pQE30 | 20 | — | 5 | 5 | 20 |
| 3 | pQE30 | 20 | 5 | 0 | 0 | 25 |
| 4 | pQE30 | 20 | 0 | 5 | 0 | 25 |
| 5 | pQE30 | 20 | 0 | 0 | 5 | 25 |
| 6 | none | 0 | 5 | 0 | 5 | 40 |
| 7 | none | 0 | 0 | 5 | 5 | 40 |
| 8 | pCGP3086 | 20 | 5 | 0 | 5 | 20 |
| 9 | pCGP3086 | 20 | — | 5 | 5 | 20 |
| 10 | pCGP3086 | 20 | 5 | 0 | 0 | 25 |
| 11 | pCGP3086 | 20 | 0 | 5 | 0 | 25 |

# = tube number,
D3G = delphinidin 3-glucoside,
D3R = delphinidin 3-rutinoside,
$^{14}$C-SAM = 0.6 M $^{14}$C-SAM (13 μCi/μmol) (Amersham Pharmacia),
Buffer = 0.1 M NaPi, pH 7.5, 4 mM MgCl$_2$ The assay reactions were incubated at 30° C. for 30 minutes. Fifty microlitres of a chloroform mix (CHCl$_3$:methanol/ 1% HCl, 2:1) was added and the mixture was then vortexed to stop the reactions. The phases were separated by centrifugation at 13,000 rpm for 5 minutes and 50 μL of the upper phase was transferred into a clean tube and the contents subsequently hydrolysed by the addition of 12.5 μL of 10M HCl. The tube was then placed in a boiling waterbath for 30 minutes and the contents subsequently desiccated under vacuum. The residue was resuspended in 2-3 μL of methanol/1% HCl and spotted onto a TLC plate alongside standard samples of petunidin, malvidin and delphinidin. The anthocyanidins were separated in a Forestal system (HOAc:water:HCl; 30:10:3) (Markham, *Techniques of flavonoid identification*, Academic Press, London, 1982) and the TLC was exposed to an autoradiographic film (Kodak) for 16 hours at −70° C.

TABLE 11

Results of methyltransferase assays of extracts of *E. coli* containing pCGP3086 or pQE30 control vector using delphinidin 3-glucoside or delphinidin 3-rutinoside as substrate and $^{14}$C-SAM as methyl donor

| # | Plasmid | Crude homogenate | D3R | D3G | $^{14}$C-SAM | Petunidin | Malvidin |
|---|---------|------------------|-----|-----|---------------|-----------|----------|
| 1 | pQE30 | + | + | − | + | no | no |
| 2 | pQE30 | + | − | + | + | no | no |
| 3 | pQE30 | + | + | − | − | no | no |
| 4 | pQE30 | + | − | + | − | no | no |
| 5 | pQE30 | + | − | − | + | no | no |
| 6 | none | − | + | − | + | no | no |

TABLE 11-continued

Results of methyltransferase assays of extracts of *E. coli*
containing pCGP3086 or pQE30 control vector using
delphinidin 3-glucoside or delphinidin 3-rutinoside
as substrate and $^{14}$C-SAM as methyl donor

| # | Plasmid | Crude homogenate | D3R | D3G | $^{14}$C-SAM | Petunidin | Malvidin |
|---|---------|------------------|-----|-----|--------------|-----------|----------|
| 7 | none | − | − | + | + | no | no |
| 8 | pCGP3086 | + | + | − | + | yes | yes |
| 9 | pCGP3086 | + | − | + | + | yes | yes |
| 10 | pCGP3086 | + | + | − | − | no | no |
| 11 | pCGP3086 | + | − | + | − | no | no |

\# = tube number,
D3G = delphinidin 3-glucoside,
D3R = delphinidin 3-rutinoside,
$^{14}$C-SAM = $^{14}$C-labelled S-adenosyl-L-methionine (Amersham Biosciences),
+ = present in reaction mix
− = absent from reaction mix
yes = detection of product on TLC,
no = no reaction observed as determined by absence of product.

Petunidin and malvidin, the methylated derivatives of delphinidin, were detected in assay reactions using crude homogenates from pCGP3086 cells along with the substrates D3R or D3G (Tubes 8 and 9, Table 11). There was no detectable production of petunidin and malvidin in assay reactions using crude homogenates from pQE30 cells (Tubes 1 to 5, Table 11) or having no crude homogenates added (Tubes 6 and 7, Table 11) or in assay reactions without the addition of $^{14}$C-SAM (Tubes 10 and 11, Table 11). The results obtained with expression of the E20 cDNA clone in an *E. coli* expression system provide further evidence to suggest that the E20 cDNA clone from *Petunia* codes for an FMT that is able to methylate delphinidin 3-glucoside and delphinidin 3-rutinoside using SAM as a methyl donor to produce the 3'-methylated derivative, petunidin and the 3' 5'-methylated derivative, malvidin.

Example 8

Antisense Expression of FMT in Plants

The *Petunia* FMT clones (E20 and E33) were each cloned in an antisense orientation behind a Mac promoter (Comai et al., 1990, supra) and introduced into purple flowered VR petunia hybrid line.

Construction of pCGP40

Plasmid pCGP40 was constructed by removing the GUS gene (Jefferson et al., *EMBO J.* 6(13): 3901-3907, 1987) as a BamHI-SacI restriction endonuclease fragment from pCGN7334 and replacing it with the BamHI-SacI restriction endonuclease fragment from pBluescribe M13⁻ that includes the multi-cloning site. Plasmid pCGN7334, obtained from Calgene Inc. (CA, USA), was constructed by inserting the fragment containing the Mac: GUS: mas 3' gene fusion into the XhoI restriction endonuclease site of pCGN7329 (Comai et al., *Plant Molecular Biology* 15: 373-381, 1990).

Construction of pCGP1910 and pCGP1911

Plasmids pCGP1910 and pCGP1911 were constructed by cloning the respective cDNA inserts from pCGP1967 and pCGP1908 (FIGS. 3 and 4) in an antisense orientation behind the Mac promoter (Comai et al., 1990, supra) of pCGP40. The GUS coding region in pCGP40 was removed by digestion with SacI/Asp718 restriction endonucleases. The vector containing the Mac promoter and mas terminator was purified using GeneClean Kit (Bresatec) and ligated with SacI/Asp718 restriction endonuclease ends of the *Petunia* E20 and E33 cDNA fragments released from pCGP1907 and pCGP1908 respectively. Correct insertion of the E20 and E33 inserts in pCGP1910 and pCGP1911 was established by SacI/Asp718 restriction endonuclease analysis of DNA isolated from chloramphenicol-resistant transformants.

Figure 6:
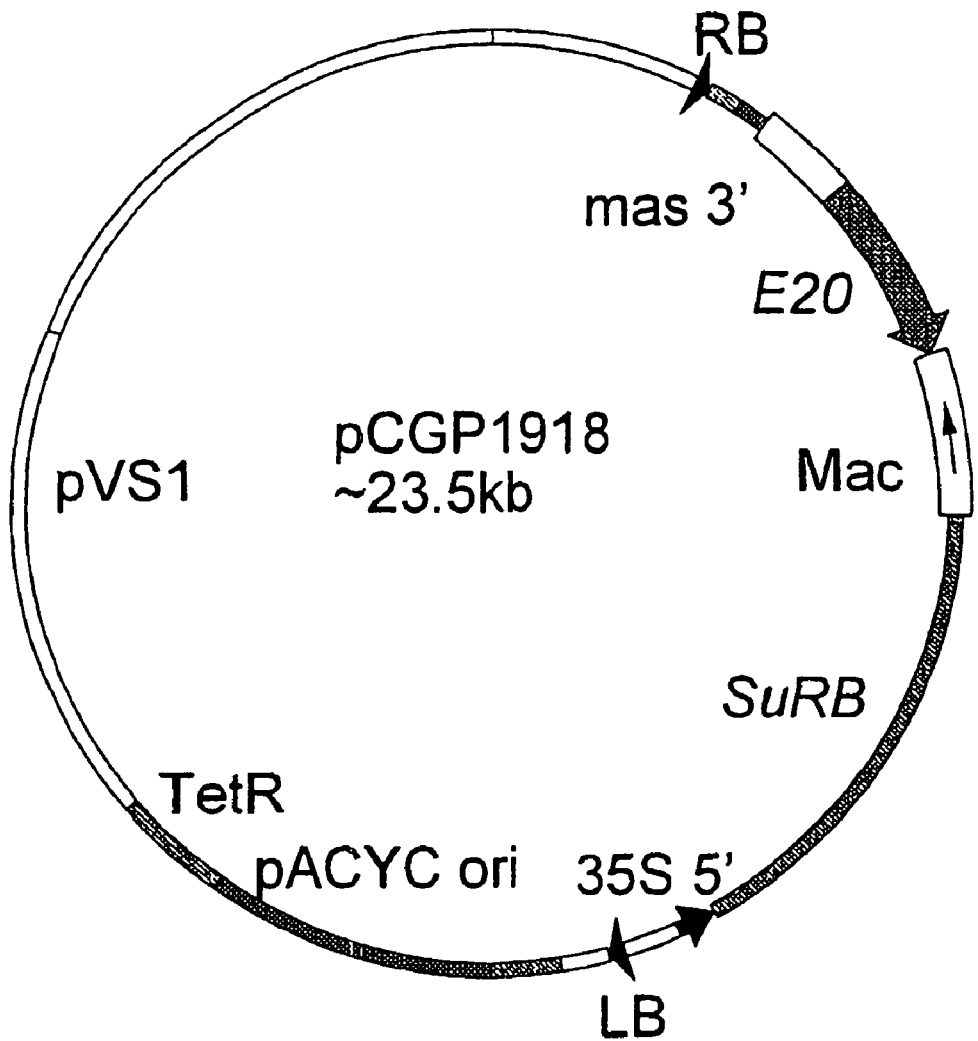
FIG. 6 is a diagrammatic representation of the binary plasmid pCGP1918. The chimaeric antisense E20 gene from pCGP1910 was cloned into the binary vector pWTT2132 (DNAP) in a tandem orientation with the chimaeric SuRB gene. Abbreviations are as follows: TetR=tetracycline resistance gene which confers resistance to the antibiotic tetracycline; LB=left border; RB=right border; SuRB=the coding region and terminator sequence from the acetolactate synthase gene from tobacco; 35S=the promoter region from the cauliflower mosaic virus (CaMV) 35S gene, Mac=Hybrid promoter consisting of the promoter from the mas gene and a CaMV 35S enhancer region, mas 3'=the terminator region from the mannopine synthase gene of *Agrobacterium*; pVS1=a broad host range origin of replication from a plasmid from *Pseudomonas aeruginosa*, pACYC ori=modified replicon from pACYC184 from *E. coli*. Selected restriction enzyme sites are also marked.
Figure 7:
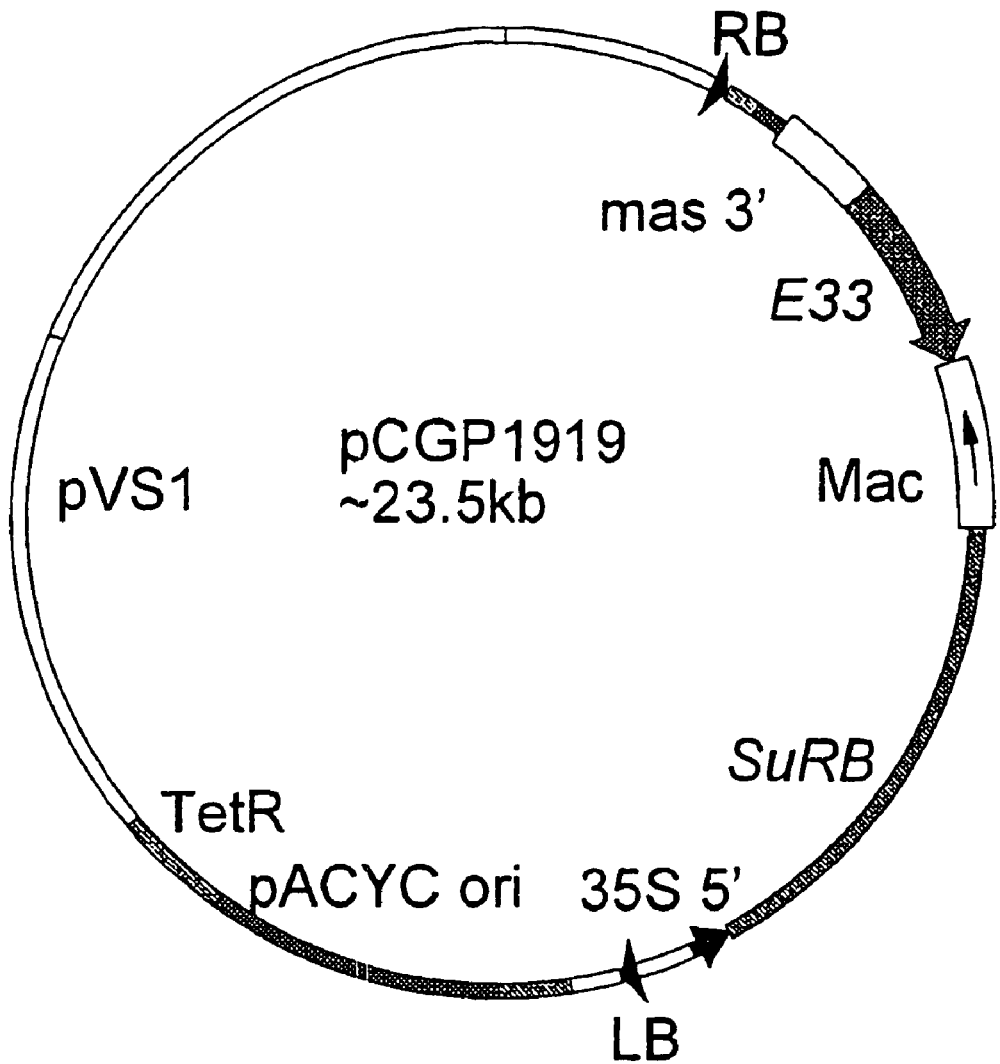
FIG. 7 is a diagrammatic representation of the binary plasmid pCGP1919. The chimaeric antisense E33 gene from pCGP1911 was cloned into the binary vector pWTT2132 (DNAP) in a tandem orientation with the chimaeric SuRB gene; Abbreviations are as follows: TetR=the tetracycline resistance gene which confers resistance to the antibiotic tetracycline; LB=left border; RB=right border; SuRB=the coding region and terminator sequence from the acetolactate synthase gene from tobacco; 35S=the promoter region from the CaMV 35S gene, Mac=Hybrid promoter consisting of the promoter from the mas gene and a CaMV 35S enhancer region, mas 3'=the terminator region from the mannopine synthase gene of *Agrobacterium*; pVS1=a broad host range origin of replication from a plasmid from *Pseudomonas aeruginosa*, pACYC ori=modified replicon from pACYC184 from *E. coli*. Selected restriction enzyme sites are also marked.

Plasmids pCGP1918 (FIG. 6) and pCGP1919 (FIG. 7) were constructed by cloning the respective Mac.*Petunia* E20: mas 3' and the Mac: *Petunia* E33: mas 3' expression cassettes from the plasmids pCGP1910 and pCGP1911 into the Ti binary vector pWTT2132 (DNAP). The *Petunia* E20 and E33 chimaeric genes were isolated from pCGP1910 and pCGP1911 upon restriction endonuclease digestion of the plasmid with BglII and the resulting 5' overhang was repaired using the Klenow fragment of DNA polymerase I. The *Petunia* E20 and E33 chimaeric genes were purified using a Bresaclean Kit (Bresatec) and then ligated with dephosphorylated SmaI ends of the binary vector pWTT2132. Correct ligation of the fragments was established by restriction endonuclease digestion of plasmid DNA isolated from tetracycline resistant *E. coli* transformants. The resulting plasmids were designated pCGP1918 (FIG. 6) and pCGP1919 (FIG. 7), respectively.

Antisense Suppression of FMT Activity in *P. hybrida*

The plasmids pCGP1918 (FIG. 6) and pCGP1919 (FIG. 7) were each introduced into the *Agrobacterium tumefaciens* strain AGL0 separately. The T-DNA contained in the plasmids pCGP1918 (FIG. 6) and in pCGP1919 (FIG. 7) were introduced in separate experiments into *P. hybrida* cv. VR via *Agrobacterium*-mediated transformation.

Transgenic Analysis of pCGP1918/VR and pCGP1919/VR *Petunia* Plants

Independent transgenic plants were produced and grown to flowering. A selection of plants produced flowers with dark pink colors, which differed to the purple colored VR control. A selection of flower colors observed is shown in Table 12. The pigments accumulating in the flowers of the transgenic plants were analyzed by HPLC (Table 13).

TABLE 12

Petal colors of VR, 1918/VR and 1919/VR transgenic flowers

| ACCESSION NUMBER | CULTIVAR/ CONSTRUCT | RHSCC CODE | PETAL COLOR |
|---|---|---|---|
| 9339 | VR/1918 | 64C, 67A | dark pink |
| 9724 | VR/1918 | 64B, 67A | dark pink |
| 10161 | VR/1918 | 78A | purple |
| 10167 | VR/1918 | 78A | purple |
| 10169 | VR/1918 | 78A | purple |
| 10171 | VR/1918 | 78A | purple |
| 9349 | VR/1919 | 78A | purple |
| 9463 | VR/1919 | 78A | purple |
| 10177 | VR/1919 | 74A | red/purple |
| 10178 | VR/1919 | 78A | purple |
| 10183 | VR/1919 | 78A | purple |
| 12704 | VR control | 78A | purple |

RHSCC = Royal Horticultural Society Color Chart (Kew, UK).

Extraction of Anthocyanidins

Prior to HPLC analysis, the anthocyanin and flavonol molecules present in petal and stamen extracts were acid hydrolyzed to remove glycosyl moieties from the anthocyanidin or flavonol core. Anthocyanidin and flavonol standards were used to help identify the compounds present in the floral extracts.

Anthocyanidins in the reaction mixture were analysed by HPLC via gradient elution using gradient conditions of 50% B to 60% B over 10 minutes, then 60% B for 10 minutes and finally 60% B to 100% B over 5 minutes where solvent A consisted of TFA:$H_2O$ (5:995) and solvent B consisted of acetonitrile:TFA:$H_2O$ (500:5:495). An Asahi Pac ODP-50 cartridge column (250 mm×4.6 mm ID) was used for the reversed phase chromatographic separations. The flow rate was 1 mL/min and the temperature was 40° C. The detection of the anthocyanidin compounds was carried out using a Shimadzu SPD-M6A three dimensional detector at 400-650 nm.

The anthocyanidin peaks were identified by reference to known standards, viz delphinidin, petunidin, malvidin, cyanidin and peonidin

TABLE 13

Percentage levels of anthocyanidins detected in the petals of VR/1918 and VR/1919 transgenics by HPLC analysis

| | | | Anthocyanidin (%) | | | | |
|---|---|---|---|---|---|---|---|
| Acc# | pCGP# | Color | Del | Cya | Pet | Peo | Mal |
| 9724 | 1918 | dark pink | 51.7 | 6.0 | 34.5 | 0.0 | 7.8 |
| 10161 | 1918 | purple | 1.2 | 0.6 | 0.6 | 0.3 | 97.3 |
| 10167 | 1918 | purple | 0.6 | 0.2 | 4.7 | 0.3 | 94.2 |
| 10169 | 1918 | purple | 0.4 | 0.1 | 4.7 | 0.3 | 94.4 |
| 10171 | 1918 | purple | 0.5 | 0.1 | 5.4 | 0.3 | 93.7 |
| 9349 | 1919 | purple | 0.6 | 0.0 | 5.6 | 0.2 | 93.6 |
| 9463 | 1919 | purple | 0.8 | 0.1 | 7.9 | 0.3 | 90.9 |
| 10177 | 1919 | red-purple | 36.8 | 0.0 | 38.7 | 0.0 | 24.5 |
| 10178 | 1919 | purple | 1.2 | 0.0 | 14.5 | 0.2 | 84.1 |
| 10183 | 1919 | purple | 0.5 | 0.0 | 4.4 | 0.3 | 94.8 |
| 12704 | VR control | purple | 0.3 | 0.0 | 3.8 | 15.7 | 80.1 |

Acc# = Accession number of plant,
pCGP# = Plasmid number,
Del = Delphinidin, expressed as a percentage of total anthocyanidins detected,
Cya = Cyanidin, expressed as a percentage of total anthocyanidins detected,
Pet = Petunidin, expressed as a percentage of total anthocyanidins detected,
Peo = Peonidin, expressed as a percentage of total anthocyanidins detected,
Mal = Malvidin, expressed as a percentage of total anthocyanidins detected Antisense expression of *Petunia* E20 (in pCGP1918) and E33 (in pCGP1919) led to a change in flower color from purple to dark pink or red-purple with a concomitant change in the anthocyanin composition. In general, VR control petunia flowers predominantly accumulate malvidin (the 3',5' methylated derivative of delphinidin) (around 80% of total anthocyanidin) (Table 13). The transgenic line 9724 containing the antisense *Petunia* E20 gene produced flowers with a dark pink color with the predominant anthocyanin being delphinidin suggesting that the expression of the antisense E20 gene has impacted upon a 3'5' methyltransferase activity. The transgenic line 10177 containing the antisense *Petunia* E33 gene produced flowers with a red-purple color with the predominant anthocyanins being delphinidin and petunidin suggesting that the expression of the antisense E33 gene has also impacted upon a 3'5' methyltransferase activity.

Example 9

Isolation of FMT cDNA Clone from *Torenia*

Preparation of a *Torenia* Petal cDNA Library

A λZAPII (EcoRI/XhoI directional) kit (Stratagene) was used to prepare a cDNA library from RNA isolated from petals of opening buds of *Torenia hybrida*. cv. Summerwave (Suntory Ltd.) according to the conditions recommended by the manufacturer.

Figure 8:
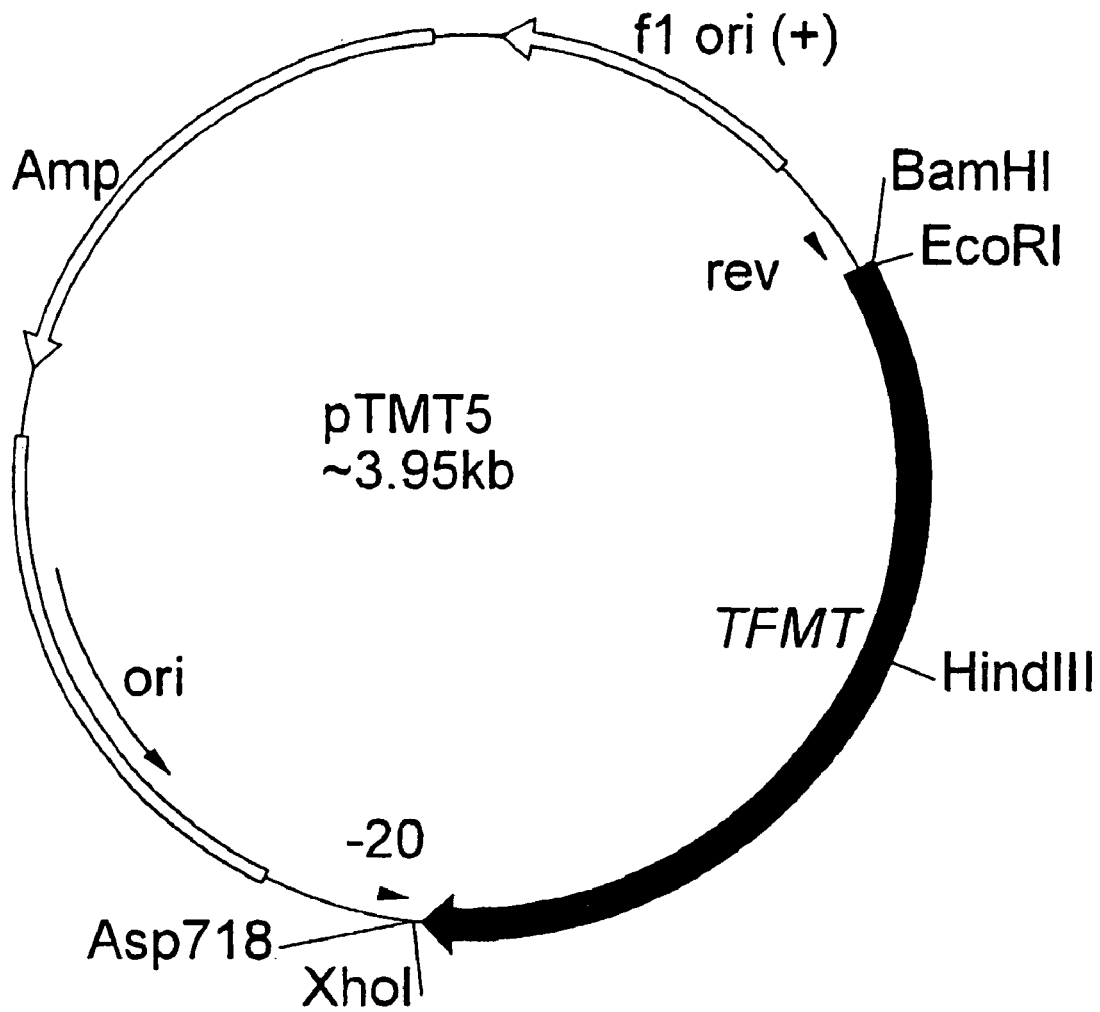
FIG. 8 is a diagrammatic representation of the plasmid pTMT5 containing the TFMT cDNA clone from *Torenia*. Abbreviations are as follows: Amp=the ampicillin resistance gene which confers resistance to the antibiotic ampicillin, f1 ori (+)=f1 filamentous phage origin of replication, ori=plasmid origin of replication, rev=approximate location of the M13 reverse primer site used in sequence analysis, -20=approximate location of the M13-20 primer site used in sequence analysis. Selected restriction enzyme sites are also marked.

About 200,000 pfus were screened with DIG-labelled *Petunia* FMT (E20) cDNA clone from pCGP1907 (FIG. 3) using low stringency conditions as described by Tanaka et al., (*Plant Cell Physiol* 37: 711-716, 1996). Twenty hybridizing plaques were picked into PSB. They were rescreened to isolate purified plaques, using the hybridization conditions as described for the initial screening of the cDNA library. The plasmids contained in the λZAPII bacteriophage vector were rescued and sequence data was generated from the 3' and 5' ends of the cDNA inserts. Of these TFMT represented the longest cDNA clone (~1 kb) and the plasmid was designated as pTMT5 (FIG. 8).

The complete sequence of the *Torenia* FMT cDNA clone (TFMT) [SEQ ID NO:11] was determined by compilation of sequence from different pUC18 subclones obtained using standard procedures for the generation of randomly-overlapping clones (Sambrook et al., 1989, supra). The sequence was determined to be 1012 bases in length and contains an open reading frame that encodes a putative polypeptide of 240 amino acids [SEQ ID NO:12]. The TFMT clone shared 50% identity with the *Petunia* E20 sequence [SEQ ID NO:4] at the nucleotide level and 51% identity with the *Petunia* E33 sequence [SEQ ID NO:6 and SEQ ID NO:26]. The deduced amino acid sequence of the *Torenia* FMT clone (TFMT) shared 56% identity and 70% similarity at the amino acid level with that of the *Petunia* FMT (E20) clone [SEQ ID NO: 5]. The deduced amino acid sequence of the *Torenia* FMT clone (TFMT) shared 69% identity and 82% similarity at the amino acid level with that of the *Petunia* FMT (E33-corrected) clone [SEQ ID NO: 7].

Methyltransferase Activity of the *Torenia* FMT cDNA Clone Expressed in *E. coli*

The *Torenia* FMT cDNA clone (TFMT) was also expressed in an *E. coli* expression system (analogous to that used in Example 7) and assayed for FMT activity.

Cloning of *Torenia* FMT into pQE30 *E. coli* Expression Vector (Construction of pCGP3090)

In order to clone the *Torenia* FMT cDNA clone into an *E. coli* expression vector, pQE30 (QIAGEN), a BamHI restriction endonuclease site was required at the translation initiating ATG and a PstI restriction endonuclease site was required immediately 3' to the putative stop codon.

The oligonucleotides TMT5.BamHI.F [SEQ ID NO:13] and TMT5.PstI.R [SEQ ID NO:14] (Table 14) were used as primers with pTMT5 as template to amplify the *Torenia* FMT cDNA clone with a BamHI restriction endonuclease recognition site in place of the initiating AUG and a PstI restriction endonuclease recognition site immediately 3' to the putative stop codon.

PCR conditions included 5 μL 10×PfuTurbo DNA Polymerase buffer (Stratagene), 2 μL 10 mM dNTPs, 2 μL 20 μ/μL TMT5.BamHI.F [SEQ ID NO:13], 2 μL 20 μ/μL TMT5.PstI.R [SEQ ID NO:14], 1 μL 1 μg/μL pTMT5 template, 37 μL pure water and 1 μL PfuTurbo DNA Polymerase (Stratagene). The PCR was incubated at 95° C. for 5 minutes, followed by 30 cycles of 94° C. for 30 seconds, 60° C. for 30 seconds and 72° C. for 1 minute and then a final incubation at 72° C. for 10 minutes with subsequent storage at 4° C.

TABLE 14

Oligonucleotides used in the cloning of the TFMT cDNA clone into pQE30 bacterial expression vector

| SEQ ID NO: | PRIMER | SEQUENCE (5' to 3') |
|---|---|---|
| 13 | TMT5.BamHI.F | GCA TGG ATC CAA AGA TAA GTT CTA TGG CAC CAT TTT G |
| 14 | TMT5.PstI.R | GCA TCT GCA GTT ATT TGA GAC GTT TGC ACA AGG TG |

Figure 9:
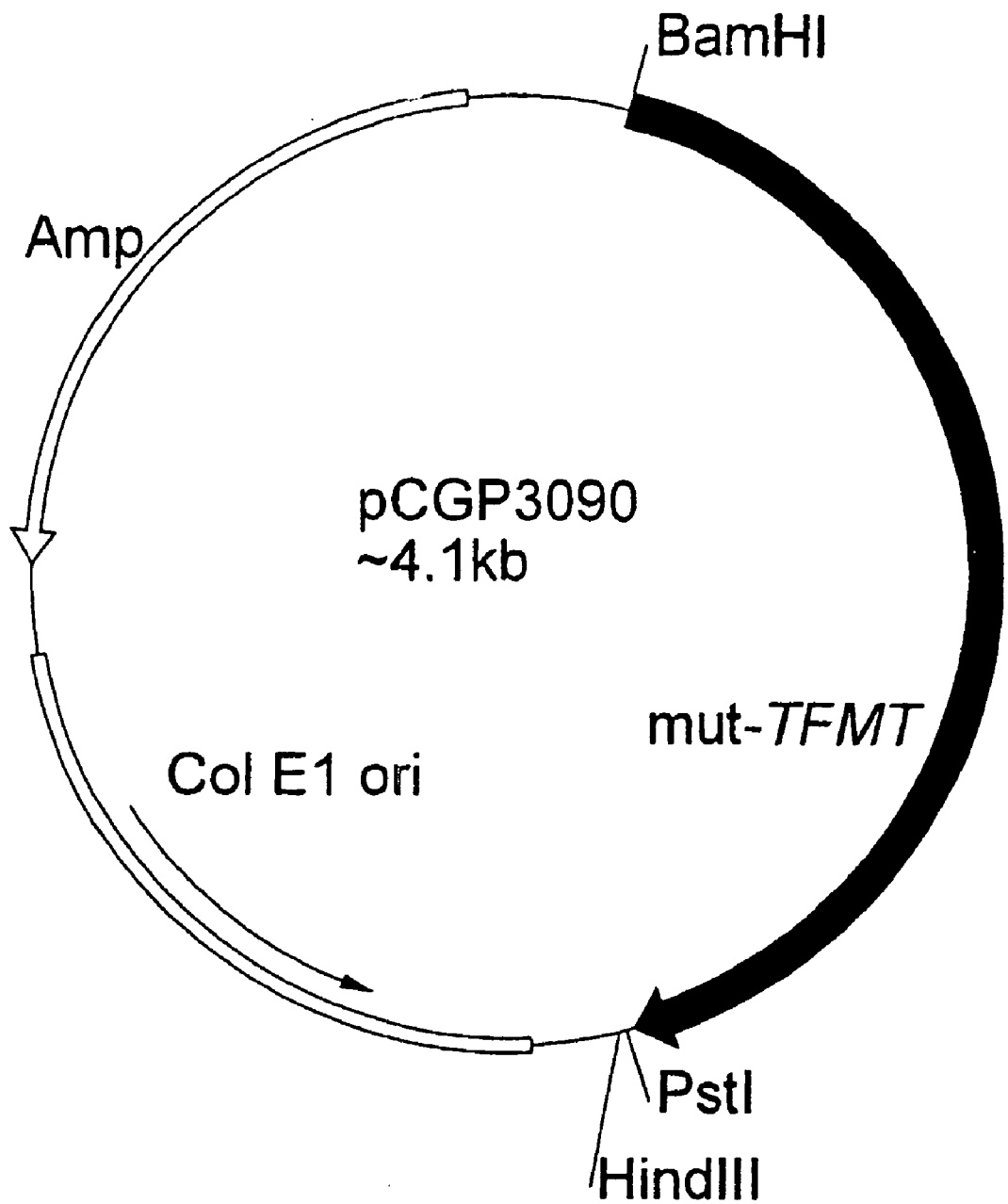
FIG. 9 is a diagrammatic representation of the plasmid pCGP3090 (mut TFMT in pQE30) containing the mutated TFMT cDNA clone from *Torenia* in the bacterial expression vector pQE30. Abbreviations are as follows: Amp=the ampicillin resistance gene which confers resistance to the antibiotic ampicillin, Col E1 ori=*E. coli* plasmid origin of replication. Selected restriction enzyme sites are also marked.

The resulting PCR products were electrophoresed through a 1% w/v agarose gel and a 0.72 kb band was isolated and purified using a QIAEX II Gel Extraction kit (QIAGEN) according to manufacturer's recommendation. The isolated products were then digested with the restriction endonuclease PstI. The digestion product was purified using a QIAquick PCR purification kit (QIAGEN) and then digested with the restriction endonuclease BamHI. The BamHI/PstI digested products were finally purified using a QIAquick PCR purification kit (QIAGEN) and subsequently ligated with the BamHI/PstI ends of the pQE30 vector (QIAGEN) using DNA Ligation Kit (Amersham) according to the manufacturer's recommendations. Transformants were analyzed for the presence of the specific 0.72 kb insert using BamHI/PstI restriction endonuclease digests. The sequence of the insert was confirmed by sequence analysis using pQE Sequencing-Primer Set (QIAGEN). The resulting plasmid was designated pCGP3090 (mut-TFMT in pQE30) (FIG. 9).

As a consequence of using the TMT5.BamHI.F (SEQ ID NO: 13) and TMT5.PstI.R (SEQ ID NO: 14) oligonucleotides as primers in the PCR and of the subsequent cloning of the product into pQE30, the sequence of the *Torenia* FMT clone was altered around the putative initiating methionine of the encoded polypeptide. As a consequence the expected amino acids around the putative initiating methionine were changed from "M K D K F Y G T" (SEQ ID NO: 50) to "M R G S H H H H H H G S K D K F Y G T" (SEQ ID NO: 51).

For analysis of methyltransferase activity of the *Torenia* FMT, the plasmid pCGP3090 was subsequently introduced into *E. coli* M15 (pREP4) (QIAGEN) cells according to the method of Inoue et al., 1990, supra.

The confirmation of recombinant protein expression and preparation of crude protein extracts and subsequent determination of methyltransferase activity were as described for the analysis of the *Petunia* E20 cDNA clone (PFMT) (described above in Example 7).

The enzyme activities of the protein encoded by the *Torenia* FMT cDNA clone in pCGP3090 along with that of the *Petunia* FMT (E20) clone in pCGP3086 were assessed using the substrates delphinidin 3-glucoside and delphinidin 3-rutinoside under assay conditions as described in Jonsson et al. (1983), supra and in Example 7 of this specification.

Methyltransferase assays were set up according to Table 15 in a total reaction volume of 50 μL.

TABLE 15

Composition of methyltransferase assays using crude homogenates from bacterial cultures containing the plasmids pCGP3086 (PFMT) or pCGP3090 (TFMT) or pQE30 (control)

| # | Plasmid | Crude homogenate (μL) | 3 mg/mL D3R (μL) | 3 mg/mL D3G (μL) | SAM (μL) | Buffer (μL) |
|---|---|---|---|---|---|---|
| 1 | pQE30 | 20 | 5 | 0 | 5 | 20 |
| 2 | pQE30 | 20 | 0 | 5 | 5 | 20 |
| 3 | pQE30 | 20 | 5 | 0 | 0 | 25 |
| 4 | pQE30 | 20 | 0 | 5 | — | 25 |
| 5 | pQE30 | 20 | 0 | — | 5 | 25 |
| 6 | none | 0 | 5 | 0 | 5 | 40 |
| 7 | none | 0 | 0 | 5 | 5 | 40 |
| 8 | pCGP3086 | 20 | 5 | 0 | 5 | 20 |
| 9 | pCGP3086 | 20 | 0 | 5 | 5 | 20 |
| 10 | pCGP3086 | 20 | 5 | 0 | 0 | 25 |
| 11 | pCGP3086 | 20 | 0 | 5 | 0 | 25 |
| 12 | pCGP3090 | 20 | 0 | 5 | 5 | 20 |
| 13 | pCGP3090 | 20 | 0 | 5 | 0 | 25 |

# = tube number,
D3G = delphinidin 3-glucoside,
D3R = delphinidin 3-rutinoside,
$^{14}$C-SAM = 0.6 mM $^{14}$C-SAM (13 μCi/μmol) (Amersham Pharmacia),
Buffer = 0.1 M NaPi, pH 7.5, 4 mM MgCl$_2$ Reaction conditions were as described previously (Example 7).

TABLE 16

Results of methyltransferase assays of extracts of *E. coli* containing pCGP3086, pCGP3090 or pQE30 control vector using delphinidin 3-glucoside or delphinidin 3-rutinoside as substrate $^{14}$C-SAM as methyl donor

| # | Plasmid | Crude homogenate | D3R | D3G | SAM | Petunidin | Malvidin |
|---|---|---|---|---|---|---|---|
| 1 | pQE30 | + | + | − | + | no | no |
| 2 | pQE30 | + | − | + | + | no | no |
| 3 | pQE30 | + | + | − | − | no | no |
| 4 | pQE30 | + | − | + | − | no | no |
| 5 | pQE30 | + | − | − | + | no | no |
| 6 | none | − | + | − | + | no | no |
| 7 | none | − | − | + | + | no | no |
| 8 | pCGP3086 | + | + | − | + | yes | yes |
| 9 | pCGP3086 | + | − | + | + | yes | yes |
| 10 | pCGP3086 | + | + | − | − | no | no |
| 11 | pCGP3086 | + | − | + | − | no | no |
| 12 | pCGP3090 | + | − | + | + | yes | yes |
| 13 | pCGP3090 | + | − | + | − | no | no |

# = Tube number,
D3G = delphinidin 3-glucoside,
D3R = delphinidin 3-rutinoside,
$^{14}$C-SAM = $^{14}$C-labelled S-adenosyl-L-methionine (Amersham Biosciences),
+ = present in reaction mix
− = absent from reaction mix
yes = detection of product on TLC,
no = no reaction observed as determined by absence of product.

Petunidin and malvidin, the methylated derivatives of delphinidin, were detected in assay reactions using crude homogenates from pCGP3090 (containing TFMT) and D3G (Tube 12, Table 15). There was no detectable production of petunidin and malvidin in assay reactions using crude homogenates from pQE30 cells (Tubes 1 to 5, Table 15) or having no crude homogenates added (Tubes 6 and 7, Table 15) or in assay reactions without the addition of $^{14}$C-SAM (Tubes 10, 11 and 13, Table 15). The crude homogenates from pCGP3086 (containing PFMT) were used as positive controls (Tubes 8 and 9, Table 16).

The results obtained with expression of the *Torenia* FMT cDNA clone (TFMT) in an *E. coli* expression system provide further evidence to suggest that the TFMT cDNA clone codes for an FMT that is able to methylate delphinidin 3-glucoside using SAM as a methyl donor to produce the 3'-methylated derivative, petunidin and the 3' 5' methylated derivative, malvidin.

Example 10

HPLC Assay of Methyltransferase Activity of *Petunia* and *Torenia* FMT Clones The enzyme activities of the peptides encoded by *Petunia* and *Torenia* FMT cDNA clones in pCGP3086 and pCGP3090, respectively were further assessed using the substrates delphinidin 3-glucoside and delphinidin 3-rutinoside and delphinidin 3,5-diglucoside under assay conditions as previously described (Table 15, Example 9) except that the $^{14}$C-labelled SAM was replaced with non radioactive SAM at 2 mg/mL and the substrates (delphinidin 3-glucoside and delphinidin 3-rutinoside and delphinidin 3,5-diglucoside) at 2 mg/mL.

TABLE 17

Identification of products (in mg/g) by HPLC from methyltransferase assays of extracts of *E. coli* containing pCGP3086, pCGP3090 or pQE30 control vector using delphinidin 3-glucoside, delphinidin 3-rutinoside and delphinidin 3,5-diglucoside as substrate and SAM as methyl donor

| Tube No. | Substrate | Plasmid | Anthocyanidins (mg/g) | | | | | Predominant FMT Activity |
|---|---|---|---|---|---|---|---|---|
| | | | Del | Cya | Pet | Peo | Mal | |
| 1a | D3R | none | 17.6 | 0.6 | 0 | 0 | 0 | none |
| 1b | | | 19.9 | 0.6 | 0.6 | 0 | 0 | |
| 2a | D3R | pQE30 | 16.9 | 0.6 | 0.6 | 0 | 0 | none |
| 2b | | | 21.9 | 0.6 | 0.6 | 0 | 0 | |
| 3a | D3R | pCGP3086 | 3.7 | 0.4 | 10.2 | 0.2 | 2.9 | 3'FMT |
| 3b | | | 4.5 | 0.5 | 11.9 | 0.2 | 3.6 | |
| 4a | D3R | pCGP3090 | 2.5 | 0 | 0.8 | 0.4 | 15.6 | 3'5'FMT |
| 4b | | | 2.8 | 0 | 0.8 | 0.4 | 15.1 | |
| 5a | D3G | none | 7.8 | 1.7 | 0.9 | 0 | 0 | none |
| 5b | | | 9.8 | 1.9 | 0.9 | 0 | 0 | |
| 6a | D3G | pQE30 | 17.1 | 2.5 | 1.2 | 0 | 0 | none |
| 6b | | | 22.1 | 2.7 | 1.3 | 0 | 0 | |
| 7a | D3G | pCGP3086 | 7.1 | 2.4 | 8.8 | 0.5 | 1.2 | 3'FMT |
| 7b | | | 6.4 | 2.0 | 10.0 | 0.6 | 1.3 | |
| 8a | D3G | pCGP3090 | 1.8 | 1.0 | 1.2 | 2.0 | 17.1 | 3'5'FMT |
| 8b | | | 1.9 | 0.9 | 1.3 | 1.9 | 18.1 | |
| 9a | D3, 5G | none | 4.2 | 0 | 0 | 0 | 0 | none |
| 9b | | | 17.1 | 0 | 0 | 0 | 0 | |
| 10a | D3, 5G | pQE30 | 5.3 | 0 | 0 | 0 | 0 | none |
| 10b | | | 16.0 | 0 | 0 | 0 | 0 | |
| 11a | D3, 5G | pCGP3086 | 2.9 | 0 | 2.7 | 0 | 0.7 | 3'FMT |
| 11b | | | 10.5 | 0.4 | 6.7 | 0 | 1.1 | |
| 12a | D3, 5G | pCGP3090 | 2.4 | 0 | 0.7 | 0 | 7.3 | 3'5'FMT |
| 12b | | | 5.4 | 0 | 0.8 | 0 | 12.4 | |

Tube No. = Tube numbers ("a" and "b" refer to duplicate product measurements)
3'FMT = flavonoid 3' methyltransferase,
3'5'FMT = flavonoid 3' 5' methyltransferase,
Del = delphinidin,
Cya = cyanidin,
Pet = petunidin,
Peo = peonidin,
Mal = malvidin.

TABLE 18

Products (expressed as percentage of total anthocyanidin) of the methyltransferase assays of extracts of *E. coli* containing pCGP3086, pCGP3090 or pQE30 control vector using delphinidin 3-glucoside, delphinidin 3-rutinoside and delphinidin 3,5-diglucoside as substrate and SAM as methyl donor

| Tube No. | Substrate | Plasmid | of anthocyanidin detected | | | | |
|---|---|---|---|---|---|---|---|
| | | | del | cya | pet | peo | mal |
| 1a | D3R | none | 97.0 | 3.0 | 0.0 | 0.0 | 0.0 |
| 1b | | | 94.3 | 2.7 | 3.0 | 0.0 | 0.0 |
| 2a | D3R | pQE30 | 93.2 | 3.4 | 3.4 | 0.0 | 0.0 |
| 2b | | | 94.7 | 2.5 | 2.8 | 0.0 | 0.0 |
| 3a | D3R | pCGP3086 | 21.2 | 2.5 | 58.5 | 1.2 | 16.6 |
| 3b | | (PFMT) | 21.7 | 2.5 | 57.4 | 1.1 | 17.4 |
| 4a | D3R | pCGP3090 | 13.2 | 0.0 | 4.0 | 1.9 | 80.9 |
| 4b | | (TFMT) | 14.6 | 0.0 | 4.3 | 1.9 | 79.1 |
| 5a | D3G | none | 75.3 | 16.5 | 8.2 | 0.0 | 0.0 |
| 5b | | | 77.7 | 15.2 | 7.1 | 0.0 | 0.0 |
| 6a | D3G | pQE30 | 82.5 | 12.0 | 5.6 | 0.0 | 0.0 |
| 6b | | | 85.0 | 10.2 | 4.8 | 0.0 | 0.0 |
| 7a | D3G | pCGP3086 | 35.5 | 11.8 | 44.0 | 2.7 | 6.0 |

TABLE 18-continued

Products (expressed as percentage of total anthocyanidin)
of the methyltransferase assays of extracts of *E. coli*
containing pCGP3086, pCGP3090 or pQE30 control
vector using delphinidin 3-glucoside, delphinidin
3-rutinoside and delphinidin 3,5-diglucoside as substrate
and SAM as methyl donor

| Tube No. | Substrate | Plasmid | \% of anthocyanidin detected | | | | |
|---|---|---|---|---|---|---|---|
| | | | del | cya | pet | peo | mal |
| 7b | | (PFMT) | 31.4 | 9.7 | 49.4 | 3.0 | 6.5 |
| 8a | D3G | pCGP3090 | 7.8 | 4.5 | 5.1 | 8.5 | 74.0 |
| 8b | | (TFMT) | 7.8 | 3.6 | 5.4 | 8.0 | 75.2 |
| 9a | D3, 5G | non | 100.0 | 0.0 | 0.0 | 0.0 | 0.0 |
| 9b | | | 100.0 | 0.0 | 0.0 | 0.0 | 0.0 |
| 10a | D3, 5G | pQE30 | 100.0 | 0.0 | 0.0 | 0.0 | 0.0 |
| 10b | | | 100.0 | 0.0 | 0.0 | 0.0 | 0.0 |
| 11a | D3, 5G | pCGP3086 | 45.6 | 0.0 | 43.4 | 0.0 | 11.0 |
| 11b | | (PFMT) | 55.9 | 2.2 | 35.9 | 0.0 | 6.0 |
| 12a | D3, 5G | pCGP3090 | 22.9 | 0.0 | 7.1 | 0.0 | 70.0 |
| 12b | | (TFMT) | 28.9 | 0.0 | 4.3 | 0.0 | 66.9 |

Tube No. = Tube numbers ("a" and "b" refer to duplicate product measurements)
del = delphinidin, expressed as a percentage of total anthocyanidins detected,
cya = cyanidin, expressed as a percentage of total anthocyanidins detected,
pet = petunidin, expressed as a percentage of total anthocyanidins detected,
peo = peonidin, expressed as a percentage of total anthocyanidins detected,
mal = malvidin, expressed as a percentage of total anthocyanidins detected.

Under the conditions of the assay, the *Petunia* FMT (E20) cDNA clone contained in pCGP3086 led to a flavonoid methyltransferase activity that utilized delphinidin 3-glucoside, delphinidin 3-rutinoside or delphinidin 3,5-diglucoside as substrate to produce predominantly petunidin and to a lesser degree, malvidin.

Previously published data on methyltransferase activities in crude protein extracts of petunia flowers suggest that the *Petunia* methyltransferases cannot utilize anthocyanidin 3-glucoside or anthocyanidin 3-rutinosides as substrates (Jonsson et al., 1982, supra). Under our assay conditions, however, the *Petunia* methyltransferase activity produced by the *Petunia* E20 clone in pCGP3086 was able to methylate each of delphinidin 3-glucoside, delphinidin 3-rutinoside and delphinidin 3,5-diglucoside.

The *Torenia* FMT cDNA clone contained in pCGP3090 also resulted in a flavonoid methyltransferase activity that utilized delphinidin 3-glucoside, delphinidin 3-rutinoside and delphinidin 3,5-diglucoside as substrate to produce predominantly malvidin and to a lesser degree, petunidin.

Example 11

Transformation of Rose to Produce Malvidin-Based Pigments

The predominant anthocyanins in commercially grown roses tend to be 3-glucosides or 3,5-diglucosides of cyanidin or pelargonidin (Mikanagi et al., *Biochem. System and Ecol.* 23: 183-200, 1995, Mikanagi et al., *Biochem. System and Ecol.* 28: 887-902, 2000). In order to produce malvidin-based pigments in these roses, a F3'5'H gene would need to be introduced to initially produce the precursors of malvidin pigments, delphinidin 3-glucosides or delphinidin 3,5 diglucosides. To then allow for conversion to malvidin pigments, a flavonoid methyltransferase with 3' and 5' activity and the ability to utilize 3-glucosides or 3,5-diglucosides of delphinidin would be required.

The binary vector plasmids pCGP3254 (FIG. 13), pSPB1534 (FIG. 15) and pSPB1532 (FIG. 18) containing a F3'5'H chimaeric gene along with a *Petunia* or *Torenia* FMT genes were, therefore, constructed to be introduced into rose to allow for the production of petunidin and/or malvidin-based pigments and thereby modify flower color. These binary plasmids are also introduced into a species that does not normally produce delphinidin-based pigments and does not contain a flavonoid methyltransferase capable of methylating anthocyanidins, specifically delphinidin. Such plants may include but are not limited to carnation, chrysanthemum, gerbera, orchids, *Euphorbia, Begonia*.

Construction of the Binary Vector pCGP3254 (35S 5': TFMT: 35S 3'; 35S 5': *Viola* F3'5'H: 35S 3': 35S 5': SuRB)

Figure 11:
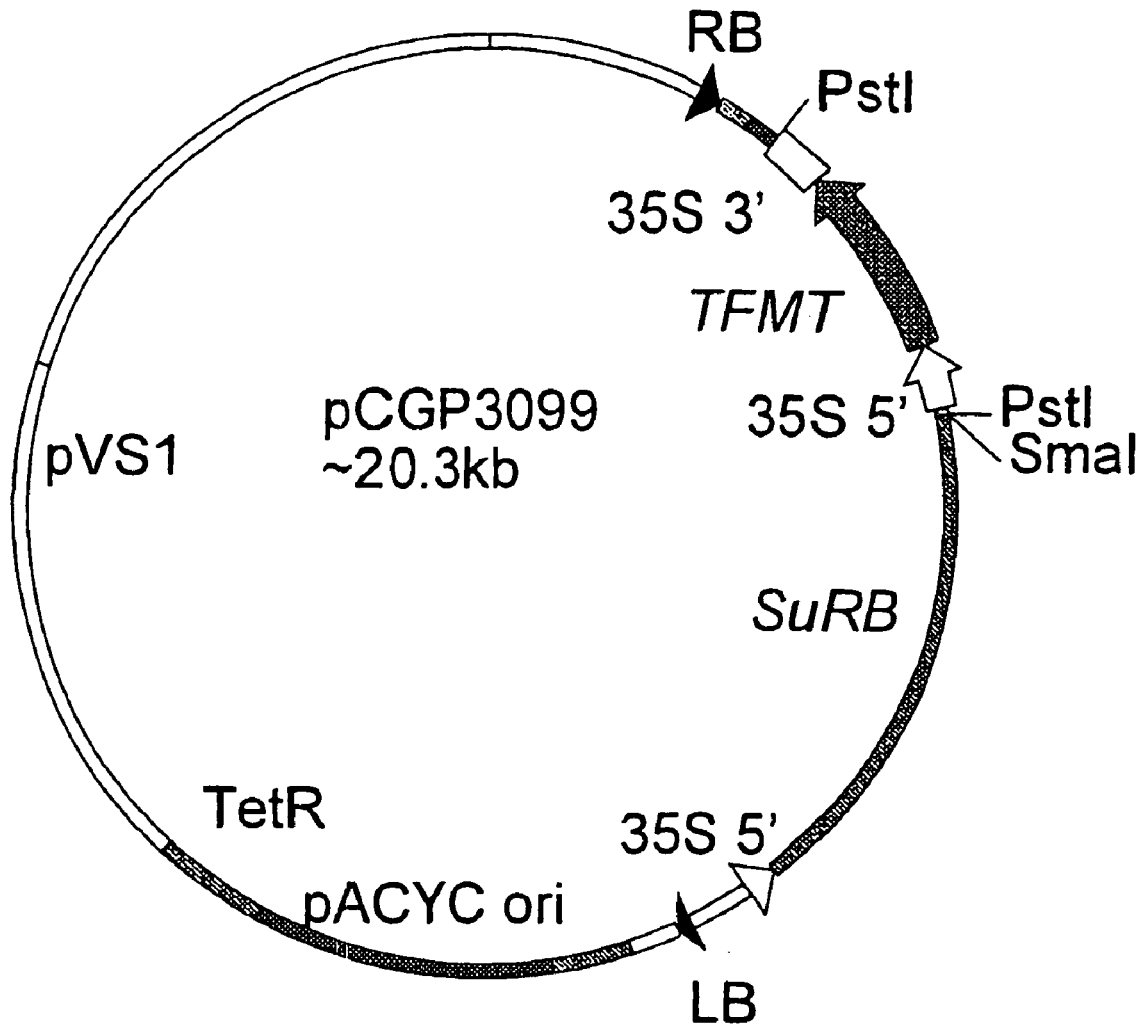
FIG. 11 is a diagrammatic representation of the binary plasmid pCGP3099. The chimaeric *Torenia* FMT gene (TFMT) from pCGP3097 (FIG. 10) was cloned into the binary vector pCGP1988 (FIG. 12) in a tandem orientation with the chimaeric SuRB gene. Abbreviations are as follows: TetR=the tetracycline resistance gene which confers resistance to the antibiotic tetracycline; LB=left border; RB=right border; SuRB=the coding region and terminator sequence from the acetolactate synthase gene from tobacco; 35S 5'=the promoter region from the CaMV 35S gene, 35S 3'=the terminator region from the CaMV 35S gene, pVS1=a broad host range origin of replication from a plasmid from *Pseuodomonas aeruginosa*, pACYC ori=modified replicon from pACYC184 from *E. coli*. Selected restriction enzyme sites are also marked.
Figure 12:
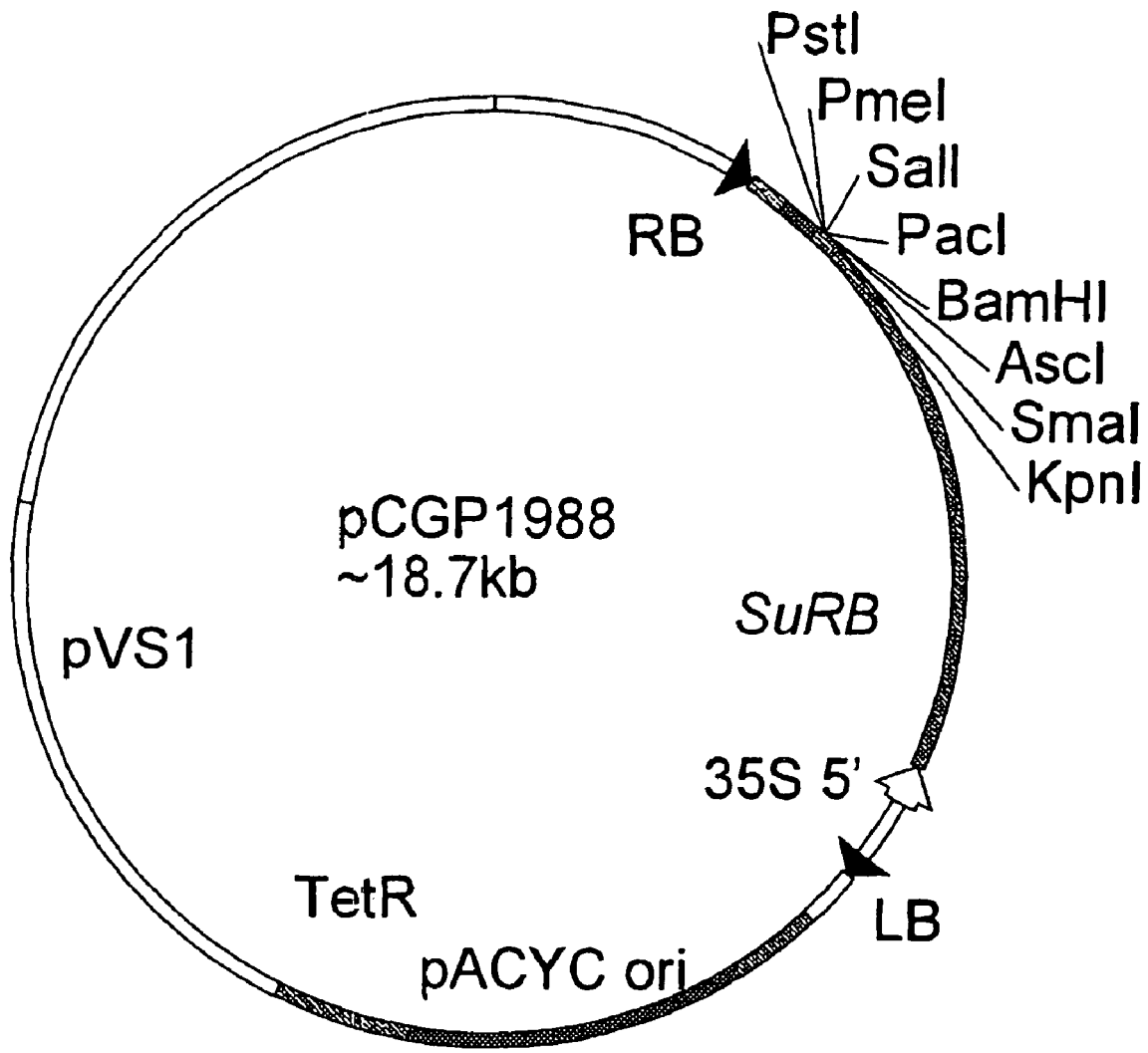
FIG. 12 is a diagrammatic representation of the binary plasmid pCGP1988. The multi-cloning site of the binary vector pWTT2132 (DNAP) was replaced with the multi-cloning site from pNEB193 (New England Biolabs). Abbreviations are as follows: TetR=the tetracycline resistance gene which confers resistance to the antibiotic tetracycline; LB=left border; RB=right border; SuRB=the coding region and terminator sequence from the acetolactate synthase gene from tobacco; 35S 5'=the promoter region from the CaMV 35S gene, pVS1=a broad host range origin of replication from a plasmid from *Pseuodomonas aeruginosa*, pACYC ori=modified replicon from pACYC184 from *E. coli*. Selected restriction enzyme sites are also marked.

The plasmid pCGP3254 contains a 35S 5': *Viola* F3'5'H: 35S 3' expression cassette (from pCGP2092) (FIG. 14) and a 35S 5': *Torenia* FMT: 35S 3' expression cassette (from pCGP3099) (FIG. 11) in tandem orientation with the selectable marker gene of the Ti binary vector pCGP1988 (FIG. 12).

(1) Construction of Intermediate Plasmids to pCGP3254

(i) Construction of pCGP3097 (35S 5': TFMT: 35S 3' Expression Cassette)

Plasmid pCGP3097 (FIG. 10) was constructed by cloning the *Torenia* FMT cDNA clone from pTMT5 into a CaMV 35S expression cassette.

Figure 10:
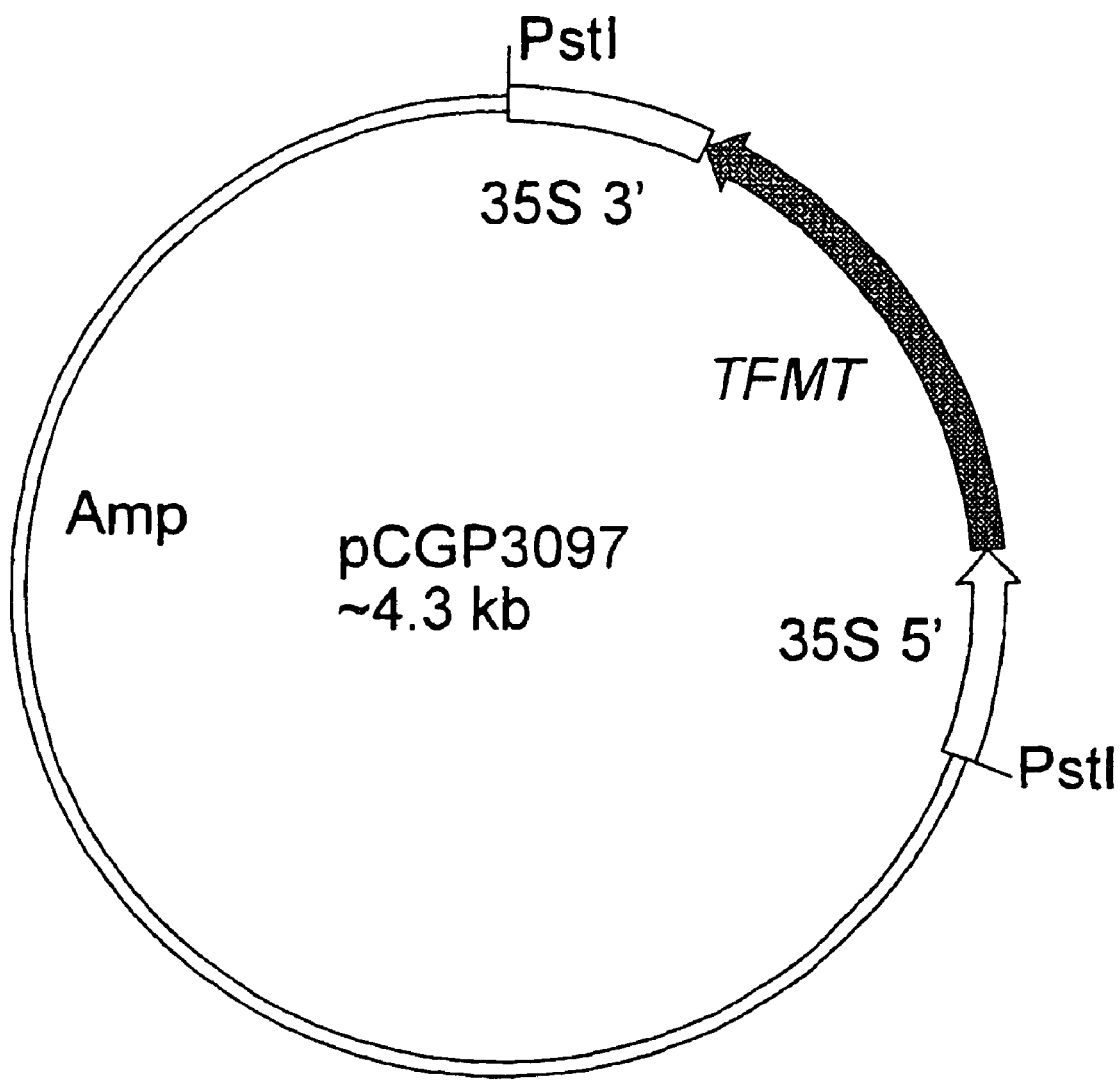
FIG. 10 is a diagrammatic representation of the plasmid pCGP3097. The *Torenia* FMT clone (TFMT) from pTMT5 was cloned into a CaMV35S expression cassette. Abbreviations are as follows: Amp=the ampicillin resistance gene which confers resistance to the antibiotic ampicillin, 35S 5'=the promoter region from the CaMV 35S gene, 35S 3'=the terminator region from the CaMV 35S gene. Selected restriction enzyme sites are also marked.

The plasmid pRTppoptcAFP was used as a source of a CaMV 35S promoter and terminator fragment. It was initially digested with XbaI, the overhanging 5' ends were repaired and then the plasmid was restricted with EcoRI to release the 3.3 kb vector containing the CaMV 35S expression cassette. The 3.3 kb vector was isolated and purified.

pTMT5 was digested initially with the restriction endonuclease Asp718 and the resulting 5' overhang ends were repaired. The linearized plasmid was then restricted with the restriction endonuclease EcoRI to release the 1.0 kb *Torenia* FMT cDNA fragment which was isolated, purified and then ligated with the XbaI (blunt)/EcoRI ends of the pRTppoptc vector (described above). Correct ligation of the fragments was established by restriction endonuclease analysis (HinDIII, ClaI, XhoI, PstI, and SphI) of plasmid DNA isolated from ampicillin-resistant transformants. The resulting plasmid was designated pCGP3097 (FIG. 10).

(ii) Construction of pCGP3099 (35S 5': TFMT: 35S 3'; 35S 5': SuRB Expression Binary)

Plasmid pCGP3099 (FIG. 11) was constructed by cloning the chimaeric *Torenia* FMT gene from pCGP3097 (FIG. 10) into the Ti binary vector pCGP1988. The binary vector pCGP1988 (FIG. 12) is based on the binary vector pWTT2132 (DNAP) but contains the multi-cloning site from pNEB193 (New England Biolabs).

The 35S 5': *Torenia* FMT: 35S 3' expression cassette from pCGP3097 (FIG. 10) was released by digestion with the restriction endonuclease PstI. A 1.66 kb fragment containing the chimaeric *Torenia* FMT gene was subsequently isolated and ligated with PstI ends of pCGP1988. Correct ligation of the chimaeric gene in tandem with the 35S 5': SuRB gene of pCGP3099 was established by restriction endonuclease analysis (HinDIII, XhoI, PstI, Asp718, EcoRI, and EcoRV) of plasmid DNA isolated from tetracycline-resistant transformants. The resulting plasmid was designated pCGP3099 (FIG. 11).

(iii) Construction of pCGP2092 (35S 5': *Viola* F3'5'H (BP#40): 35S 3' Expression Cassette)

The plasmid pCGP2092 (FIG. 14) was constructed by cloning the F3'5'H cDNA clone isolated from *Viola* sp. as a XbaI/EcoRI 1.6 kb fragment from pCGP1961 behind the CaMV 35S promoter contained in pRTppoptc.

Figure 14:
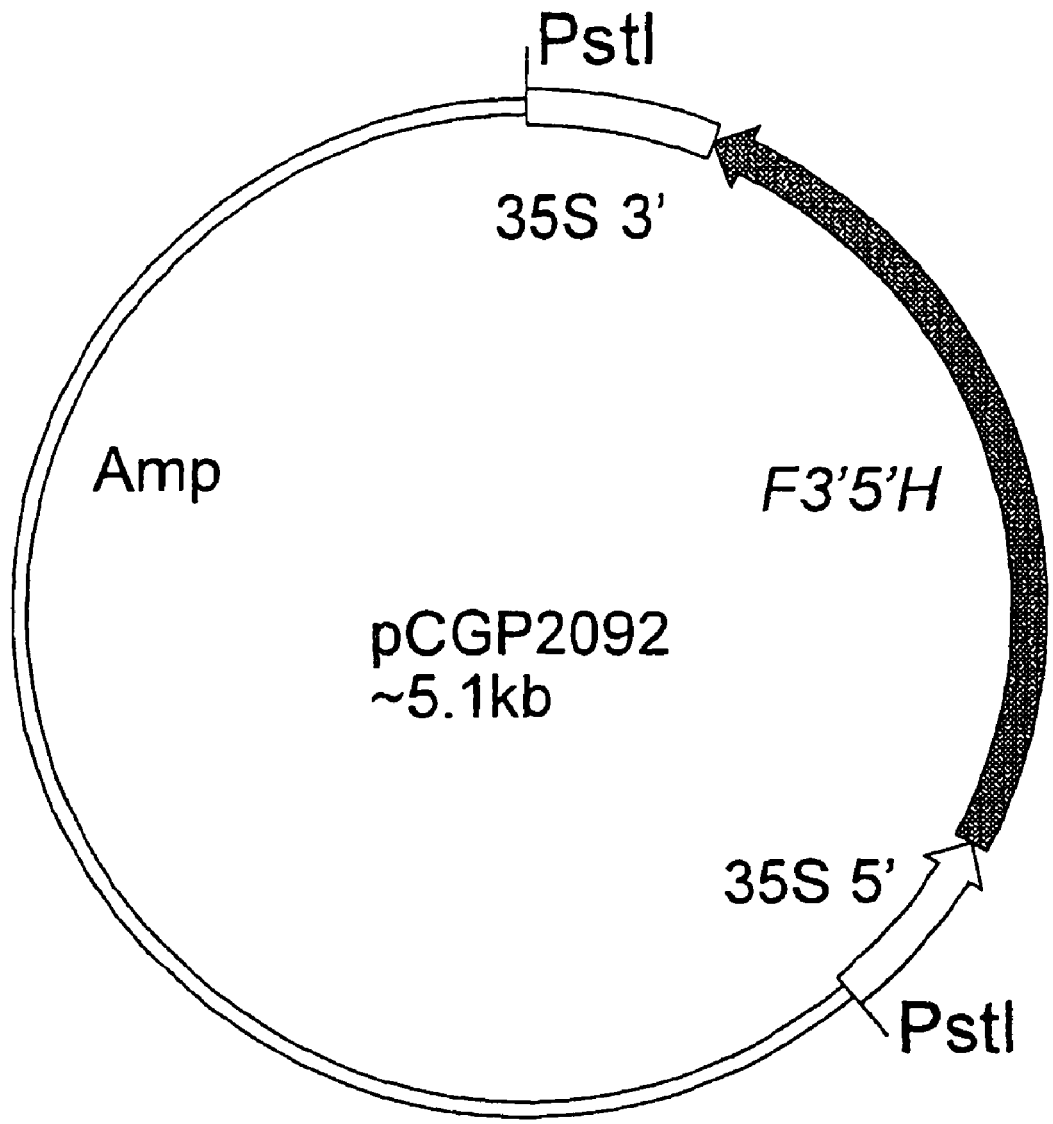
FIG. 14 is a diagrammatic representation of the plasmid pCGP2092. The *Viola* F3'5'H clone from pCGP1961 was cloned into a CaMV35S expression cassette. Abbreviations are as follows: F3'5'H=flavonoid 3',5' hydroxylase cDNA clone from *Viola*, Amp=the ampicillin resistance gene which confers resistance to the antibiotic ampicillin, 35S 5'=the promoter region from the CaMV 35S gene, 35S 3'=the terminator region from the CaMV 35S gene. Selected restriction enzyme sites are also marked.

The plasmid pCGP1961 (Australian Provisional Patent Applications No. 2002951088 and 2002952835, 2002, supra) was initially digested with the restriction endonuclease Asp718 and after repair of the overhanging 5' ends was digested with the restriction endonuclease EcoRI to release a 1.6 kb fragment containing the F3'5'H chimaeric gene. The fragment was isolated and ligated with XbaI (blunt)/EcoRI ends of the 3.3 kb pRTppoptc vector (described above). Correct ligation of the *Viola* F3'5'H cDNA clone (BP#40) into the CaMV 35S expression cassette was established by restriction endonuclease analysis (HinDIII, XhoI, PstI) of plasmid DNA isolated from ampicillin-resistant transformants. The resulting plasmid was designated as pCGP2092 (FIG. 14).

Construction of pCGP3254

Figure 13:
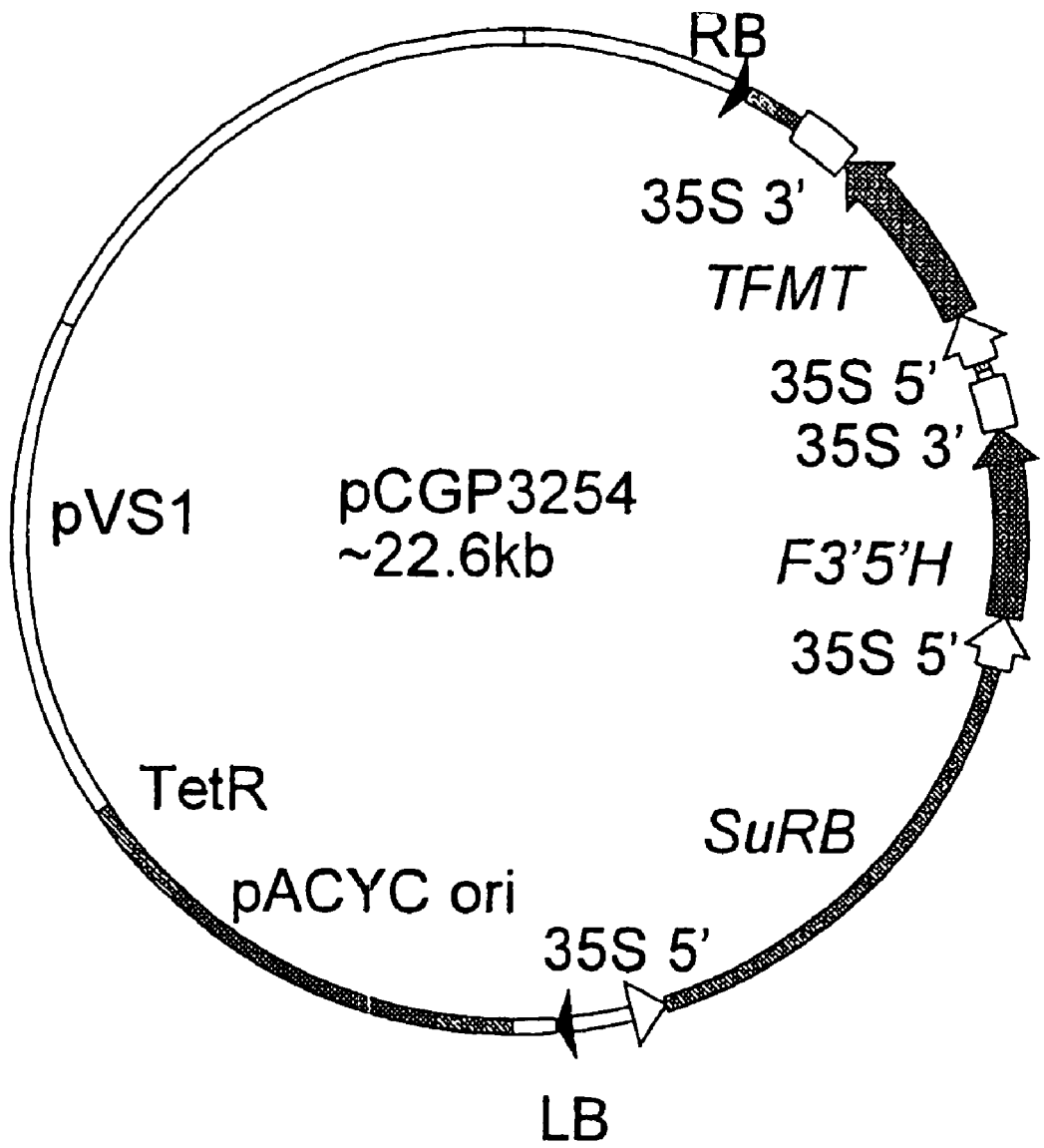
FIG. 13 is a diagrammatic representation of the binary plasmid pCGP3254. The chimaeric F3'5'H gene from pCGP2092 (FIG. 14) was cloned into the binary plasmid pCGP3099 (FIG. 11) in a tandem orientation with the chimaeric SuRB gene and the chimaeric TFMT gene. Abbreviations are as follows: F3'5'H=flavonoid 3',5' hydroxylase cDNA clone from *Viola*, TFMT=*Torenia* FMT cDNA clone, TetR=the tetracycline resistance gene which confers resistance to the antibiotic tetracycline; LB=left border; RB=right border; SuRB=the coding region and terminator sequence from the acetolactate synthase gene from tobacco; 35S 5'=the promoter region from the CaMV 35S gene, 35S 3'=the terminator region from the CaMV 35S gene, pVS1=a broad host range origin of replication from a plasmid from *Pseuodomonas aeruginosa*, pACYC ori=modified replicon from pACYC184 from *E. coli*. Selected restriction enzyme sites are also marked.

The chimaeric F3'5'H gene was subsequently released from pCGP2092 by restriction with the restriction endonuclease PstI followed by treatment with T4 DNA polymerase to repair the overhanging 3' ends. The fragment was isolated and ligated with the SmaI ends of pCGP3099 (described above). Correct insertion of the F3'5'H chimaeric gene in tandem with the 35S 5': SuRB gene and 35S 5': *Torenia* FMT: 35S 3' expression cassette gene was established by restriction endonuclease analysis (HinDIII, XhoI, NcoI, SalI, EcoRI, EcoRV) of plasmid DNA isolated from tetracycline-resistant transformants. The resulting plasmid was designated pCGP3254 (FIG. 13).

Plant Transformation with pCGP3254

The binary vector pCGP3254 (FIG. 13) was introduced into *A. tumefaciens* strain AGL0 and the T-DNA contained in pCGP3254 was subsequently introduced into rose cultivars Medeo and Sonia via *Agrobacterium*-mediated transformation.

(2) Construction of the Binary Vectors (a) pSPB1534 (e35S 5': BP#40: pet D8 3'; e35S 5': PFMT: nos 3') and (b) pSPB1532 (e35S 5': BP#40: pet D8 3'; e35S 5': TFMT: nos 3')

(a) The binary vector plasmid pSPB1534 (FIG. 15) contains an e35S 5': *Viola* F3'5'H (BP#40): pet D8 3' expression cassette (from pSPB580 (FIG. 16)) in tandem orientation with an e35S. PFMT. nos 3' expression cassette (from pSPB1531 (FIG. 17)). Both chimaeric genes are in a tandem orientation with the nos 5': nptII. nos 3' selectable marker gene cassette of the Ti binary vector pBINPlus (van Engelen et al., *Transgenic Research*, 4: 288-290, 1995).

(b) The binary vector plasmid pSPB1532 (FIG. 18) contains an e35S 5': *Viola* F3'5'H (BP#40): pet D8 3' expression cassette (from pSPB580 (FIG. 16)) in tandem orientation with an e35S 5': TFMT: nos 3' expression cassette (from pSPB1530 (FIG. 19)). Both chimaeric genes are in a tandem orientation with the nos 5': nptII: nos 3' selectable marker gene cassette of the Ti binary vector pBINPlus (van Engelen et al., 1995, supra).

TABLE 19

Oligonucleotides used as primers in the construction of the binary vectors pSPB1534 and pSPB1532

| SEQ ID NO: | NAME | SEQUENCE (5' TO 3') |
|---|---|---|
| 28 | petD8 #1 | CCC TCG AGT TTC TAT TTT GTG TGT GTT G |
| 29 | petD8 #2 | GGG AAT TCT AGA GCT CGA GGA TCA CG |
| 30 | PMT-F | ACT ACC AAG GAT CCT ACT GAA GCA |
| 31 | PMT-R | CTC GAA TGA AGC TTT TGT TA |
| 32 | TMT-F | CAT AAA TAG GAT CCG CAG CAG CAA |
| 33 | TMT-R | AGT CTC ATA AGC TTC TCT AT |

Construction of Intermediate Plasmids to pSPB1534 and pSPB1532

(i) Construction of pSPB580 (e35S 5': BP#40: pet D8 3)

The plasmid pSPB580 (FIG. 16) contains the *Viola* F3'5'H cDNA clone in between an enhanced CaMV 35S promoter fragment (e35S 5') and a *Petunia* PLTP terminator (petD8 3') fragment.

(1) Isolation of the F3'5'H Clone from *Viola* sp.

The isolation of a F3'5'H cDNA clone from *Viola* sp. cultivar black pansy has been described in Australian Provisional Patent Application Nos. 2002951088 and 2002952835, supra). The plasmid pCGP1961 (Australian Provisional Patent Application Nos. 2002951088 and 2002952835, supra) was linearized upon digestion with the restriction endonuclease BamHI. An ~1.7 kb DNA fragment containing a F3'5'H cDNA clone (BP#40) from *Viola* sp. cv. black pansy was recovered upon partial digestion with the restriction endonuclease, XhoI.

(2) Isolation of an Enhanced CaMV 35S Promoter Fragment

The binary vector, pBE2113-GUS contains a GUS gene under the control of an enhanced CaMV 355 promoter (e35S 5) with a terminator region from the nopaline synthase gene of *Agrobacterium* (nos 3) (Mitsuhashi et al., *Plant Cell Physiol.* 37: 49-59, 1996). The plasmid pBE2113-GUS was digested with the restriction endonuclease SnaBI and a BamHI linker (5'-GGGATCCC-3') [SEQ ID NO:45] was then ligated with the overhanging ends to yield pBE2113-ΔGUS. A ~0.7 kb fragment containing the enhanced CaMV 35S promoter (e35S 5) was then released upon digestion of pBE2113-ΔGUS with the restriction endonucleases HindIII and BamHI.

(3) Isolation of a Terminator Fragment from the *Petunia* PLTP (D8) Gene (petD8 3')

A terminator fragment from the *Petunia* phospholipid transfer protein (PLTP) gene (petD8 3') (Holton, 1992, supra) was amplified by PCR. The primers pet D8 #1 [SEQ ID NO: 28] (Table 19) and pet D8 #2 [SEQ ID NO: 29] (Table 19) along with the plasmid template pCGP13ΔBam (Holton, 1992, supra) were used to amplify the *Petunia* PLTP terminator fragment (petD8 3'). The amplified fragment of about 0.8 kb was then digested with the restriction endonucleases EcoRI and XhoI.

(4) Construction of pUCAPAsc—(a Shuttle Cloning Vector)

The plasmid pUCAP is based on the cloning vector pUC19 (NEB) but contains an extended multiple cloning site (VanEngelen et al., *Transgenic Res.* 4: 288-290, 1995). pUCAP was digested with the restriction endonuclease PacI. The overhanging ends were repaired and then ligated with AscI linker (5'-GGCGCGCC-3') [SEQ ID NO:46] to yield pUCAPAsc (similar to pUCAP without a PacI recognition site and with 2 AscI recognition sequences at either ends of the multiple cloning site).

(5) Construction of pSPB580 (e35S: BP#40: pet D8 3)

The 1.7 kb BamHI/XhoI fragment containing the *Viola* F3'5'H (BP#40) cDNA clone (isolation described above) was ligated with the BamHI/EcoRI 2.7 kb vector fragment obtained from pUCAPAsc (described above) and the EcoRI/XhoI fragment containing the a *Petunia* PLTP terminator (petD8 3') (described above). Correct insertion of the fragments was established by restriction endonuclease analysis of plasmid DNA isolated from ampicillin-resistant transformants. The resulting plasmid was designated pSPB51

Figure 16:
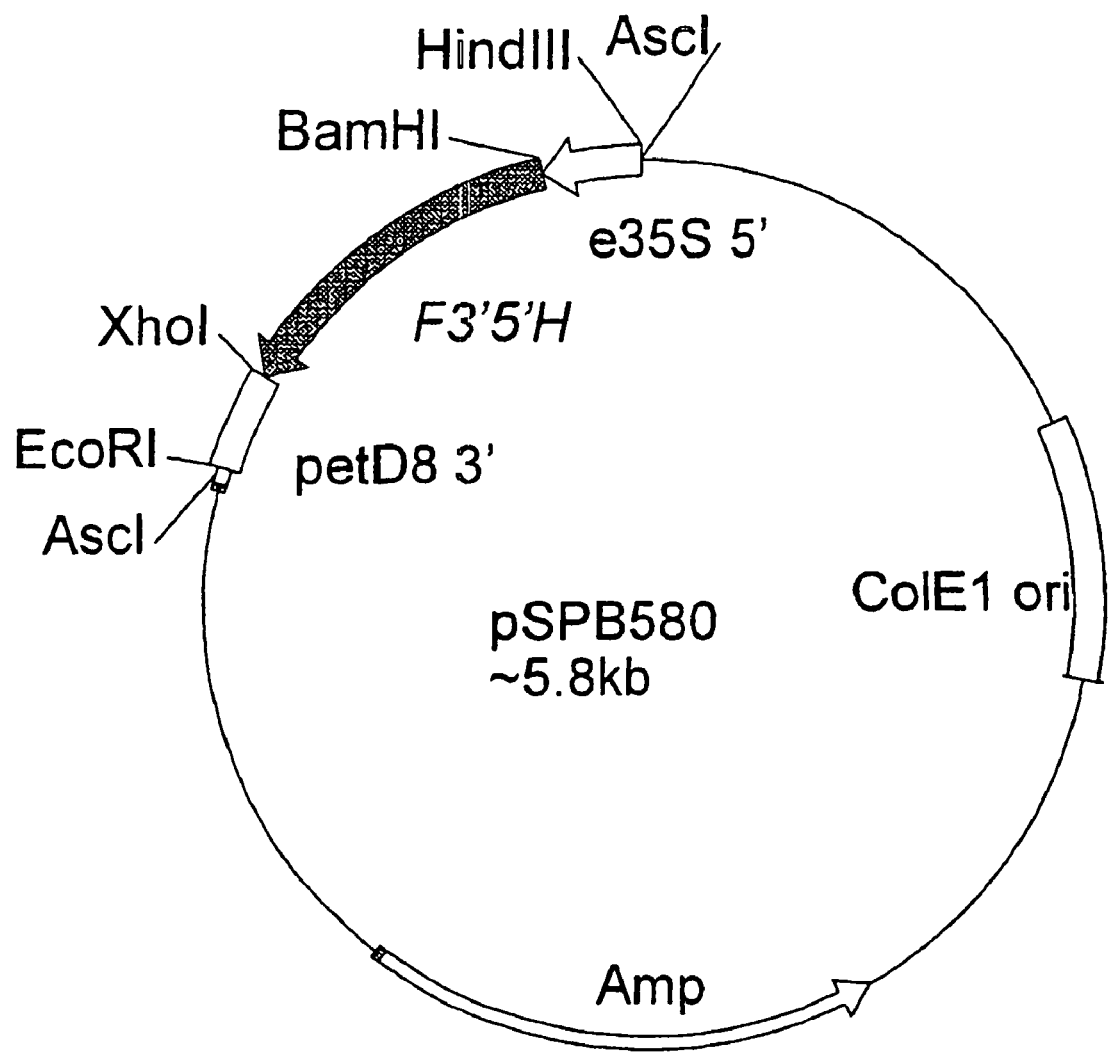
FIG. 16 is a diagrammatic representation of the plasmid pSPB580. The *Viola* F3'5'H (BP#40) cDNA clone (from pCGP1961) was cloned between an enhanced CaMV 35S promoter fragment (from pBE2113-GUS) and a *Petunia* PLTP (D8) terminator fragment (from pCGP13ΔBam). Abbreviations are as follows: F3'5'H=flavonoid 3',5' hydroxylase cDNA clone from *Viola*, Amp=the ampicillin resistance gene which confers resistance to the antibiotic ampicillin, e35S 5'=an enhanced promoter region from the CaMV 35S gene, ColE1=*E. coli* plasmid ColE1 origin, petD8 3'=the terminator region from the *Petunia* PLTP gene.

The 0.7 kb HindIII/BamHI fragment containing the enhanced CaMV 35S promoter region (described above) was ligated with the HindIII/BamHI ends of the plasmid pSPB51. Correct insertion of the fragment was established by restriction endonuclease analysis of plasmid DNA isolated from ampicillin-resistant transformants. The resulting plasmid was designated pSPB580 (FIG. 16).

(ii) Construction of the Binary Vector pSPB176 (e35S 5': GUS: nos 3'; nos 5': nptII: nos 3')

The binary vector pSPB176 (FIG. 20) contains an e35S 5': GUS: nos 3' expression cassette in a tandem orientation to the selectable marker gene cassette of the Ti binary vector pBIN-Plus (van Engelen et al., 1995, supra).

Figure 20:
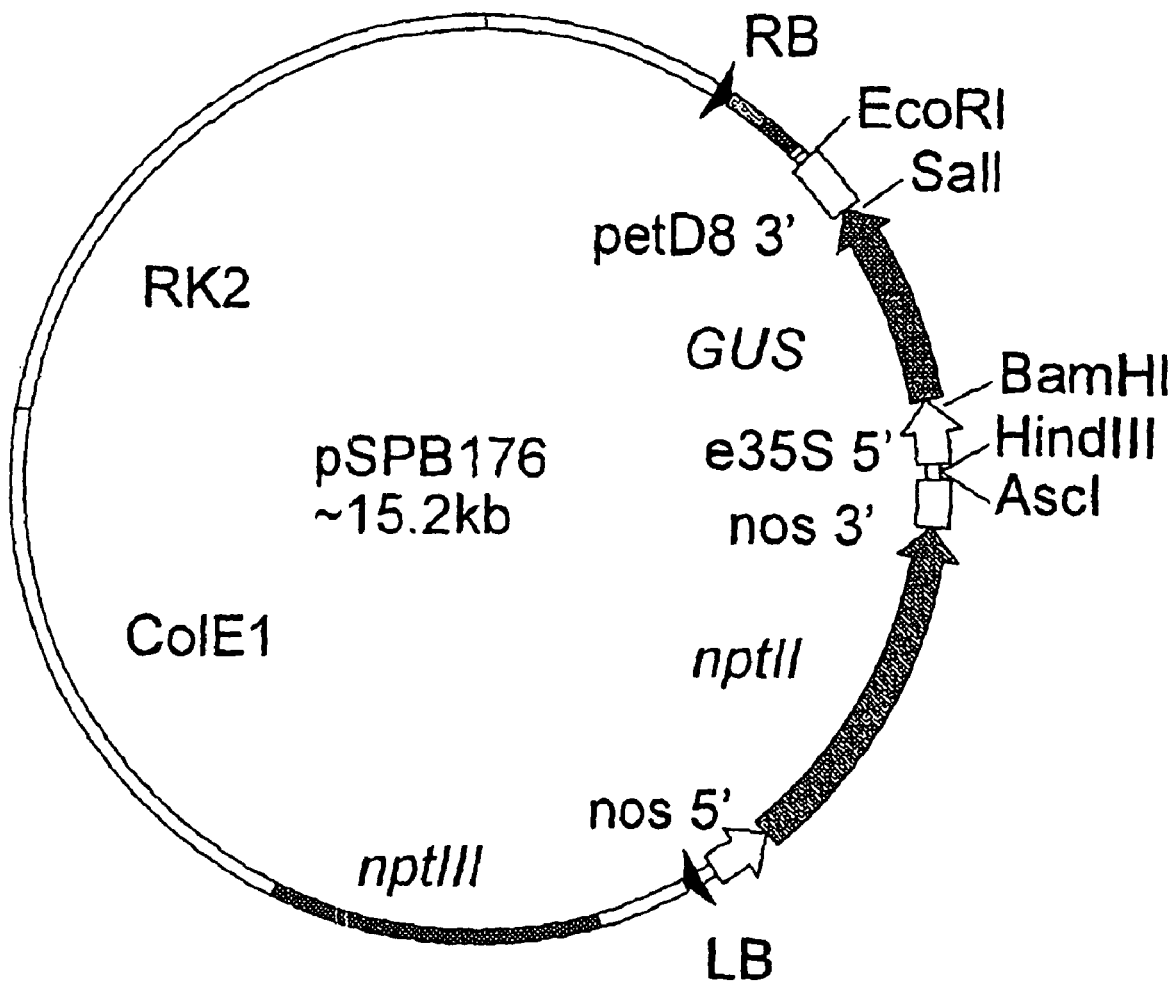
FIG. 20 is a diagrammatic representation of the binary plasmid pSPB176. A chimaeric GUS gene (from pBE2113-GUS) was cloned in a tandem orientation to the nptII selectable marker gene of the Ti binary vector pBINPlus. Abbreviations are as follows: nptIII=the neomycin phosphotransferase III gene which confers resistance to the antibiotic kanamycin, nptII=the neomycin phosphotransferase II gene which confers resistance to the antibiotic kanamycin, e35S 5'=an enhanced promoter region from the CaMV 35S gene, petD8 3'=the terminator region from the *Petunia* PLTP gene, nos 5'=promoter region from the nopaline synthase gene of *Agrobacterium*, nos 3'=terminator region from the nopaline synthase gene of *Agrobacterium*, ColE1=*E. coli* plasmid ColE1 origin, RK2 broad host range Gram-negative plasmid RK2 origin, LB=left border, RB=right border. Selected restriction enzyme sites are also marked.

The plasmid pBE2113-ΔGUS (described above) was digested with SacI. The overhanging 3' ends were repaired and then ligated with a SalI linker (5'-GGTCGACC-3') [SEQ ID NO:47] to yield pBE2113-ΔGUSs. A fragment containing the e35S 5': GUS: nos 3' expression cassette was released from pBE2113-ΔGUSs upon digestion with the restriction endonucleases HindIII and EcoRI. The HindIII/EcoRI fragment was then ligated with HindIII/EcoRI ends of the Ti binary vector pBinPLUS (VanEngelen et al., 1995, supra). Correct insertion of the fragment was established by restriction endonuclease analysis of plasmid DNA isolated from kanamycin-resistant transformants. The resulting plasmid was designated pSPB176 (FIG. 20).

(iii) Construction of the Intermediate Binary Vector pSPB1531 (e35S 5': PFMT: nos 3'; nos 5': nptII: nos 3')

The binary vector plasmid pSPB1531 (FIG. 17) contains the *Petunia* FMT cDNA clone (with a shortened 5' non-coding region as compared to the E20 clone) between an enhanced CaMV 35S promoter fragment (e35S 5') and a nos terminator fragment (nos 3') in tandem with the nos 5': nptII: nos 3' selectable marker gene cassette of the Ti binary vector pBINPlus (van Engelen et al., 1995, supra).

Figure 17:
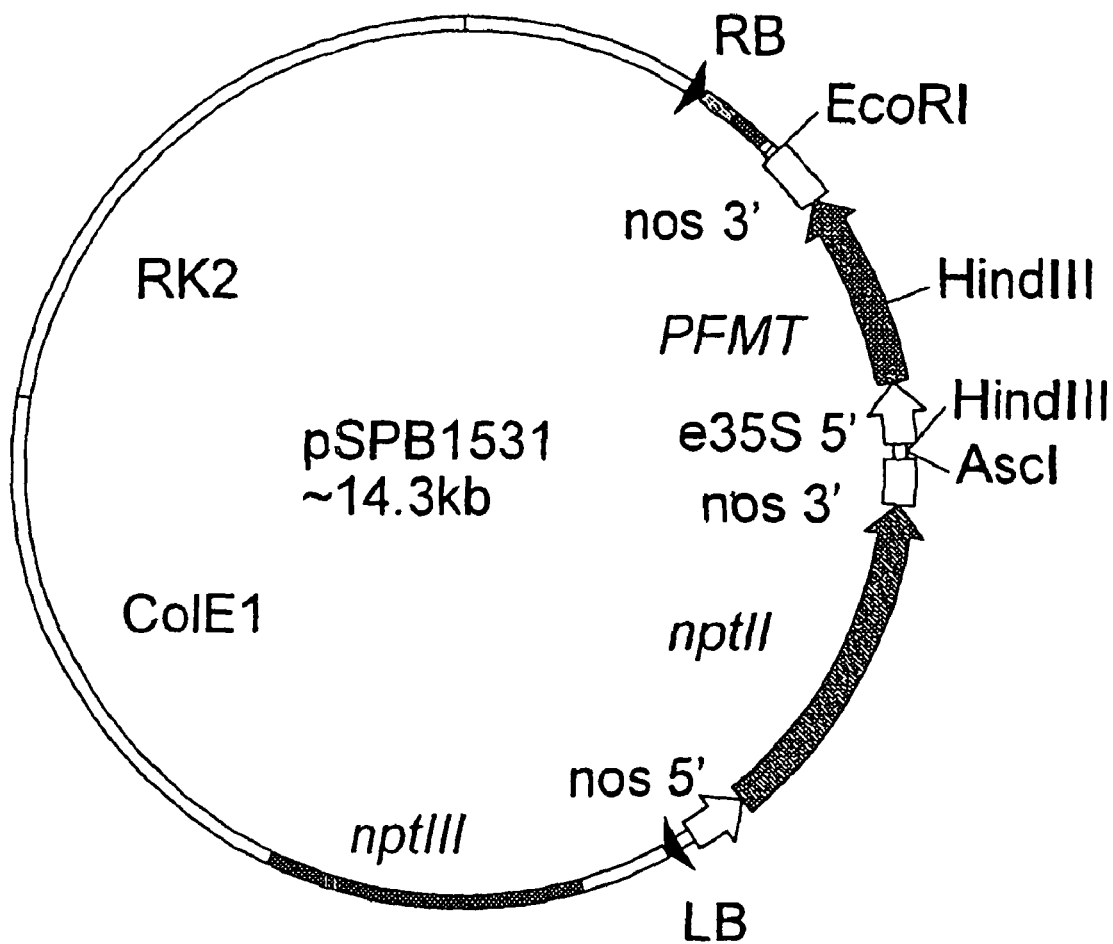
FIG. 17 is a diagrammatic representation of the binary plasmid pSPB1531. The chimaeric *Petunia* FMT (PFMT) cDNA clone was amplified by PCR (from pCGP1907) (FIG. 3) and replaced the GUS coding region of the binary plasmid pSPB176 (FIG. 20). Abbreviations are as follows: nptIII=the neomycin phosphotransferase III gene which confers resistance to the antibiotic kanamycin, nptII=the neomycin phosphotransferase II gene which confers resistance to the antibiotic kanamycin, e35S 5'=an enhanced promoter region from the CaMV 35S gene, nos 5'=promoter region from the nopaline synthase gene of *Agrobacterium*, nos 3'=terminator region from the nopaline synthase gene of *Agrobacterium*, ColE1=*E. coli* plasmid ColE1 origin, RK2=broad host range Gram-negative plasmid RK2 origin, LB=left border, RB=right border. Selected restriction enzyme sites are also marked.

The 5' region of the *Petunia* FMT cDNA clone contained in pCGP1907 (FIG. 3) was amplified by PCR using the primers PMT-F [SEQ ID NO: 30] and PMT-R [SEQ ID NO: 31] and 10 ng of the plasmid pCGP1907 as template. The oligonucleotide PMT-F [SEQ ID NO:30] was designed to amplify from position 43-66) of SEQ ID NO:4 and incorporated a BamHI recognition sequence for ease of cloning. The PMT-R [SEQ ID NO: 31] primer was designed to amplify from position 192-173 of SEQ ID NO:4 and incorporated a HindIII recognition sequence for ease of cloning. The amplified *Petunia* FMT 5' partial fragment was then digested with the restriction endonucleases BamHI and HindIII and ligated with the 0.7 kb HindIII/XhoI *Petunia* FMT 3' partial fragment isolated from the plasmid pCGP1907 (FIG. 3) and BamHI/SalI ends of the Ti binary vector pSPB176 (FIG. 20). Correct insertion of the fragments was established by restriction endonuclease analysis of plasmid DNA isolated from kanamycin-resistant transformants. The resulting plasmid was designated pSPB1531 (FIG. 17).

(iv) Construction of the Intermediate Binary Vector pSPB1530 (e35S 5': TFMT: nos 3'; nos 5': nptII: nos 3')

The binary vector plasmid pSPB1530 (FIG. 19) contains the *Torenia* FMT cDNA clone (with a shortened 5' non-coding region as compared to the TFMT clone) between an enhanced. CaMV 35S promoter fragment (e35S 5') and a nos terminator fragment (nos 3') in tandem with the nos 5': nptII: nos 3' selectable marker gene cassette of the Ti binary vector pBINPlus.

Figure 19:
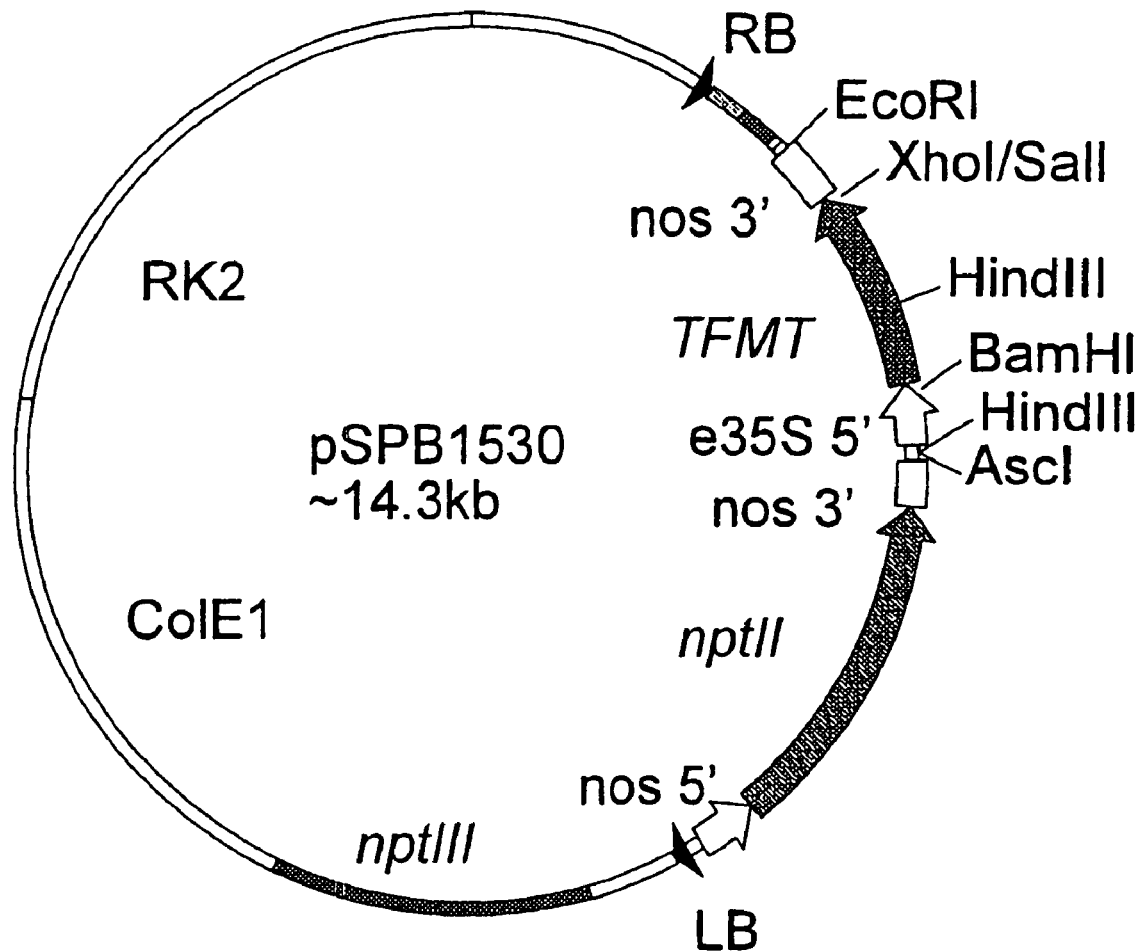
FIG. 19 is a diagrammatic representation of the binary plasmid pSPB1530. The chimaeric *Torenia* FMT (TFMT) cDNA clone was amplified by PCR (from pTMT5) (FIG. 8) and replaced the GUS coding region of the binary plasmid pSPB176 (FIG. 20). Abbreviations are as follows: nptIII=the neomycin phosphotransferase III gene which confers resistance to the antibiotic kanamycin, nptII=the neomycin phosphotransferase II gene which confers resistance to the antibiotic kanamycin, e35S 5' an enhanced promoter region from the CaMV 35S gene, nos 5'=promoter region from the nopaline synthase gene of *Agrobacterium*, nos 3'=terminator region from the nopaline synthase gene of *Agrobacterium*, ColE1=*E. coli* plasmid ColE1 origin, RK2=broad host range Gram-negative plasmid RK2 origin, LB=left border, RB=right border. Selected restriction enzyme sites are also marked.

The 5' region of the *Torenia* FMT cDNA clone contained in pTMT5 was amplified by PCR using the primers TMT-F [SEQ ID NO:32] and TMT-R [SEQ ID NO:33] (Table 19) and 10 ng of pTMT5 as the template. The oligonucleotide TMT-F [SEQ ID NO:32] (Table 19) was designed to amplify from position 34-53 of SEQ ID NO:11 and incorporated a BamHI recognition sequence for ease of cloning. The TMT-R [SEQ ID NO: 33] (Table 19) primer was designed to amplify from position 214-190 of SEQ ID NO:11 and incorporated a HindIII recognition sequence for ease of cloning. The amplified *Torenia* FMT 5' partial fragment was then digested with the restriction endonucleases BamHI and HindIII and ligated with a ~0.6 kb HindIII/XhoI *Torenia* FMT 3' partial fragment isolated from pTMT5 and BamHI/SalI ends of the Ti binary vector pSPB176 (FIG. 20). Correct insertion of the fragments was established by restriction endonuclease analysis of plasmid DNA isolated from kanamycin-resistant transformants. The resulting plasmid was designated pSPB1530 (FIG. 19).

(v) Construction of the Binary Vector pSPB1534 (e35S 5': BP#40: pet D8 3'; e35S 5': PFMT: nos 3'; nos 5': nptII: nos 3')

Figure 15:
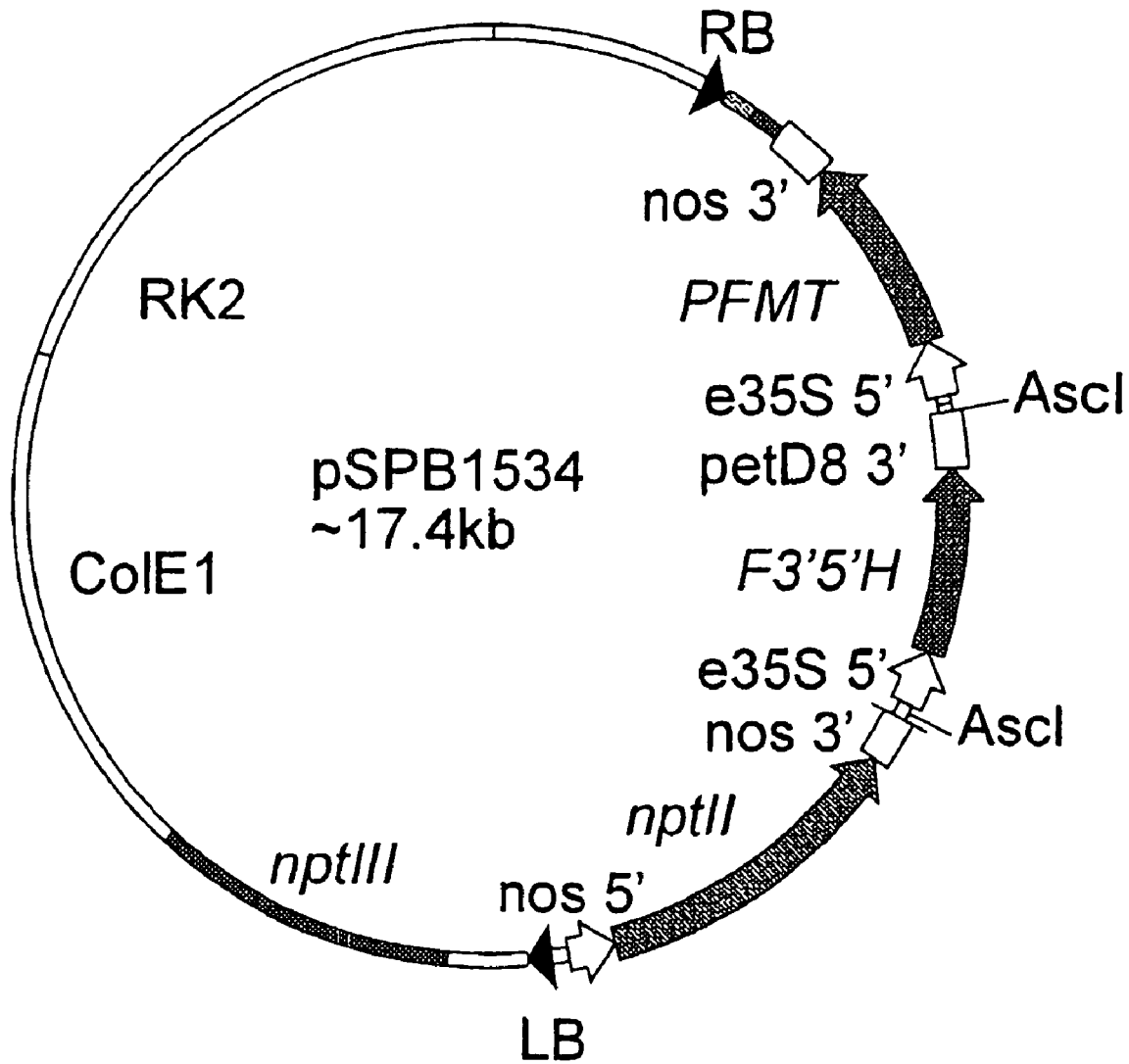
FIG. 15 is a diagrammatic representation of the binary plasmid pSPB1534. The chimaeric *Viola* F3'5'H gene from pSPB580 (FIG. 16) was cloned in a tandem orientation with the chimaeric *Petunia* FMT gene and the selectable marker gene of the Ti binary plasmid pSPB1531 (FIG. 17). Abbreviations are as follows: F3'5'H=flavonoid 3',5' hydroxylase cDNA clone from *Viola*, PFMT=*Petunia* FMT cDNA clone nptIII=the neomycin phosphotransferase III gene which confers resistance to the antibiotic kanamycin, nptII=the neomycin phosphotransferase II gene which confers resistance to the antibiotic kanamycin, e35S 5'=an enhanced promoter region from the CaMV 35S gene, petD8 3'=the terminator region from the *Petunia* PLTP gene, nos 5'=promoter region from the nopaline synthase gene of *Agrobacterium*, nos 3'=terminator region from the nopaline synthase gene of *Agrobacterium*, ColE1=*E. coli* plasmid ColE1 origin, RK2=broad host range Gram-negative plasmid RK2 origin, LB=left border, RB=right border. Selected restriction enzyme sites are also marked.

An ~3.1 kb DNA fragment containing the e35S 5': *Viola* F3'5'H (BP40): pet D8 3' expression cassette was isolated from the plasmid pSPB580 (FIG. 16) upon digestion with the restriction endonuclease AscI. The purified fragment was ligated with the AscI ends of the Ti binary plasmid pSPB1531 (FIG. 17). Correct insertion of the fragment in a tandem orientation with the *Petunia* FMT cassette and the selectable marker cassette was established by restriction endonuclease analysis of plasmid DNA isolated from kanamycin-resistant transformants. The resulting plasmid was designated pSPB1534 (FIG. 15).

Plant Transformation with pSPB1534

The binary vector plasmid pSPB1534 (FIG. 15) was introduced into *A. tumefaciens* strain AGL0 and the T-DNA contained in pSPB1534 was introduced into the *Rosa hybrida* cultivar WKS124 via *Agrobacterium*-mediated transformation.

Construction of the Binary Vector pSPB1532 (e35S 5': BP#40: pet D8 3'; e35S 5': TFMT: nos 3'; nos 5': nptII: nos 3')

Figure 18:
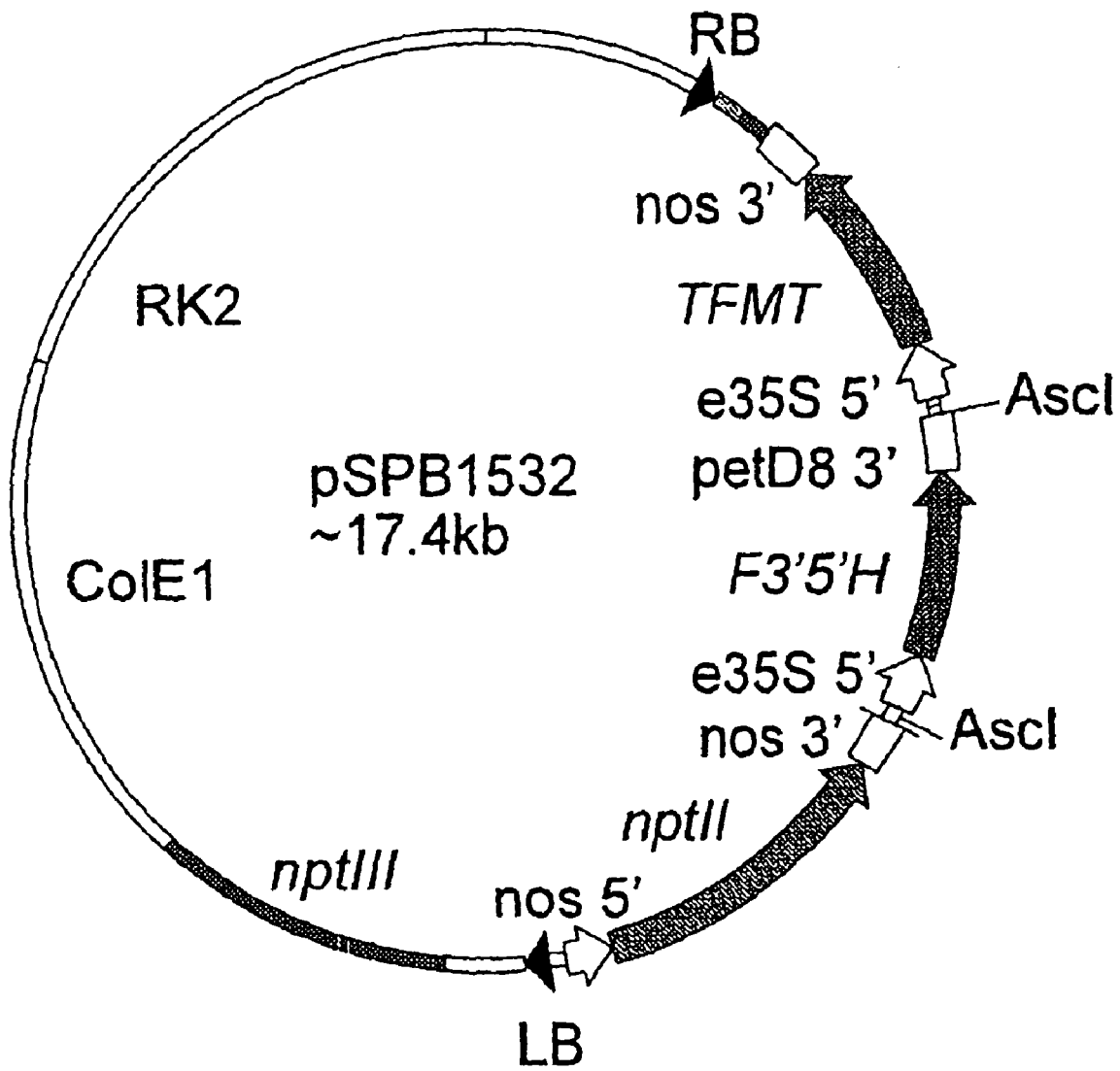
FIG. 18 is a diagrammatic representation of the binary plasmid pSPB1532. The chimaeric *Viola* F3'5'H gene from pSPB580 (FIG. 16) was cloned in a tandem orientation with the chimaeric *Petunia* FMT gene and the selectable marker gene of the Ti binary plasmid pSPB1531 (FIG. 17). Abbreviations are as follows: F3'5'H=flavonoid 3',5' hydroxylase cDNA clone from *Viola*, TFMT=*Torenia* FMT cDNA clone nptIII=the neomycin phosphotransferase III gene which confers resistance to the antibiotic kanamycin, nptII=the neomycin phosphotransferase II gene which confers resistance to the antibiotic kanamycin, e35S 5'=an enhanced promoter region from the CaMV 35S gene, petD8 3'=the terminator region from the *Petunia* PLTP gene, nos 5'=promoter region from the nopaline synthase gene of *Agrobacterium*, nos 3'=terminator region from the nopaline synthase gene of *Agrobacterium*, ColE1=*E. coli* plasmid ColE1 origin, RK2=broad host range Gram-negative plasmid RK2 origin, LB=left border, RB=right border. Selected restriction enzyme sites are also marked.

An ~3.1 kb DNA fragment containing e35S: *Viola* F3'5'H (BP#40): pet D8 3' cassette was isolated from the plasmid pSPB580 (FIG. 16) upon digestion with the restriction endonuclease AscI. The purified fragment was ligated with the AscI ends of the Ti binary plasmid pSPB1530 (FIG. 19). Correct insertion of the fragment in a tandem orientation with the *Torenia* FMT cassette and the selectable marker cassette was established by restriction endonuclease analysis of plasmid DNA isolated from kanamycin-resistant transformants. The resulting plasmid was designated pSPB1532 (FIG. 18).

Plant Transformation with PSPB1532

The binary vector plasmid pSPB1532 (FIG. 18) was introduced into *A. tumefaciens* strain AGL0 and the T-DNA contained in pSPB1532 was introduced into *Rosa hybrida* cultivars Lavande and WKS124 via *Agrobacterium*-mediated transformation.

Transgenic Analysis of Rose Petals

Independent transgenic plants were produced and grown to flowering (Table 20). Petal flower color was measured with the spectrophotometer CM-2002 (Minolta, Japan) installed with the software SpectraMagic (Minolta, Japan) in order to obtain its hue and reflectance (Tables 21, 22 and 23). Hue (0-360°) is the basic color of an object such as red, green, purple, etc., and is defined by its angular position in a cylindrical color space, or on a Color Wheel. Pure red and blue are 0 and 270 degrees, respectively. The closer the hue is to 270°, the bluer the color. Reflectance (%) is the percentage of light that is reflected from an object. Spectrophotometers measure an object's reflectance at various intervals along the visible spectrum to determine the object color's spectral curve. A lower reflectance value suggests a darker color. Royal Horticultural Society Colour Charts (RHSCC) were also used to define the color of the petals (Tables 21, 22 and 23). RNA blot analysis was performed on a selection of flowers to confirm the presence of the transgenic transcripts. HPLC analysis of the anthocyanidins accumulating in the petals of the transgenic roses was used to detect the production of the novel anthocyanins, petunidin and malvidin in rose flowers (Tables 21, 22 and 23).

TABLE 20

Number of independent transgenic rose events produced from transformation with T-DNAs contained in the plasmids pCGP3254, pSPB1532 and pSPB1534'

| Cultivar | Color | Plasmid | Genes | # | # flowered | # mod col |
|---|---|---|---|---|---|---|
| Sonia | Apricot | pCGP3254 | F3'5'H and TFMT | 36 | 8 | 5 |
| Medeo | Pale apricot | pCGP3254 | F3'5'H and TFMT | 2 | 0 | na |
| Lavande | Pink | pSPB1532 | F3'5'H and TFMT | 140 | 126 | 30 |
| WKS124 | Apricot | pSPB1532 | F3'5'H and TFMT | 90 | 75 | 75 |
| WKS124 | Apricot | pSPB1534 | F3'5'H and PFMT | 60 | 48 | 46 |

\# refers to the number of independent transgenic events produced
\# flowered refers to the number of independent events that have flowered to date
\# mod col refers to the number of independent transgenic events producing flowers with a modified petal color compared to the control Anthocyanins of the flowers of the transgenic roses were extracted and the anthocyanidins derived from the anthocyanins were analyzed by HPLC system as described in Fukui et al., (*Phytochemistry*, 47: 1409-1416, 1998). The methylated derivatives of delphinidin, malvidin and petunidin were detected in a number of flowers of transgenic roses with modified flower color (Tables 21, 22 and 23). Peonidin, the methylated derivative of cyanidin was also detected in the flowers of transgenic roses (Tables 21, 22 and 23).

TABLE 21

Levels of the anthocyanidins detected in a selection of flowers from independent transgenic events of *R. hybrida* cv. WKS124 transformed with the T-DNA in pSPB1532 containing *Viola* F3'5'H and *Torenia* FMT chimaeric genes

| code | Del (mg/g) | Cya (mg/g) | Pet (mg/g) | Pel (mg/g) | Peo (mg/g) | Mal (mg/g) | Total (mg/g) | hue | ref (%) | DPM (%) | Mal (%) | Methyl (%) | RHSCC | Petal Color |
|---|---|---|---|---|---|---|---|---|---|---|---|---|---|---|
| 5-1 | 0.22 | 0.02 | 0.18 | 0.07 | 0.06 | 0.64 | 1.19 | 341.86 | 3.51 | 92 | 57 | 78 | 72a | purple |
| 5-2 | 0.20 | 0.03 | 0.18 | 0.01 | 0.10 | 0.80 | 1.32 | 341.31 | 2.32 | 89 | 60 | 82 | 72a | red-purple |
| 7-1 | 0.45 | 0.07 | 0.32 | 0.01 | 0.14 | 0.82 | 1.81 | 352.50 | 0.89 | 88 | 45 | 71 | 61a | red-purple |
| 7-4 | 0.22 | 0.02 | 0.19 | 0.00 | 0.11 | 1.02 | 1.56 | 345.43 | 1.45 | 91 | 65 | 84 | 72a | purple |
| 12-1 | 0.13 | 0.01 | 0.11 | 0.00 | 0.07 | 0.86 | 1.18 | 343.56 | 1.49 | 93 | 73 | 88 | 78a | purple |
| 12-2 | 0.14 | 0.01 | 0.14 | 0.00 | 0.06 | 1.12 | 1.47 | 347.08 | 0.84 | 95 | 76 | 90 | 78a | purple |
| 12-3 | 0.22 | 0.03 | 0.16 | 0.00 | 0.04 | 0.27 | 0.72 | 346.05 | 2.96 | 90 | 37 | 64 | 64b | red-purple |
| 25-1 | 0.22 | 0.01 | 0.19 | 0.00 | 0.09 | 0.83 | 1.34 | 345.03 | 0.79 | 92 | 62 | 83 | 78a | purple |
| 25-2 | 0.25 | 0.01 | 0.19 | 0.00 | 0.06 | 1.24 | 1.3 | 342.77 | 0.87 | 96 | 71 | 85 | 78a | purple |
| control | 0 | 0.01 | 0 | 0.07 | 0 | 0 | 0.08 | 31.14 | 30.81 | 0 | 0 | 0 | 38b | apricot |

Code = the accession number of the transgenic plant,
Del, Cya, Pet, Pel, Peo, Mal (mg/g) refer to the amount of the specific anthocyanidin detected in mg/g where Del = delphinidin, Cya = cyanidin, Pet = petunidin, Pel = pelargonidin, Peo = peonidin, Mal = malvidin
DPM (%) = delphinidin or its methylated derivatives, petunidin and malvidin expressed as a percentage of total anthocyanidins detected
Mal (%) = malvidin expressed as a percentage of total anthocyanidins detected
Methyl (%) = methylated anthocyanidins (petunidin, peonidin, malvidin) expressed as a percentage of total anthocyanidins detected
Total = the total amounts of anthocyanidins detected (delphinidin, petunidin, malvidin, cyanidin, peonidin, pelargonidin) in mg/g
RHSCC = colors observed described according to the Royal Horticultural Society Color Charts
hue = describes the basic color in degrees as measured by a spectrophotometer with SpectraMagic software (Minolta, Japan)
Ref (%) = describes the percentage of light reflected as measured by a spectrophotometer with SpectraMagic software (Minolta, Japan)

TABLE 22

Levels of the anthocyanidins detected in a selection of flowers from independent transgenic events of *R. hybrida* cv.
Lavande transformed with the T-DNA in pSPB1532 containing *Viola* F3'5'H and *Torenia* FMT chimaeric genes

| code | Del (mg/g) | Cya (mg/g) | Pet (mg/g) | Pel (mg/g) | Peo (mg/g) | Mal (mg/g) | Total (mg/g) | hue (°) | ref (%) | DPM (%) | Mal (%) | Methyl (%) | RHSCC | Petal color |
|---|---|---|---|---|---|---|---|---|---|---|---|---|---|---|
| 13-3 | 0.13 | 0.03 | 0.04 | 0 | 0.01 | 0.04 | 0.25 | 333.81 | 19.99 | 82 | 15 | 36 | 75a | pale purple |
| 13-5 | 0.09 | 0.01 | 0.04 | 0 | 0.02 | 0.17 | 0.33 | 333.32 | 10.44 | 90 | 52 | 70 | 77b | dark purple |
| 17-1 | 0.11 | 0.05 | 0.04 | 0 | 0.07 | 0.09 | 0.36 | 344.08 | 13.07 | 67 | 26 | 57 | 186b | pink |
| 17-2 | 0.04 | 0.02 | 0.02 | 0 | 0.04 | 0.05 | 0.17 | 343.90 | 17.50 | 65 | 30 | 65 | 186c | pink |
| 24-2 | 0.02 | 0.02 | 0.01 | 0 | 0.03 | 0.03 | 0.11 | 333.23 | 29.49 | 63 | 31 | 66 | 77d | pale purple |
| 34-1 | 0 | 0.04 | 0 | 0 | 0.08 | 0 | 0.12 | 339.82 | 17.45 | 0 | 0 | 68 | 186c | pink |
| LA control | 0 | 0.08 | 0 | 0 | 0 | 0 | 0.08 | 345.25 | 16.75 | 0 | 0 | 0 | 186c | pink |

Code = the accession number of the transgenic plant,
Del, Cya, Pet, Pel, Peo, Mal (mg/g) refer to the amount of the specific anthocyanidin detected in mg/g where Del = delphinidin, Cya = cyanidin, Pet = petunidin, Pel = pelargonidin, Peo = peonidin, Mal = malvidin
DPM (%) = delphinidin or its methylated derivatives, petunidin and malvidin expressed as a percentage of total anthocyanidins detected
Mal (%) = malvidin expressed as a percentage of total anthocyanidins detected
Methyl (%) = methylated anthocyanidins (petunidin, peonidin, malvidin) expressed as a percentage of total anthocyanidins detected
Total = the total amounts of anthocyanidins detected (delphinidin, petunidin, malvidin, cyanidin, peonidin, pelargonidin) in mg/g
RHSCC = colors observed described according to the Royal Horticultural Society Color Charts
hue = describes the basic color in degrees as measured by a spectrophotometer with SpectraMagic software (Minolta, Japan)
Ref (%) = describes the percentage of light reflected as measured by a spectrophotometer with SpectraMagic software (Minolta, Japan)

TABLE 23

Levels of the anthocyanidins detected in a selection of flowers from independent transgenic events of *R. hybrida* cv.
WKS124 transformed with the T-DNA in pSPB1534 containing *Viola* F3'5'H and *Petunia* FMT chimaeric genes

| code | Del (mg/g) | Cya (mg/g) | Pet (mg/g) | Pel (mg/g) | Peo (mg/g) | Mal (mg/g) | Total (mg/g) | hue (°) | ref (%) | DPM (%) | Mal (%) | Methyl (%) | RHSCC | Petal Color |
|---|---|---|---|---|---|---|---|---|---|---|---|---|---|---|
| 02-2 | 0.44 | 0.06 | 0.01 | 0.02 | 0 | 0 | 0.53 | 347.53 | 10.15 | 85 | 0.0 | 2 | 64c | red-purple |
| 02-3 | 0.59 | 0.09 | 0.01 | 0.01 | 0 | 0 | 0.7 | 346.64 | 8.51 | 85 | 0.0 | 2 | 64c | red-purple |
| 07-1 | 0.91 | 0.10 | 0.02 | 0.03 | 0 | 0 | 1.06 | 352.44 | 7.26 | 87 | 0.0 | 2 | 71b | red-purple |
| 08-3 | 1.76 | 0.06 | 0.03 | 0.00 | 0 | 0 | 1.85 | 350.34 | 1.56 | 97 | 0.0 | 2 | 61b | red-purple |
| 08-6 | 1.34 | 0.06 | 0.03 | 0 | 0 | 0 | 1.43 | 354.15 | 1.11 | 96 | 0.0 | 2 | 61a | red-purple |
| 08-7 | 1.22 | 0.11 | 0.02 | 0.01 | 0 | 0 | 1.36 | 351.48 | 1.55 | 92 | 0.0 | 2 | 64b | red-purple |
| 11-2 | 1.60 | 0.17 | 0.02 | 0.01 | 0 | 0 | 1.80 | 357.44 | 1.14 | 90 | 0.0 | 1 | 61a | red-purple |
| 14-3 | 1.35 | 0.10 | 0.03 | 0.00 | 0 | 0 | 1.48 | 352.54 | 2.58 | 93 | 0.0 | 2 | 64b | red-purple |
| 14-5 | 1.11 | 0.04 | 0.03 | 0 | 0 | 0 | 1.18 | 352.52 | 1.78 | 97 | 0.0 | 2 | 64b | red-purple |
| 15-1 | 1.04 | 0.04 | 0.02 | 0 | 0 | 0 | 1.10 | 351.85 | 1.72 | 97 | 0.0 | 2 | 64b | red-purple |
| 15-2 | 1.25 | 0.06 | 0.03 | 0 | 0 | 0 | 1.34 | 347.89 | 3.77 | 96 | 0 | 2 | 64b | red-purple |
| control | 0 | 0.01 | 0 | 0.07 | 0 | 0 | 0.08 | 31.14 | 30.81 | 0 | 0 | 0 | 38b | apricot |

Code = the accession number of the transgenic plant,
Del, Cya, Pet, Pel, Peo, Mal (mg/g) refer to the amount of the specific anthocyanidin detected in mg/g where Del = delphinidin, Cya = cyanidin, Pet = petunidin, Pel = pelargonidin, Peo = peonidin, Mal = malvidin
DPM (%) = delphinidin or its methylated derivatives, petunidin and malvidin expressed as a percentage of total anthocyanidins detected
Mal (%) = malvidin expressed as a percentage of total anthocyanidins detected
Methyl (%) = methylated anthocyanidins (petunidin, peonidin, malvidin) expressed as a percentage of total anthocyanidins detected
Total = the total amounts of anthocyanidins detected (delphinidin, petunidin, malvidin, cyanidin, peonidin, pelargonidin) in mg/g
RHSCC = colors observed described according to the Royal Horticultural Society Color Charts
hue = describes the basic color in degrees as measured by a spectrophotometer with SpectraMagic software (Minolta, Japan)
Ref (%) = describes the percentage of light reflected as measured by a spectrophotometer with SpectraMagic software (Minolta, Japan)

RNA Blot Analysis

Flowers of 7 transgenic WKS124/pSPB1532 plants (lines 5-1, 5-2, 7-1, 7-4, 12-1, 12-3) and 7 transgenic Lavande/1532 plants (lines 13-2, 13-3, 13-5, 17-1, 24-2, 34-1) along with flowers from non transgenic WKS124 and Lavande controls were analysed for the presence of transcripts of the introduced *Viola* F3'5'H and *Torenia* FMT transgenes.

Total RNA was isolated from transgenic rose petals with using RNAeasy (Qiagen) following the manufacturer's protocol. Twenty µg of RNA was separated through 1.2% agarose gel and blotted to Hybond-N (Amersham) following the Instruction Manual of DIG Northern Starter Kit (Roche). RNA probes that hybridized with mRNA of *Viola* F3'5'H (BP#40) and *Torenia* FMT were prepared using the plasmids, pCGP1961 (containing the *Viola* F3'5'H (BP#40) cDNA clone) (Australian Provisional Patent Applications No. 2002951088 and 2002952835, 2002, supra) and pTMT5 (FIG. 8) that had each been digested with the restriction endonuclease BamHI, as the transcription template and the T7 oligonucleotide as the transcription primer following the Instruction Manual of DIG Northern Starter Kit (Roche). Further hybridization and detection were also carried out following the Instruction Manual of DIG Northern Starter Kit (Roche).

Under the conditions used, ~1.7 kb transcripts were detected with the *Viola* F3'5'H probe in most of the lines analysed except for line 34-1 (Lavande/pSPB1532). A ~1.0 kb transcript was detected with the TFMT probe in all 14 transgenic lines analysed. Under the conditions used, no hybridising transcripts were detected in the control petals of WKS124 and Lavande with the *Viola* F3'5'H and TFMT probes.

WKS124 Transgenic Roses

The rose cultivar WKS124 generally produces apricot flowers (RHSCC 38b). HPLC analysis of the anthocyanidins reveal that pelargonidin (0.07 mg/g pelargonidin) is the predominant anthocyanidin accumulating with low levels of cyanidin present also (0.01 mg/g cyanidin) (Table 21).

Introduction of the *Viola* F3'5'H chimaeric gene along with the *Torenia* FMT had a dramatic impact on the color of the flowers produced and on the anthocyanidin composition in the petals. In a selection of petals with the most dramatic color change, the 3'5' hydroxylated pigments (delphinidin, petunidin and malvidin) predominated, with malvidin being the most predominant anthocyanin (Table 21).

Introduction of the *Viola* F3'5'H chimaeric gene along with the *Petunia* FMT led to the production of the 3'5' hydroxylated anthocyanidin, delphinidin in a selection of rose petals. The activity of the introduced *Viola* F3'5'H led to the production of relatively high levels of delphinidin (Table 23). However the resulting activity of the introduced *Petunia* FMT in the WKS124 rose petals was low and only a small amount of the methylated anthocyanidin, petunidin accumulated (Table 23). It may be that the physiological conditions within the WKS124 rose petal are not ideal for the *Petunia* FMT to work efficiently.

Production of predominantly delphinidin pigments in a petal background of WKS124 (WKS124/pSPB1534) led to an increase in the total anthocyanidins produced (from 0.08 mg/g in the control flowers to 0.5-1.9 mg/g in the transgenic flowers). This production of predominantly delphinidin pigments in WKS124 petals resulted in a change of color from apricot (control flower) to colors in the dark pink to red-purple ranges (Table 23). A similar increase in total anthocyanidins was observed in the transgenic WKS124/pSPB1532 petals (Table 21). However, the delphinidin produced was converted to the methylated petunidin and malvidin-based pigments and this led to a further bluing of flower color into the purple range of colors, resulting in novel colored rose flowers.

The hue values of WKS124/1532 petals are generally closer than those of WKS/1534 petals to 270°, which indicate that malvidin production or methylation of anthocyanins contributes to bluing of flower color. In other words, FMT genes are useful to modify flower colors, especially, but not limited, toward blue.

The reflectance values of WKS124/1532 petals are generally lower than those of WKS/1534 petals, which indicate that malvidin production or methylation of anthocyanins contributes to darkening of flower color. In other words, FMT genes are useful to modify flower colors, especially, but not limited, toward darker color. Besides with these flower color changes, WKS124/1532 lines accumulating large amounts of malvidin were more vivid and brilliant in appearance. Such flower color modification is also exhibited by changes of RHSCC. These results clearly demonstrate that FMT genes are useful to modify flower color.

Lavande Transgenic Roses

The rose cultivar Lavande generally produces pink flowers (RHSCC 186c). HPLC analysis of the anthocyanidins reveal that cyanidin (0.08 mg/g cyanidin) is the predominant anthocyanidin accumulating (Table 22).

Introduction of the *Viola* F3'5'H chimaeric gene along with the *Torenia* FMT had a dramatic impact on the color of the transgenic Lavande flowers produced and on the anthocyanidin composition in the petals. In a selection of petals with the most dramatic color change, the 3'5' hydroxylated pigments (delphinidin, petunidin and malvidin) predominated, with malvidin being the most predominant anthocyanin (Table 22).

Introduction of the *Viola* F3'5'H and *Torenia* FMT genes in Lavande led to an increase in the total level of anthocyanidins accumulating in rose petals (from 0.08 mg/g in the control flowers to 0.11-0.36 mg/g in the transgenics) (Table 22).

In this petal background the most dramatic color change and shift to blue (to purple colour 77b) was observed in a flower containing a high proportion (90% of its total anthocyanidins) of delphinidin-based pigments (delphinidin, petunidin and malvidin) with 52% of the total anthocyanidins accumulating being malvidin.

In line 34-1 (Table 22), delphinidin was not produced indicating lack of activity of the introduced F3'5'H gene. RNA blot analysis revealed no hybridising *Viola* F3'5'H transcript in this line. However, a strongly hybridising *Torenia* FMT transcript was detected and the *Torenia* FMT activity was confirmed by the production of peonidin (the methylated derivative of cyanidin). This result highlighted that the *Torenia* FMT was also able to methylate cyanidin-based pigments.

Example 12

Isolation of FMT cDNA Clones from *Fuchsia* spp

PCR of FMT Sequences from *Fuchsia*

CODEHOP Design of Primers for PCR of FMT Sequences from *Fuchsia*

In order to isolate FMT sequences from *Fuchsia*, oligonucleotide primers were designed to areas of amino acid sequence similarity between the *Petunia* FMT (this specification) and published (GenBank database) caffeoyl CoA OMTs (*V. vinifera* (Z54233), *S. longipes* (L22203), *P. tremuloides* (U27116), *P. kitakamiensis* (AB00048), *P. crispum* (Z54183), *E. gunnii* (Y12228), *N. tabacum* (U38612), *M. crystallinum* (AF053553), *A. thaliana* (L40031)).

The CODEHOP (COnsensus-DEgenerate Hybrid Oligonucleotide Primers) strategy (Rose et al., *Nucl Acids Res*, 26: 1628-1635, 1998) was used. The CODEHOP program designs a pool of primers containing all possible 11- or 12-mers for a 3' degenerate "core" region and having the most probable nucleotide predicted for each position in a 5' non-degenerate "clamp" region (Table 24).

TABLE 24

Oligonucleotides designed to areas of sequence similarity between methyltransferase sequences identified by the CODEHOP program

| SEQ ID NO: | PRIMER | SEQUENCE (5' TO 3') |
|---|---|---|
| 15 | OMTIf2 | ACC ATC GAG ATC GGC GTN TTY CAN GG |
| 16 | OMTIf4 | CGA CTT CGC CTT CGT GGA YGC NGA YAA |
| 17 | OMTIr3 | TGA AGT TGA TCT TGT GCT CCA CNC CNG CYT T |
| 18 | OMTIr5 | CGC CGG CAG AAG GTG ANN CCR TCN CC | where R = A or G, Y = C or T, M = A or C, K = G or T, S = G or C, W = A or T, H = A or C or T, B = G or C or T, V = A or G or C, D = A or G or T, N = A or G or C or T, I = deoxyinosine.

TABLE 25

Other oligonucleotides designed for use in PCR
of FMT sequences

| SEQ ID NO: | PRIMER | SEQUENCE (5' TO 3') |
|---|---|---|
| 19 | dT(17) Ad2Ad1 | CTG AGA GAA CTA GTC TCG AGC TCT AGA ACA AGC TTT TTT TTT TTT |
| 20 | GI-anchor | GGC CAC GCG TCG ACT AGT ACG GGI IGG GII GGG IIG |
| 27 | Ad1 | CTG AGA GAA CTA GTC TCG AG |

I = deoxyinosine

Total RNA was isolated from *Fuchsia* petal buds using the Plant RNAeasy kit (QIAGEN). One microgram of RNA was used as a template to synthesize cDNA using Superscript II (Stratagene) and the dT(17)Ad2Ad1 [SEQ ID NO: 19] (Table 25) oligonucleotide under conditions as recommended by the manufacturer. The cDNA was purified by passing it through a PCR purification column (QIAGEN) and eluting in 50 µL 10 Mm Tris-HCl, pH 8.5. The cDNA was subsequently C-tailed using Calf Thymus terminal transferase (Boehringer Mannheim) using conditions recommended by the manufacturer. The C-tailed cDNA was then purified through a PCR purification column (QIAGEN) and eluted in 50 µL 10 µM Tris-HCl, pH 8.5.

The C-tailed cDNA (1 µL) was subsequently used as template in a PCR with 2.5 µL 10× HotSTAR™ Taq QIAGEN buffer, 4 µL 1.25 mM dNTP, 5 µL 50 ng/µL primer OMTIf2 [SEQ ID NO: 15], 5 µL 50 ng/µL Ad1 primer [SEQ ID NO: 27] (Table 25), 2 µL pure water and 0.5 µL HotSTAR™ Taq DNA polymerase (QIAGEN). The reaction was heated to 95° C. for 15 minutes then run through 35 cycles of 94° C. for 30 seconds, 50° C. for 30 seconds, 72° C. for 90 seconds, followed by 72° C. for 10 minutes.

The PCR products were electrophoresed through a 1% w/v agarose gel and expected products of around 0.8 kb in length were excised, purified and ligated with pCR 2.1 (Invitrogen). A random selection of transformants was analysed for the presence of inserts by digesting with the restriction endonuclease EcoRI. Transformants containing inserts of 0.8 kb were sequenced using the M13 Reverse and M13 Forward-21 primers. An example of resulting *Fuchsia* sequences showing similarity to FMTs is found in the plasmid designated pCGP3267 (FIG. 21).

The *Fuchsia* FMT (SEQ ID NO: 21) contained in pCGP3267 showed 66% and 64% identity at the nucleotide level with the *Petunia* [SEQ ID NO:4] and *Torenia* FMT ] SEQ ID NO:11] when comparing the coding sequence corresponding only with the length of the partial *Fuchsia* FMT clone. The deduced amino acid sequence of encoded by the *Fuchsia* FMT clone in pCGP3267 showed 81% similarity with both the *Petunia* [SEQ ID NO:5] and *Torenia* FMT [SEQ ID NO:12] again considering only the region comparable to the length of the partial *Fuchsia* clone.

Generation of Full-Length *Fuchsia* FMT Clone

Figure 21:
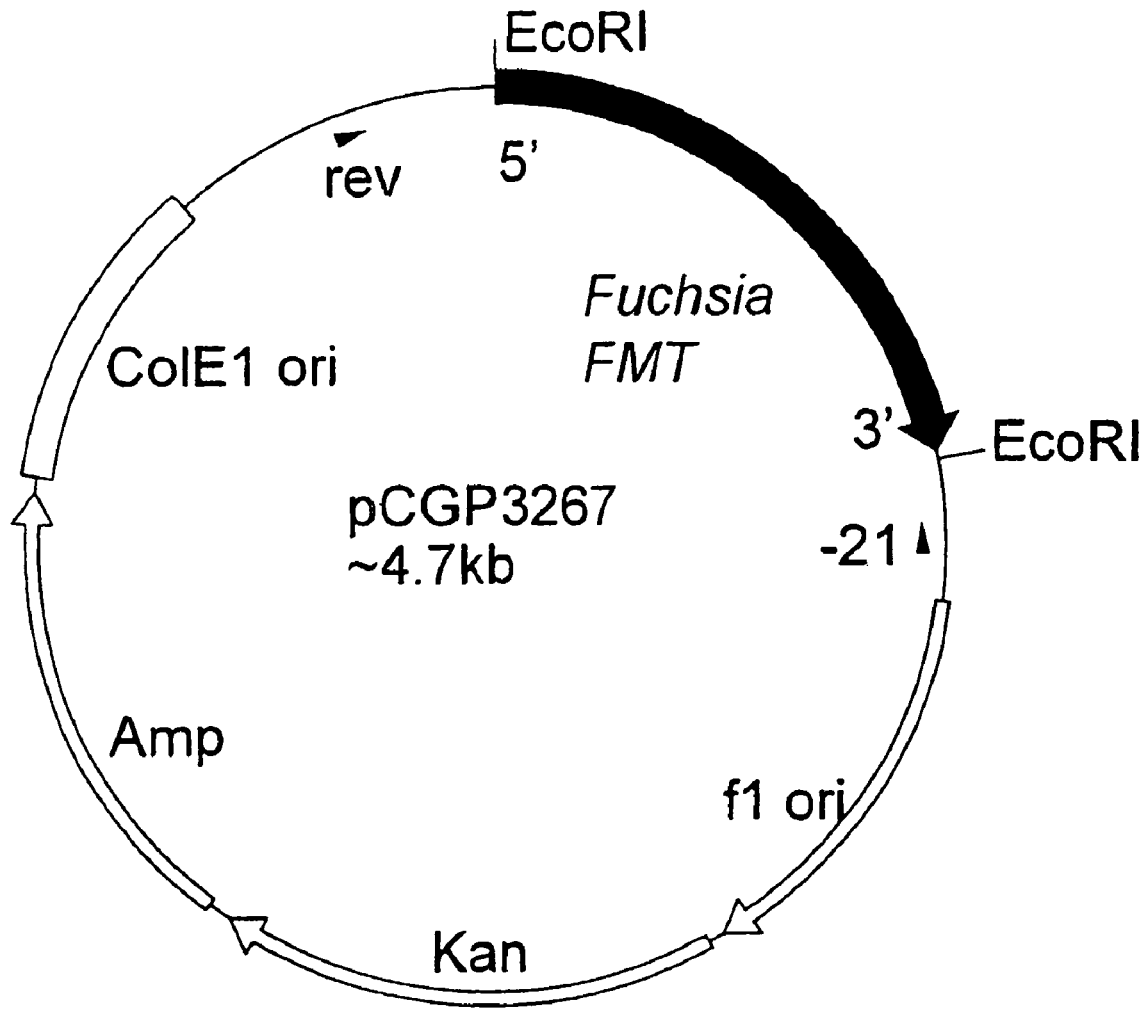
FIG. 21 is a diagrammatic representation of the plasmid pCGP3267. A partial clone of *Fuchsia* FMT was amplified using PCR and single stranded cDNA (prepared from total RNA isolated from *Fuchsia* petals) as template and cloned into the plasmid pCR2.1. Abbreviations are as follows: Amp=the ampicillin resistance gene which confers resistance to the antibiotic tetracycline, Kan=the kanamycin resistance gene which confers resistance to the antibiotic kanamycin, f1 ori (+)=f1 filamentous phage origin of replication, ColE1 ori=plasmid origin of replication, rev=approximate location of the M13 reverse primer site used in sequence analysis, −21=approximate location of the M13-21 primer site used in sequence analysis. Selected restriction enzyme sites are also marked.

A genomic strategy was employed to generate sequence upstream of the *Fuchsia* FMT cDNA clone [SEQ ID NO: 21] contained in the plasmid pCGP3267 (FIG. 21).

Isolation of Genomic DNA from *Fuchsia*

Plasmid Genomic Library Construction

Genomic DNA (gDNA) was extracted from 1 g of fresh, young leaf material of *Fuchsia hybrida* cultivar Derby Imp using the Qiagen DNeasy maxi kit and following the manufacturers instructions. Approximately 1.2 µg of gDNA was then digested with the restriction endonuclease, TaqI. The digested genomic DNA fragments were then ligated (using Amersham ligation kit) with dephosphorylated EcoRV ends of the vector pBluescript II (Stratagene). The ligation mix was then used as a template in PCR.

The primer OMTIf1 [SEQ ID NO: 23] along with the primer FucR1 [SEQ ID NO: 34] (Table 26) that was designed to the *Fuchsia* FMT cDNA clone contained in pCGP3267 were used in a PCR using *Fuchsia* genomic DNA as template. The amplified products were purified and ligated into the vector pCR2.1. Sequence analysis of a 274 bp fragment (designated as the "OMTIf1/FucR1 amplified fragment") revealed that this fragment included 51 bp of overlapping sequence with the *Fuchsia* FMT cDNA clone in the plasmid pCGP3267, a further 74 bp of new coding sequence upstream of this point, an intron that was 88 bp in length and a further 61 bp of new coding sequence upstream from the intron.

Further to this a nested primer pair combination (FucR5 [SEQ ID NO:36] and FucR6 [SEQ ID NO:37] was then designed to the sequence that was upstream from the intron. The primers FucR5 [SEQ ID NO:36] and FucR6 [SEQ ID NO:37] were used on *Fuchsia* gDNA that had been digested with the restriction endonuclease, TaqI. The products that were amplified were ligated with the AccI ends of the vector pBluescript KS (Stratagene). A first round of amplification by PCR was performed using the primers FucR5 [SEQ ID NO:36] and M13rev (NEB) and *Fuchsia* gDNA as template. The products were purified using a Qiaquick column (QIAGEN) and then added as template to the second round of PCR amplification with the primers FucR6 [SEQ ID NO:36] and T3 (Stratagene). The amplified products were purified and ligated into the vector pCR2.1. Sequence analysis of a 247 bp fragment (designated "FucR6/T3 amplified fragment") revealed a further 24 bp of new coding sequence upstream of that obtained with the "OMTIf1/FucR1 amplified fragment". The remainder of the sequence consisted of another intron that was 223 bp in length and no further coding sequence could be identified upstream of this. A further 51 to 54 bp of sequence (i.e. 17 or 18 amino acids) were required to reach the presumed methionine start as determined by comparison with the *Torenia* and *Petunia* FMT sequences. Therefore, a strategy was developed to utilize the 5' sequence of the *Torenia* FMT cDNA clone and ligate this with the longest *Fuchsia* FMT PCR product to generate a full-length and functional *Fuchsia* FMT cDNA clone.

A primer (FucF1) [SEQ ID NO:38] was designed to the 5'end of the coding sequence found in the FucR6/T3 amplified fragment (described above). The FucF1 primer [SEQ ID NO:38] and the Ad1 primer [SEQ ID NO:27] were used in a PCR with *Fuchsia* cDNA as template (synthesis of *Fuchsia* cDNA described above). The amplified product was cloned into pCR2.1 and the resulting plasmid was designated pCGP3282. The plasmid pCGP3282 was used as template in a PCR with the Ad1 [SEQ ID NO:27] and Tor-5'pos [SEQ ID NO: 39] primers and Taq DNA polymerase HotSTAR taq (QIAGEN). The use of the Taq DNA polymerase, HotSTAR taq (QIAGEN) leaves a 3'-A overhang on the amplified product. The resulting amplified product (defined as "Tor-5' pos/Ad1 amplified fragment") was then digested with the restriction endonuclease, SpeI. (an SpeI recognition sequence is located within the Ad1 primer at the 3' end of the cDNA clone).

Figure 22:
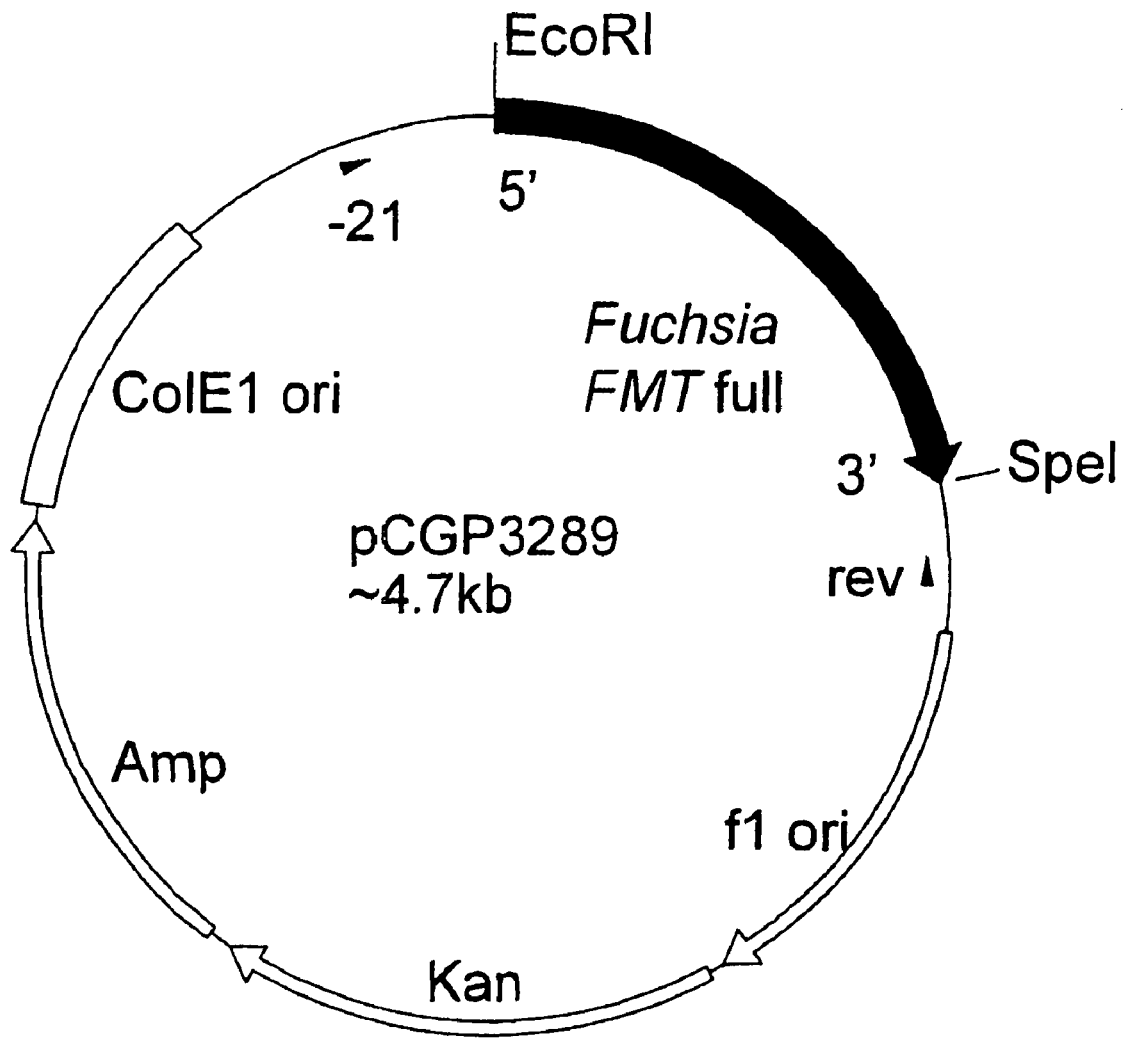
FIG. 22 is a diagrammatic representation of the plasmid pCGP3289. A full-length version of *Fuchsia* FMT (*Fuchsia* FMT full) was cloned into the plasmid pCR2.1. Abbreviations are as follows: Amp=the ampicillin resistance gene which confers resistance to the antibiotic ampicillin, Kan=the kanamycin resistance gene which confers resistance to the antibiotic kanamycin, f1 ori (+)=f1 filamentous phage origin of replication, ColE1 ori=plasmid origin of replication, rev=approximate location of the M13 reverse primer site used in sequence analysis, −21=approximate location of the M13-21 primer site used in sequence analysis. Selected restriction enzyme sites are also marked.

The primers Tor-5'pos [SEQ ID NO:39] and Tor-5'neg [SEQ ID NO:40] were annealed together upon incubation at 75° C. for 5 minutes, followed by a slow cooling down to 37° C. over 30 minutes. These primers were designed so that once annealed there would be a "T" overhang at the 3' end of the sequence and sequence overhang compatible with an EcoRI recognition sequence at the 5'-end. The annealed oligonucleotide were ligated with the SpeI ends of the "Tor-5' pos/Ad1 amplified fragment". This ligated products were then used as template in a PCR using the oligonucleotides Tor-5'pos [SEQ ID NO:39] and Ad1 [SEQ ID NO:27] as primers. The PCR product was then ligated with the cloning vector pCR2.1. The resulting plasmid was designated pCGP3289 (FIG. 22).

The *Fuchsia* FMT [SEQ ID NO: 43] contained in pCGP3289 showed 51%, 48% and 56% identity at the nucleotide level with the *Petunia* E20 [SEQ ID NO:4], *Petunia* E33 [SEQ ID NO:26] and *Torenia* FMT [SEQ ID NO:11], respectively. The deduced amino acid sequence encoded by the *Fuchsia* FMT clone in pCGP3289 [SEQ ID NO:44] showed 67%, 80% and 82% similarity with the *Petunia* E20 [SEQ ID NO:5], *Petunia* E33 [SEQ ID NO:7] and *Torenia* FMT [SEQ ID NO:12], respectively.

TABLE 26

Primers

| SEQ ID NO: | NAME | SEQUENCE 5' TO 3' |
|---|---|---|
| 34 | FucR1 | GCA AGT GCA GTG CAA AGA AGA G |
| 35 | FucR3 | GAT CTT ATG TTC CAC TCC GC |
| 36 | FucR5 | GAG AGA TCT GAC CAG TAA GG |
| 37 | FucR6 | GGA TAT TTT TCG GCC GTG ACC TCC |
| 38 | FucF1 | ATC TTA GAG ACG ACT GCT TAT CCC |
| 39 | Tor-5'pos | AAT TCG CAG CAA AAA TGA AGA ATA AGT TCT ATG GCA CCA TTT TGC AGA GCG AAG CCC TCG CAA AGT AT |
| 40 | Tor-5'neg | TAC TTT GCG AGG GCT TCG CTC TGC AAA ATG GTG CCA TAG AAC TTA TCT TTC ATT TTT GCT GCG |

Construction of pCGP3292 (35S 5': FFMT: 35S 3'; 35S 5': *Viola* F3'5'H: 35S 3': 35S 5': SuRB Binary Vector)

The binary plasmid pCGP3292 (FIG. 25) was constructed to allow the production of methylated delphinidin derivatives such as petunidin and malvidin in a line that does not normally produce delphinidin-based pigments and does not contain a flavonoid methyltransferase capable of methylating delphinidin-based anthocyanins.

The binary plasmid pCGP3292 (FIG. 25) contains a 35S 5': FFMT: 35S 3' expression cassette (from the plasmid pCGP3290 (FIG. 23)) and a 35S 5': *Viola* F3'5'H: 35 3' expression cassette, both in tandem with the 35S 5'. SuRB selectable marker cassette of the Ti binary vector of pCGP1988 (FIG. 12).

Construction of Intermediate Plasmids (i) Construction of pCGP3290 (35S 5': FFMT: 35S 3'Expression Cassette)

The plasmid pCGP3290 (FIG. 23) was constructed by cloning the *Fuchsia* FMT (FFMT) cDNA clone from pCGP3289 (FIG. 22) into a CaMV 35S expression cassette.

The plasmid pRTppoptcAFP was used as a source of a CaMV 35S promoter and terminator fragments. It was initially digested with the restriction endonuclease XbaI, the overhanging 5' ends were repaired and then the plasmid was digested with the restriction endonuclease EcoRI to release the 3.3 kb vector containing the CaMV 35S expression cassette. The 3.3 kb fragment was isolated and purified.

Figure 23:
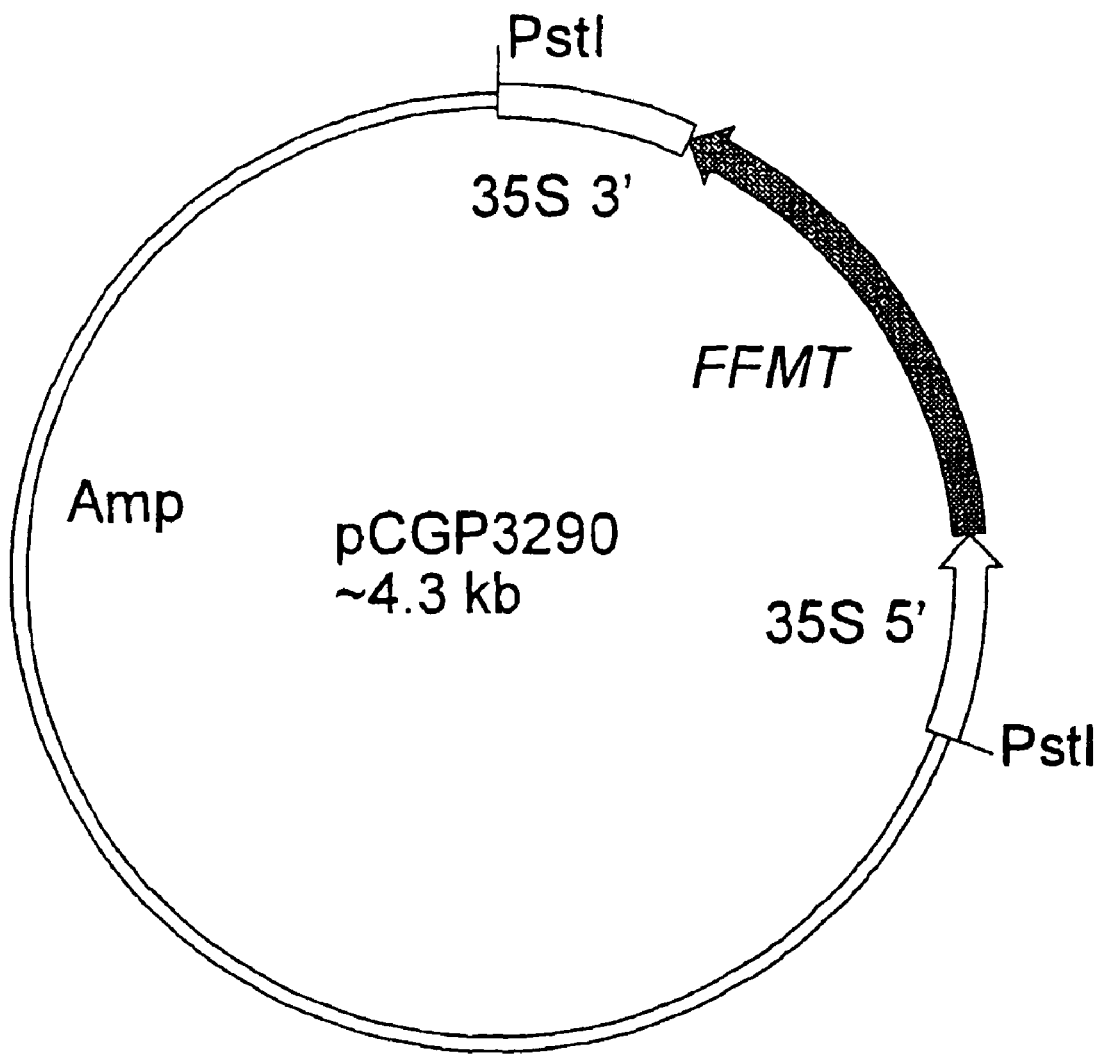
FIG. 23 is a diagrammatic representation of the plasmid pCGP3290. The *Fuchsia* FMT cDNA clone (FFMT) from pCGP3289 (FIG. 22) was cloned into a CaMV 35S expression cassette. Abbreviations are as follows: Amp=Amp=the ampicillin resistance gene which confers resistance to the antibiotic ampicillin, 35S 5'=the promoter region from the CaMV 35S gene, 35S 3'=the terminator region from the CaMV 35S gene. Selected restriction enzyme sites are also marked.

The plasmid pCGP3289 (FIG. 22) was digested initially with the restriction endonuclease SpeI and the resulting 5' overhang ends were repaired. The linearized plasmid was then restricted with the restriction endonuclease EcoRI to release a 1.0 kb *Fuchsia* FMT cDNA fragment which was isolated, purified and then ligated with the XbaI (blunt)/EcoRI ends of the pRTppoptc vector (described above). Correct ligation of the fragments was established by restriction endonuclease analysis (HinDIII, XhoI, and PstI) of plasmid DNA isolated from ampicillin-resistant transformants. The resulting plasmid was designated pCGP3290 (FIG. 23).

(ii) Construction of pCGP2788 (35S 5': *Viola* F3'5'H: 35S 3'; 35S 5': SuRB Binary Vector)

The binary plasmid pCGP2788 (FIG. 24) contains the 35S 5': *Viola* F3'5'H: 35S 3' expression cassette (from pCGP3254 (FIG. 13) in tandem with the 35S 5': SuRB selectable marker cassette of the Ti binary plasmid pCGP1988 (FIG. 12).

The binary plasmid pCGP3254 (FIG. 13) was digested with the restriction endonuclease PstI to release the 35S 5'. *Torenia* FMT: 35S 3' expression cassette and the expression binary vector backbone. The resulting fragments were ethanol precipitated (Sambrook et al., 1989, supra) and the mixture of fragments was religated. Correct ligation of the vector backbone containing the 35S 5': SuRB gene and the chimaeric *Viola* F3'5'H gene without the 35S 5': *Torenia* FMT: 35S 3' cassette was established by restriction endonuclease analysis (HinDIII, EcoRV, PstI, EcoRI, and NcoI) of plasmid DNA isolated from tetracycline-resistant transformants. The resulting plasmid was designated pCGP2788 (FIG. 24).

Construction of PCGP3292 (35S 5': FFMT: 35S 3': 35S 5': *Viola* F3'5'H: 35S 3'; 35S 5': SuRB Expression Binary)

Figure 24:
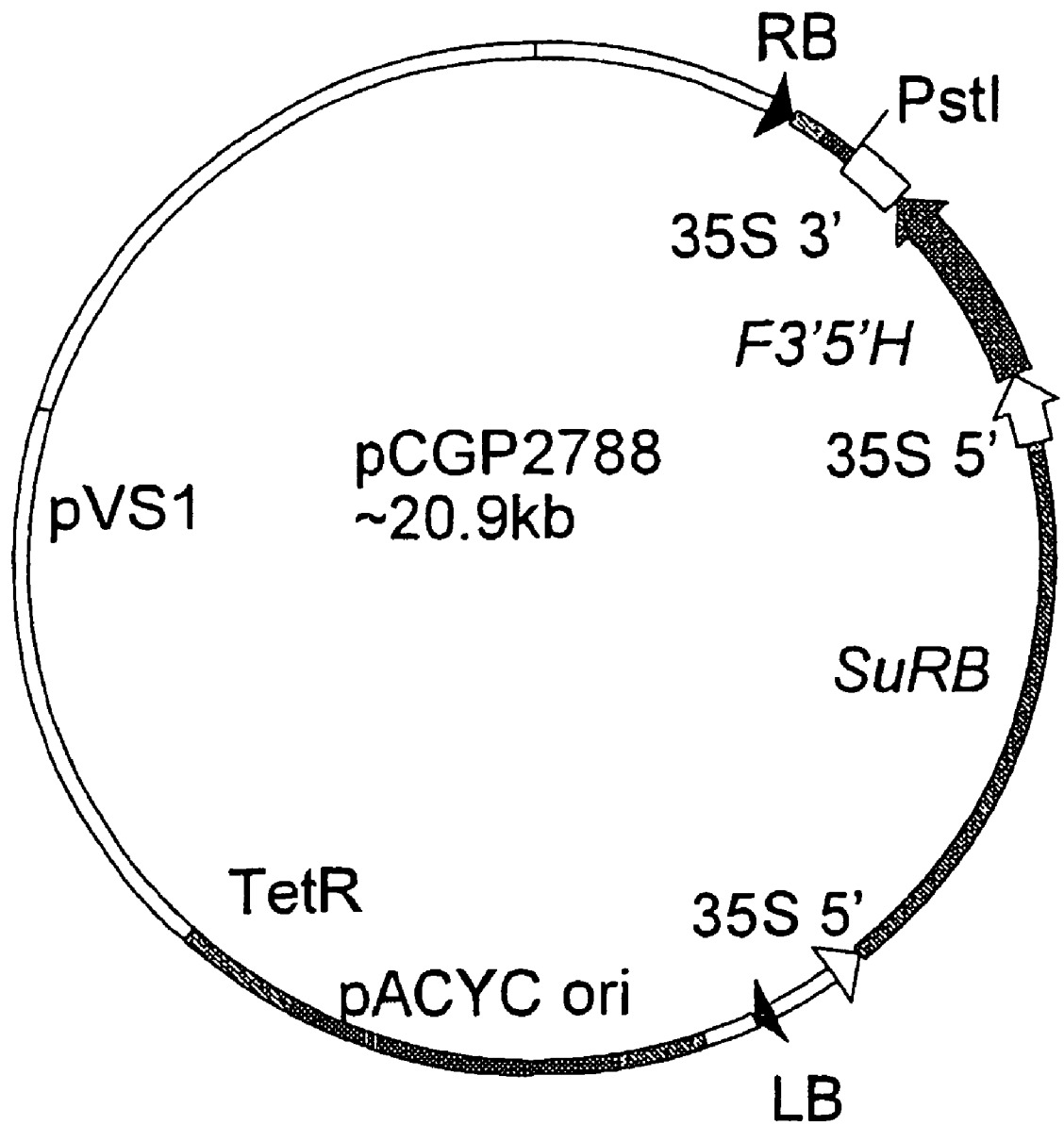
FIG. 24 is a diagrammatic representation of the binary plasmid pCGP2788. The 35S 5': *Torenia* FMT: 35S 3' expression cassette was removed from the binary plasmid pCGP3254 (FIG. 13) to leave a binary vector with the 35S 5': *Viola* F3'5'H: 35S 3' expression cassette in tandem with the 35S 5': SuRB selectable marker gene. Abbreviations are as follows: F3'5'H=flavonoid 3',5' hydroxylase cDNA clone from *Viola*, TetR=the tetracycline resistance gene which confers resistance to the antibiotic tetracycline; LB=left border; RB=right border; SuRB=the coding region and terminator sequence from the acetolactate synthase gene from tobacco; 35S 5'=the promoter region from the CaMV 35S gene, 35S 3'=the terminator region from the CaMV 35S gene, pVS1=a broad host range origin of replication from a plasmid from *Pseuodomonas aeruginosa*, pACYC ori=modified replicon from pACYC184 from *E. coli*. Selected restriction enzyme sites are also marked.

Plasmid pCGP3292 (FIG. 25) was constructed by cloning the chimaeric *Fuchsia* FMT gene from pCGP3290 (FIG. 23) into the Ti binary vector pCGP2788 (FIG. 24).

Figure 25:
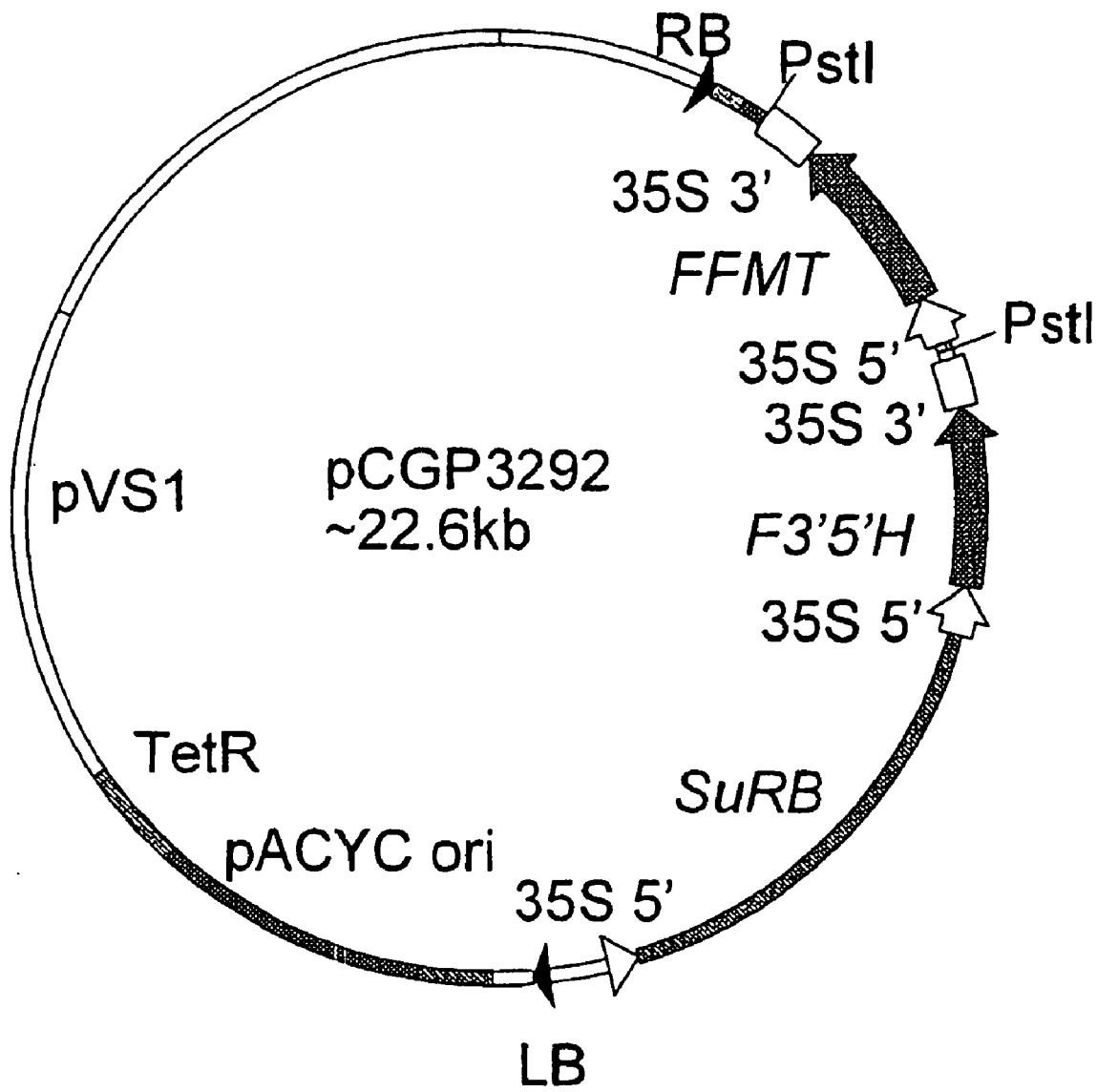
FIG. 25 is a diagrammatic representation of the binary plasmid pCGP3292. The 35S 5': FFMT: 35S 3' expression cassette from pCGP3290 (FIG. 23) was cloned in a tandem orientation to the 35S 5': SuRB and 35S 5': F3'5'H: 35S 3' expression cassettes of the Ti binary plasmid pCGP2788 (FIG. 24). Abbreviations are as follows: F3'5'H=flavonoid 3',5' hydroxylase cDNA clone from *Viola*, FFMT=*Fuchsia* FMT cDNA clone, TetR=the tetracycline resistance gene which confers resistance to the antibiotic tetracycline; LB=left border; RB=right border; SuRB=the coding region and terminator sequence from the acetolactate synthase gene from tobacco; 35S 5'=the promoter region from the CaMV 35S gene, 35S 3'=the terminator region from the CaMV 35S gene, pVS1=a broad host range origin of replication from a plasmid from *Pseuodomonas aeruginosa*, pACYC ori=modified replicon from pACYC184 from *E. coli*. Selected restriction enzyme sites are also marked.
Figure 26A:
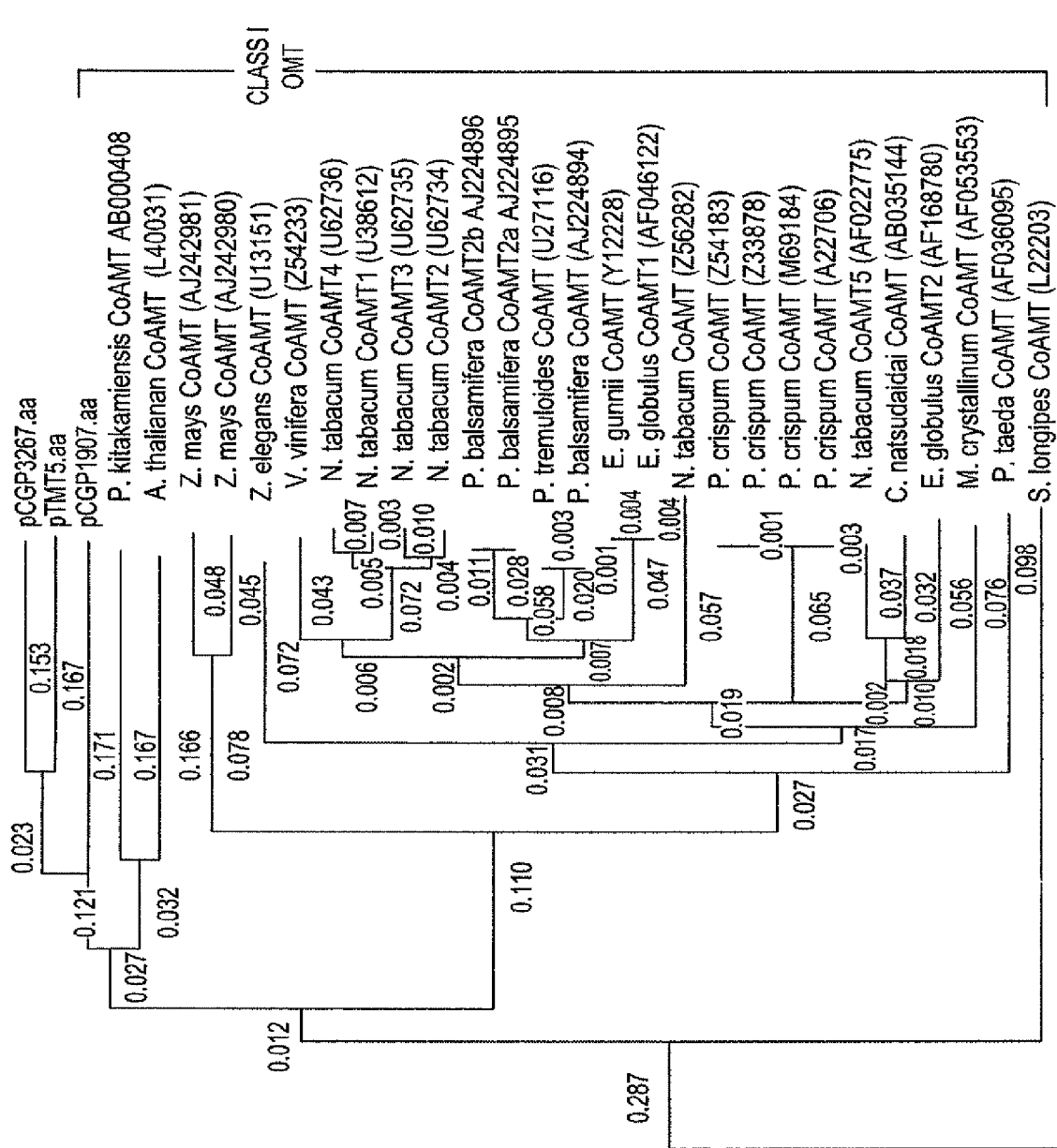
FIGS. 26A-26D when joined at match lines show a dendogram that illustrates the clustering relationship between deduced amino acid sequences of petunia (pCGP1907.aa), Torenia (pTMT5.aa) and *Fuchsia* (pCGP3267.aa) FMTs with other full length plant O-methyltransferases (OMT) of both Class I and Class II found in the GenBank database. The Genbank accession numbers of each SAM-OMT in the database are shown in brackets.
Figure 26B:
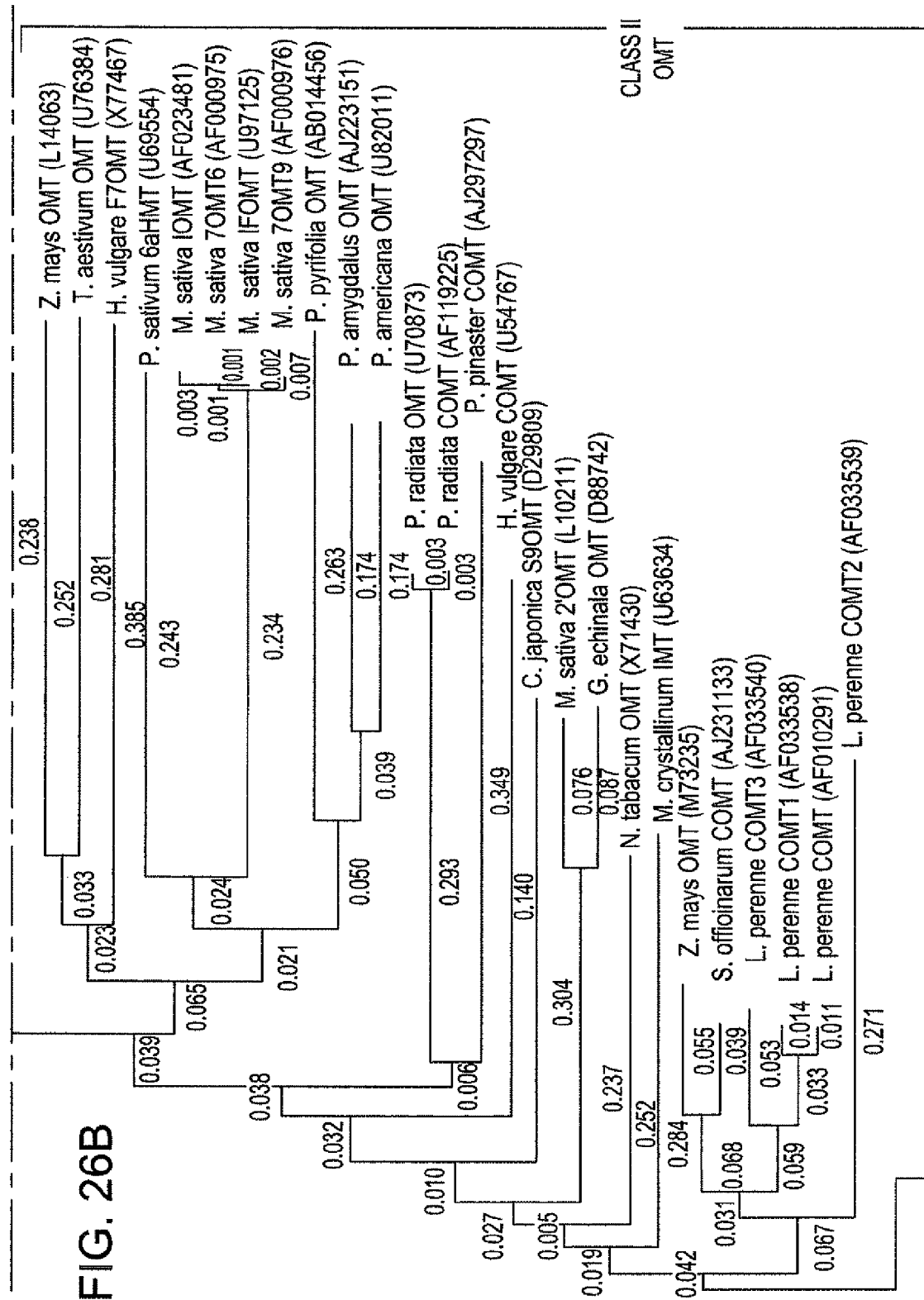
Figure 26C:
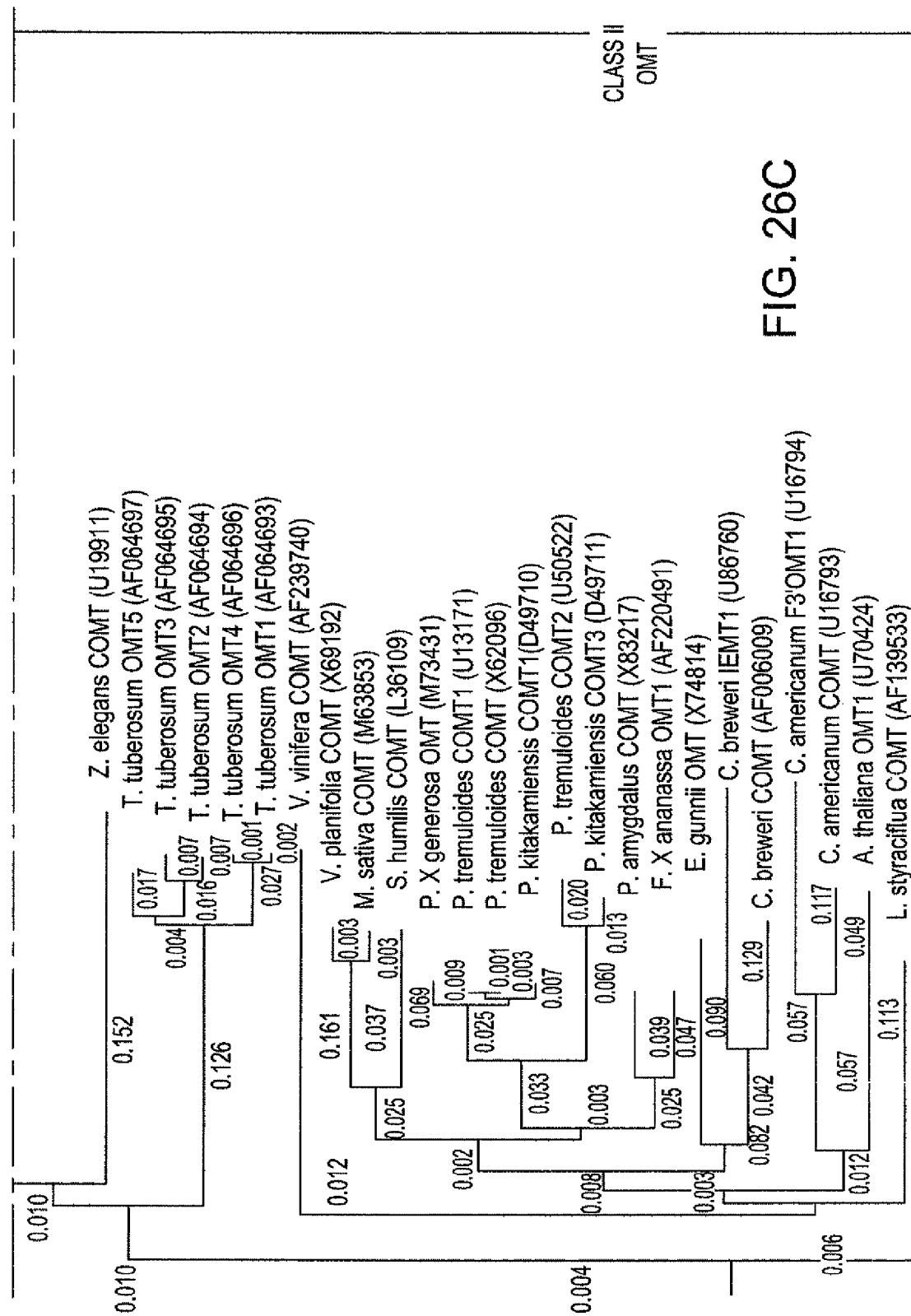
Figure 26D:
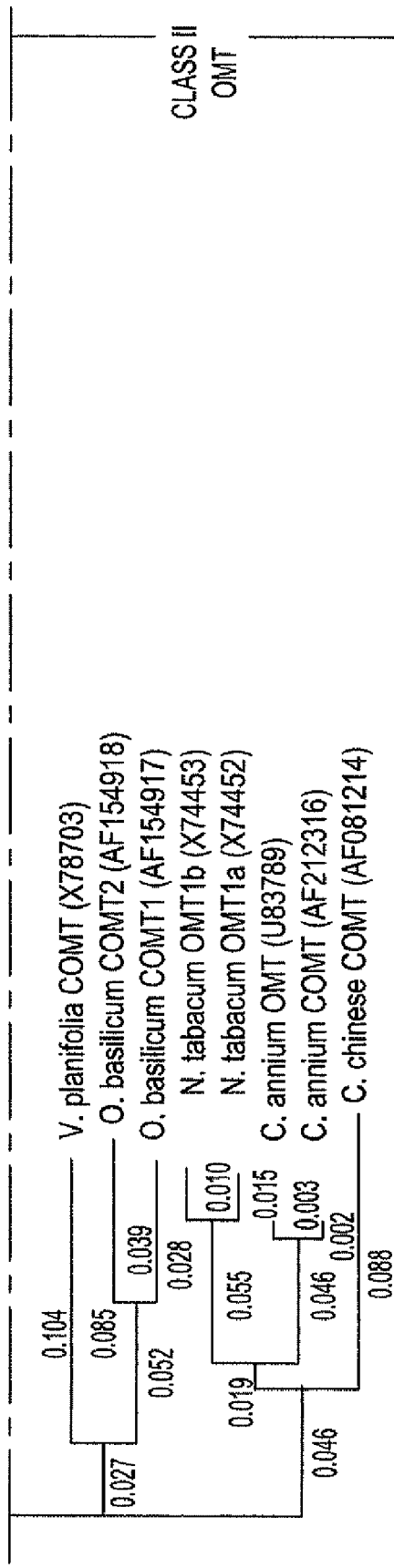

The 35S 5': FFMT: 35S 3' expression cassette from pCGP3290 (FIG. 23) was released upon digestion with the restriction endonuclease PstI. A 1.66 kb fragment containing the chimaeric *Fuchsia* FMT gene was subsequently isolated and ligated with PstI ends of the binary vector, pCGP2788 (FIG. 24). Correct ligation of the chimaeric gene in tandem with the 35S 5': SuRB gene and the chimaeric F3'5'H gene of pCGP2788 was established by restriction endonuclease analysis (HinDIII, XhoI, PstI, EcoRI, and NcoI) of plasmid DNA isolated from tetracycline-resistant transformants. The resulting plasmid was designated pCGP3292 (FIG. 25).

Plant Transformation with pCGP3292

The binary vector plasmid pCGP3292 was introduced into *A. tumefaciens* strain AGL0 and the T-DNA contained in pCGP3292 is introduced into *Rosa hybrida* via *Agrobacterium*-mediated transformation to produce petunidin and malvidin based pigments and lead to modifications flower colour (as detailed in Example 11)

Example 13

Dendogram of Plant Methyltransferases

A dendogram was constructed using the software package ClustalW (Thompson et al., 1994, supra) (FIG. 26). Deduced amino acid sequences of *Petunia* (pCGP1907.aa), *Torenia* (pTMT5.aa) and *Fuchsia* (pCGP3267.aa) FMTs were aligned with other full length plant O-methyltransferases of both Class I and Class II found in the GenBank database. The dendogram (FIG. 26) shows the clustering relationship between these sequences. All Class I SAM-OMT sequences are grouped together due to their overall level of sequence similarity. The *Petunia, Torenia* and *Fuchsia* FMT sequences are grouped with Class I SAM-OMTs. However, they are set apart from the main cluster. This indicates that these sequences are related to each other but share a lower level of sequence identity and similarity with other SAM-OMTs within this class. All other Class I SAM-OMTs have been identified as CCoAOMTs either by testing for corresponding enzyme activity with CoA-activated phenylpropanoid substrates derived from caffeic acid, or by sequence similarity with database entries. The sequences of an *A. thaliana* CCoAOMT (GenBank L40031) and a *Populus kitakamiensis* CCoAOMT (GenBank AB000408) are found in an adjacent cluster to that of the FMTs described here. These sequences are more similar to the FMTs than other CCoAOMTs. However, no experimental evidence exists for these clones regarding enzyme activity or substrates that are methylated. The remaining branches of the dendogram are formed by groupings of Class II SAM-OMTs. These include COMTs (caffeic acid OMTs), F3'OMT (flavonoid 3'-OMT; Gauthier et al., 1996, supra), IOMTs (isoflavone OMTs; He and Dixon, 1998, supra), 2'OMTs (isoliquiritigenin 2'-OMT; Maxwell et al., 1993, supra), IMT (inositol OMT; Rammesmeyer et al., 1995, supra), and F7OMT (flavonoid 7-OMT; Christensen et al., 1998, supra), among others. Given the variety of substrates utilized by the members of Class II SAM-OMTs, and the ability of some of these proteins to act on flavonoid compounds which are structurally related to the anthocyanins, it was unexpected that the FMTs isolated from *Petunia, Torenia* and *Fuchsia* do not fall into this category of SAM-OMTs. Reviews in the literature (Ibrahim and Muzac, 2000, supra; Schroder et al., *Phytochemistry*, 59: 1-8, 2002) have suggested that methyltransferases acting on flavonoids and specifically on anthocyanins would fall into the Class II SAM-OMTs. Surprisingly the FMT sequences disclosed in this specification resemble the CCoAOMTs in Class I more closely than members of the Class II SAM-OMTs. CCoAOMTs are known to efficiently utilize only a pair of CoA-activated substrates, caffeoyl-CoA (CCoA) and 5-hydroxyferuloyl-CoA (HFCoA). These phenylpropanoid compounds are directly derived from caffeic acid (CA) and 5-hydroxyferulic acid (HFA) which are efficiently utilized by COMT proteins of Class II SAM-OMTs. The basic ring structure of these flavonoids and anthocyanins is similar, the main difference with the anthocyanins being the presence of sugar and acyl side groups which form bulky additions to the molecule. It is thought that these groups may impose different steric requirements upon enzymes involved in modification of anthocyanins compared with, for example, flavanone and isoflavonoid molecules. Thus, in regard to anthocyanin compounds, the sugar and acyl side groups may mimic the large CoA group attached to these molecules imposing a similar steric requirement on SAM-OMT proteins that act on them.

Example 14

Isolation of FMT cDNAs from Other Species

Methylated anthocyanins such as but not limited to peonidin, petunidin and malvidin are produced in *Petunia* sp., *Plumbago* sp., *Vitis* sp., *Babiana stricta, Pinus* sp., *Picea* sp., *Larix* sp., *Phaseolus* sp., *Solanum* sp., *Vaccinium* sp., *Cyclamen* sp., *Iris* sp., *Pelargonium* sp., *Geranium* sp., *Pisum* sp., *Lathyrus* sp., *Clitoria* sp., *Catharanthus* sp., *Malvia* sp., *Mucuna* sp., *Vicia* sp., *Saintpaulia* sp., *Lagerstroemia* sp., *Tibouchina* sp., *Hypocalyptus* sp., *Rhododendron* sp., *Linum* sp., *Macroptilium* sp., *Hibiscus* sp., *Hydrangea* sp., *Ipomoea* sp., *Cymbidium* sp., *Millettia* sp., *Hedysarum* sp., *Lespedeza* sp., *Antigonon* sp., *Pisum* sp., etc.

It is expected that a number of these plants contain flavonoid methyltransferases (FMT).

Rare methylated anthocyanins (such as 5-methyl delphinidin, 5-methyl petunidin and 5-methyl malvidin) have been isolated from flowers of plants in the Plumbaginaceae family Harborne, 1967, supra). *Plumbago* flowers have been reported to contain a rare anthocyanin that is methylated at the 5-O position of malvidin. This molecule was described as capensinin (5-O-methyl malvidin) (Harborne, 1962, 1967, supra). The flavonol copigment present was described as azalein (quercetin 5-methyl ether 3-O-rhamnoside) (Harborne, 1962, 1967, supra). Further analysis of the common garden *Plumbago capsensis* (also known as *Plumbago auriculata*) has revealed that the methylated anthocyanin was 5,7-di-O-methyl malvidin (S. Bloor, unpublished results). It is expected that flowers from plants in the Plumbaginaceae family such as *Plumbago* are a suitable source for FMT sequences that encode FMTs that would methylate anthocyanins at positions 3',5', 3' and 5' as well as the 5-O and 7-O positions.

The isolation of FMT cDNAs from the plants listed above and others is accomplished by the screening of respective cDNA libraries with SEQ ID NO:1 and/or 4 and/or 6 and/or 11 and/or 21 and/or 26 and/or 41, and/or 43 using low stringency hybridisation conditions such as those described Example 9 or in the introduction of the instant specification.

Alternatively, the isolation of FMT cDNA fragments are accomplished using the polymerase chain reaction using CODEHOP primers as listed in Table 24 (Example 11) or degenerate primers as listed in Table 27, below. An example of the primer pair combinations that can be used is shown in Table 28, below. The amplification products are cloned into bacterial plasmid vectors and DNA fragments used as probes to screen respective cDNA libraries to isolate longer and full-length FMT cDNA clones. The functionality and specificity of the cDNA clones are ascertained using methods described in Examples 7, 8, 9, 10 and 11.

TABLE 27

More degenerate primers designed to areas of amino acid sequence similarity between methyltransferases that act on anthocyanins

| SEQ ID NO: | PRIMER SEQUENCE (5' TO 3') |
|---|---|
| 23 | OMTIf1 CCG GGA GCA CGA GCA CYT NAA RGA RYT |
| 24 | OMTIf3 GGC CTG CCC TTC ATC CAR AAR GCN GGN G |
| 25 | OMTIf4 CGT GGT AGT TCA CGT AGT TGC TCT TRT CNG CRT C | where R = A or G, Y = C or T, M = A or C, K = G or T, S = G or C, W = A or T, H = A or C or T, B = G or C or T, V = A or G or C, D = A or G or T, N = A or G or C or T, I = deoxyinosine.

TABLE 28

Primer pairs that are used in the isolation of other FMT cDNA fragments from different plants

| Forward primer | SEQ ID NO: | Reverse primer | SEQ ID NO: | Expected fragment (bp) |
|---|---|---|---|---|
| OMTIf1 | 21 | OMTIr3 | 17 | 285 |
| OMTIf1 | 21 | OMTIr4 | 23 | 399 |
| OMTIf1 | 21 | OMTIr5 | 18 | 609 |

TABLE 28-continued

Primer pairs that are used in the isolation of other FMT cDNA fragments from different plants

| Forward primer | SEQ ID NO: | Reverse primer | SEQ ID NO: | Expected fragment (bp) |
|---|---|---|---|---|
| OMTIf1 | 21 | Ad1 | 27 | 620 + 3'UTR |
| OMTIf2 | 15 | OMTIr3 | 17 | 159 |
| OMTIf2 | 15 | OMTIr4 | 23 | 273 |
| OMTIf2 | 15 | OMTIr5 | 18 | 483 |
| OMTIf2 | 15 | Ad1 | 27 | 492 + 3'UTR |
| OMTIf3 | 22 | OMTIr4 | 23 | 162 |
| OMTIf3 | 22 | OMTIr5 | 18 | 372 |
| OMTIf3 | 22 | Ad1 | 27 | 381 + 3'UTR |
| OMTIf4 | 16 | OMTIr5 | 18 | 258 |
| OMTIf4 | 16 | Ad1 | 27 | 267 + 3'UTR |
| OMTIr3 | 17 | GI-anchor | 20 | 375 + 5'UTR |
| OMTIr4 | 23 | GI-anchor | 20 | 489 + 5'UTR |
| OMTIr5 | 18 | GI-anchor | 20 | 699 + 5'UTR |

+ 3'UTR = plus the 3' untranslated sequence,
+ 5'UTR = plus the 5' untranslated sequence Estimations of the expected size of fragment are based on the *Petunia* FMT (E20) sequence [SEQ ID NO:4]. The sizes obtained using cDNA as template from different species would be expected to vary.

Example 15

Use of FMTs

In order to produce methylated dephinidin pigments in plants that do not normally produce delphinidin-based pigments and does not contain a flavonoid methyltransferase capable of methylating anthocyanidins, specifically delphinidin, constructs containing the combination of a F3'5'H gene (such as but not limited to the chimaeric *Viola* F3'5'H gene) and a FMT gene (such as but not limited to those isolated from *Petunia, Fuchsia, Torenia, Plumbago*) are introduced into a species that does not normally produce delphinidin-based pigments. Such plants may include but are not limited to carnation, chrysanthemum, gerbera, orchids, *Euphorbia, Begonia* and apple.

In order to produce methylated pigments in species or cultivars of species that produce delphinidin or cyanidin but do not have a flavonoid methyltransferase capable of methylating these anthocyanins, FMT genes are introduced into plant species or specific cultivars of species that do not produce methylated anthocyanin pigments. Such plants include but are not limited to pansy, *Nierembergia*, lisianthus, cultivars of grapevine and lily.

In order to reduce or block the production of indigenous methylated pigments a variety of strategies can be employed including but not limited to PTGS, RNAi, antisense, co-suppression technologies. Strategies include the introduction of FMT sequences into plant species or cultivars of species that produce methylated anthocyanin pigments such as petunidin, malvidin, peonidin, capsenidin or other methylated anthocyanin. Such species include those described in Example 14, such as *Impatiens, Catharanthus, cyclamen, Torenia, Petunia, Fuchsia, Plumbago, Pelargonium* and certain cultivars of grapevine.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Altschul et al., *Nucl. Acids Res.* 25: 3389, 1997
Altschul et al., *J. Mol. Biol.* 215: 403-410, 1990
Andersen et al., *Phytochemistry*, 38: 1513-1517, 1995
Andersen, *Biochemical systematics and ecology*, 20: 145-148, 1992
Ando et al., *Biochemical systematics and ecology*, 27: 623-650, 1999
Australian Provisional Patent Applications No. 2002951088 and 2002952835 entitled "Genetic Sequences and uses therefor", 2002
Ausubel et al., *Current Protocols in Molecular Biology*, John Wiley & Sons Inc, 1994-1998, Chapter 15, 1998
Aviv and Leder, *Proc. Natl. Acad. Sci. USA* 69: 1408, 1972
Ballington et al., *Can. J. of Plant Sci.*, 68: 241-246, 1988
Bonner and Laskey, *Eur. J. Biochem.* 46: 83, 1974
Brouillard and Dangles, In: *The Flavonoids—Advances in Research since* 1986. Harborne, J. B. (ed), Chapman and Hall, London, UK, 1-22, 1993
Brugliera et al., *Plant J.* 5, 81-92, 1994
Bullock et al., *Biotechniques* 5: 376, 1987
Cachio et al., *American J of Ecology and Viticulture*, 43: 244-248, 1992
Carew and Krueger, *Phytochemistry*, 15: 442, 1976
Catalano et al., *J. Agricultural and Food Chemistry*, 49: 4568-4570, 1998
Chriki and Harborne, *Phytochemistry*, 22: 2322-2323, 1983
Chriki, *Agronomie*, 10: 553-540, 1990
Christensen et al., *Plant Mol. Biol.* 36: 219-227, 1998
Comai et al., *Plant Mol. Biol.* 15: 373-381, 1990
Comai et al., *Plant Molecular Biology* 15: 373-381, 1990
Crowden, *Phytochemistry*, 21: 2989-2990, 1982
Depicker, A. et al., *J Mol. and Appl. Genetics*, 1: 561-573, 1982
Francis et al., *J Am Soc Hortic Sci*, 107: 789-791, 1982
Franck et al., *Cell* 21: 285-294, 1980
Fukui et al., *Phytochemistry*, 47: 1409-1416, 1998
Gamborg et al., *Exp. Cell Res.* 50: 151-158, 1968
Gauthier et al., *Plant Mol. Biol.* 32: 1163-1169, 1996
Goto, *Tetrahedron* 27: 2413-2416, 1987
Griesbach et al., *Phytochemistry* 30: 1729-1731, 1991
Griesbach, *Phytochemistry*, 48: 829-830, 1998
Guilley et al., *Cell*, 30: 763-773. 1982
Hanahan, *J. Mol. Biol.* 166: 557, 1983 and. *Bethesda Res. Lab. Focus.* 8(2): 9, 1986
Haslam, *Practical Phenolics. From structure to molecular recognition and physiological action*. Cambridge University Press, UK, 1998
He and Dixon, *Plant Mol. Biol.* 36: 43-54, 1998
Holton and Cornish, *Plant Cell* 7: 1071-1083, 1995;
Holton et al., *Nature*, 366: 276-279, 1993
Hopp and Seitz, *Planta* 170: 74-85, 1987
Hungria et al., *Plant Physiology*, 97: 751-758, 1991
Ibrahim and Muzac, In *Recent advances of phytochemistry*. Evolution of metabolic pathways. Elsevier Science Ltd. 34: 349-385, 2000
Imrie and Hutton, *J. Hered.*, 69: 54-56 1978
Inoue et al., *Gene* 96: 23-28, 1990
Inoue et al., 1990
Ishikura and Shibata, *Bot Mag (Tokyo)*, 86: 1-4, 1973
Jefferson et al., *EMBO J.* 6(13): 3901-3907, 1987
Jefferson, et al., *EMBO J.* 6: 3901-3907, 1987

Jonsson et al., *Phytochemistry* 21(10): 2457-2460, 1982
Jonsson et al., *Planta* 160: 174-179, 1984a
Jonsson et al., *Theor. Appl. Genet.* 66: 349-355, 1983
Jonsson et al., *Theor. Appl. Genet.* 68: 459-466, 1984b
Joshi and Chiang, *Plant Mol. Biol.* 37: 663-674, 1998
Kim and Fujieda, *J. Kor. Soc. Hortic. Sci.*, 32: 247-255, 1991
Kim et al., *Phytochemistry*, 28: 1503-1506, 1989
Klee et al., *Bio/Technology* 3: 637-642, 1985
Kobayashi et al., *Breeding Science*, 48: 169-176, 1998
Kroon et al., *Plant J* 5: 69-80, 1994
Lazo et al., *Bio/technology* 9: 963-967, 1991
Lee et al., *EMBO J.* 7: 1241-1248, 1988
Lewis et al., *J. of the Science of Food and Agriculture*, 77: 45-57, 1998 Marchant et al., *Molecular Breeding* 4: 187-194, 1998
Markham, *Techniques of flavonoid identification.*, Academic Press, London, 1982
Marmur and Doty, *J. Mol. Biol.* 5:109, 1962
Maxwell, *Plant J.* 4(6): 971-981, 1993
Merrifield, *J. Am. Chem. Soc.* 85: 2149, 1964
Mikanagi et al., *Biochem. System and Ecol.* 23: 183-200, 1995
Mikanagi et al., *Biochem. System and Ecol.* 28: 887-902, 2000
Mitchell et al., *Phytochemistry*, 47: 355-361, 1998
Mitsuhashi et al., *Plant Cell Physiol.* 37: 49-59, 1996
Mol et al., *Trends Plant Sci.* 3: 212-217, 1998
Murashige and Skoog, *Physiol. Plant* 15: 73-97, 1962
Nozzolillo et al., *Canadian Journal of Botany*, 67: 1600-1604, 1989
Parvez and Ogbeide, *Phytochemistry*, 29: 2043-2044, 1990
Pearson and Lipman, *Proc. Natl. Acad. Sci. USA* 85: 2444-2448, 1988
Rammesmeyer et al., *Arch. Biochem. Biophys.* 322(1): 183-188, 1995
Rat'kin et al., *Zh Obshch Biol*, 41: 685-699, 1980
Robinson and Firoozabady, *Scientia Horticulturae*, 55: 83-99, 1993
Rose et al., *Nucl Acids Res*, 26: 1628-1635, 1998
Rout et al., *Scientia Horticulturae*, 81: 201-238, 1999
Sambrook et al., *Molecular Cloning: A Laboratory Manual.* (2nd edition), Cold Spring Harbor Laboratory Press, USA, 1989
Schenk and Hildebrandt, *Can. J. Bot.* 50: 199-204, 1972
Schroder et al., *Phytochemistry*, 59: 1-8, 2002
Seitz and Hinderer, Anthocyanins. In: *Cell Culture and Somatic Cell Genetics of Plants*. Constabel, F. and Vasil, I. K. (eds.), Academic Press, New York, USA, 5: 49-76, 1988
Sink (ed), *Petunia*, Springer-Verlag, Berlin, 1984
Skrede et al., *J of Food Science*, 65: 357-364, 2000
Srivastava and Pande, *Planta Med*, 32: 138-140, 1977
Stafford, *Flavonoid Metabolism*. CRC Press, Inc. Boca Raton, Fla., USA, 1990
Strack and Wray, In: *The Flavonoids—Advances in Research since 1986*. Harborne, J. B. (ed), Chapman and Hall, London, UK, 1-22, 1993
Takeda et al., *Phytochemistry*, 28: 499-500, 1989
Takeda et al., *Phytochemistry*, 29: 1089-1091, 1990
Takeoka et al., *Journal of Agricultural and Food Chemistry*, 45: 3395-3400, 1997
Tanaka et al., *Plant Cell Physiol* 37: 711-716, 1996
Terahara et al., *J. Natural Products*, 56: 335-340, 1993
Thompson et al., *Nucl. Acids Res.* 2: 4673-4680, 1994
Tiwari and Minocha, *Vijnana Parishad Anusandhan Patrika*, 23: 305-308, 1980
Toki and Katsuyama, *J. Jap Soc Hortic. Sci.*, 63: 853-861, 1995
Toki et al., *Phytochemistry*, 37: 885-887, 1994
Turpen and Griffith, *BioTechniques* 4: 11-15, 1986
Van Wyk et al., *Biochemical systematics and ecology*, 23: 295-297, 1995
VanEngelen et al., *Transgenic Res.* 4: 288-290, 1995
Webby and Boase, *Phytochemistry*, 52: 939-941, 1999
Winkel-Shirley, *Plant Physiol.* 126: 485-493, 2001a
Winkel-Shirley, *Plant Physiol.* 127: 1399-1404, 2001b
Woltering and Somhorst, *J. Plant Physiol.*, 136: 295-299, 1990
Yabuya and Noda, *Euphytica*, 103: 325-328, 1998
Yabuya et al., *Euphytica*, 98: 163-167, 1997

---

The invention claimed is:

1. An isolated nucleic acid molecule comprising a sequence of nucleotides encoding or complementary to a sequence encoding a flavonoid methyltransferase (FMT) which FMT methylates anthocyanins, said sequence of nucleotides comprising a nucleotide sequence selected from the group consisting of:
   (i) the nucleotide sequence set forth in SEQ ID NO:11;
   (ii) a nucleotide sequence having at least 95% identity after optimal alignment to SEQ ID NO:11;
   (iii) a nucleotide sequence encoding the amino acid sequence set forth in SEQ ID NO:12; and
   (iv) a nucleotide sequence encoding an amino acid sequence having at least 95% identity after optimal alignment to SEQ ID NO: 12.

2. The isolated nucleic acid molecule of claim 1, wherein said sequence of nucleotides comprises a nucleotide sequence having at least 95% identity after optimal alignment to SEQ ID NO:11.

3. The isolated nucleic acid molecule of claim 1, wherein said sequence of nucleotides comprises a nucleotide sequence encoding an amino acid sequence having at least 95% identity after optimal alignment to SEQ ID NO:12.

4. The isolated nucleic acid molecule of claim 1 wherein the FMT is a Class I S-adenosyl-L-methionine O-methyltransferase (SAM-OMTs).

5. The isolated nucleic acid molecule of claim 1 wherein the FMT is 3'FMT or 3'5'FMT.

6. The isolated nucleic acid molecule of claim 1 wherein said anthocyanin is a derivate of delphinidin.

7. The isolated nucleic acid molecule of claim 1 wherein said anthocyanin is a derivative of petunidin or cyanidin.

8. The isolated nucleic acid molecule of claim 1 wherein said anthocyanin is delphinidin 3-glucoside, delphinidin 3,5-diglucoside or delphinidin 3-rutinoside.

9. A genetic construct comprising a nucleic acid molecule encoding or complementary to a sequence encoding a flavonoid methyltransferase (FMT) which methylates anthocyanins, the genetic construct comprising a nucleotide sequence selected from the group consisting of:
   (i) the nucleotide sequence set forth in SEQ ID NO:11;
   (ii) a nucleotide sequence having at least 95% identity after optimal alignment to SEQ ID NO:11;
   (iii) a nucleotide sequence encoding the amino acid sequence set forth in SEQ ID NO:12; and
   (iv) a nucleotide sequence encoding an amino acid sequence having at least 95% identity after optimal alignment to SEQ ID NO:12.

10. The genetic construct of claim 9, wherein said sequence of nucleotides comprises a nucleotide sequence having at least 95% identity after optimal alignment-to SEQ ID NO:11.

11. The genetic construct of claim 9, wherein said sequence of nucleotides comprises a nucleotide sequence encoding an amino acid sequence having at least 95% identity after optimal alignment to SEQ ID NO:12.

12. A genetically modified plant or part thereof or cells therefrom comprising an isolated genetic material encoding or complementary to a sequence encoding a flavonoid methyltransferase (FMT) which methylates anthocyanins, the isolated genetic material comprising a nucleotide sequence selected from the group consisting of:
   (i) the nucleotide sequence set forth in SEQ ID NO:11;
   (ii) a nucleotide sequence having at least 95% identity after optimal alignment to SEQ ID NO:11;
   (iii) a nucleotide sequence encoding the amino acid sequence set forth in SEQ ID NO:12; and
   (iv) a nucleotide sequence encoding an amino acid sequence having at least 95% identity after optimal alignment to SEQ ID NO:12.

13. The genetically modified plant or part thereof or cells of claim 12, wherein said sequence of nucleotides comprises a nucleotide sequence having at least 95% identity after optimal alignment to SEQ ID NO:11.

14. The genetically modified plant or part thereof or cells of claim 12, wherein said sequence of nucleotides comprises a nucleotide sequence encoding an amino acid sequence having at least 95% identity after optimal alignment to SEQ ID NO:12.

15. The genetically modified plant or part thereof or cells therefrom of claim 12 wherein said plant or part thereof or cells therefrom is from a cut-flower species.

16. The genetically modified plant or part thereof or cells therefrom of claim 12 wherein said plant or part thereof or cells therefrom is a horticultural plant species.

17. The genetically modified plant or part thereof or cells therefrom of claim 12 wherein said plant or part thereof or cells therefrom is an agricultural plant species.

18. The genetically modified plant or part thereof or cells thereof of any one of claims 15-17 wherein the plant exhibits altered flowers or inflorescence.

19. The genetically modified plant or part thereof or cells therefrom of any one of claims 15-17 wherein said altered part is a sepal, bract, petiole, peduncle, ovary or anther stem.

20. The genetically modified plant or part thereof or cells therefrom of any one of claims 15-17 wherein said altered part is a leaf, root, flower, seed, fruit, nut, berry or vegetable.

21. Flowers cut or severed from the plant of claim 15 or 16.

22. Progeny, offspring of progeny or vegetative propagated lines of the genetically modified plant of claim 15 wherein the progeny or offspring of said progeny comprise the isolated genetic material.

* * * * *

SEQUENCE LISTING

```
<160> NUMBER OF SEQ ID NOS: 51

<210> SEQ ID NO 1
<211> LENGTH: 969
<212> TYPE: DNA
<213> ORGANISM: Petunia

<400> SEQUENCE: 1
ctcaatttga atattactac caaggatttt actgaagcaa tgacaggcaa aaccgcccac      60
cctggcattc ttcgaagtga tgccctcagg aagtacattt tggaaacctc agtttatcca     120
agagagcatg agctactcaa agaactaaca aaagcttcat tcgagaatta taaagcagcg     180
agctttatgg gtcttcctca agatgaagcc cagtttctat cgatgttcct aaagctcata     240
aatgcaaaga aaacactaga gattggagtt ttcactggtt actctctgct tgttactgct     300
cttgctttgc cagaagatgg gaaagtaata gcaattgacc cggacagaga ggcatatgag     360
gttggattac cttatattca gaaggctggt gtggaacata agatcgagtt cattcaatca     420
gaagccgtgc ccgttcttga aaaactcctc tctaacgaga aagaagcagg gacatttgat     480
```

```
ttcgtgttca ttgatgctga taaggagaat tatttgaagt accatgagat agtgctaaaa      540
ttggtgaaag ttggaggagt gataggatat gacaacacct tatggtttgg gacagtggca      600
ctttcagagg atgatccaat gccagaaggt ttaagagcat taaggggaca tgttatgaag      660
gtcaatagct ttttagctac tgaccctcgt gttgaagtag ctcaactttc aattggtgat      720
ggccttaccc tttgcaggcg tctctcctag gtccagttaa ttggtgcaat gccaagtcaa      780
cgcgaagata tgtactagat gtatgtcagg ggttgaattt attgaattta tgttgttgag      840
aagaacaaaa gttctatatt tgtgttgttt gcaagtattt gaaacttgta ggagcctttt      900
ggttgccttg aataagaaaa tcttttacag tcttttagct taaaaaaaaa aaaaaaaaa      960 aaaaaaaaa                                                              969
```

```
<210> SEQ ID NO 2
<211> LENGTH: 251
<212> TYPE: PRT
<213> ORGANISM: Petunia

<400> SEQUENCE: 2
```

Asn Ser Leu Asn Leu Asn Ile Thr Thr Lys Asp Phe Thr Glu Ala Met
1               5                   10                  15

Thr Gly Lys Thr Ala His Pro Gly Ile Leu Arg Ser Asp Ala Leu Arg
            20                  25                  30

Lys Tyr Ile Leu Glu Thr Ser Val Tyr Pro Arg Glu His Glu Leu Leu
        35                  40                  45

Lys Glu Leu Thr Lys Ala Ser Phe Glu Asn Tyr Lys Ala Ala Ser Phe
    50                  55                  60

Met Gly Leu Pro Gln Asp Glu Ala Gln Phe Leu Ser Met Phe Leu Lys
65                  70                  75                  80

Leu Ile Asn Ala Lys Lys Thr Leu Glu Ile Gly Val Phe Thr Gly Tyr
                85                  90                  95

Ser Leu Leu Val Thr Ala Leu Ala Leu Pro Glu Asp Gly Lys Val Ile
            100                 105                 110

Ala Ile Asp Pro Asp Arg Glu Ala Tyr Glu Val Gly Leu Pro Tyr Ile
        115                 120                 125

Gln Lys Ala Gly Val Glu His Lys Ile Glu Phe Ile Gln Ser Glu Ala
    130                 135                 140

Val Pro Val Leu Glu Lys Leu Leu Ser Asn Glu Lys Glu Ala Gly Thr
145                 150                 155                 160

Phe Asp Phe Val Phe Ile Asp Ala Asp Lys Glu Asn Tyr Leu Lys Tyr
                165                 170                 175

His Glu Ile Val Leu Lys Leu Val Lys Val Gly Gly Val Ile Gly Tyr
            180                 185                 190

Asp Asn Thr Leu Trp Phe Gly Thr Val Ala Leu Ser Glu Asp Asp Pro
        195                 200                 205

Met Pro Glu Gly Leu Arg Ala Leu Arg Gly His Val Met Lys Val Asn
    210                 215                 220

Ser Phe Leu Ala Thr Asp Pro Arg Val Glu Val Ala Gln Leu Ser Ile
225                 230                 235                 240

Gly Asp Gly Leu Thr Leu Cys Arg Arg Leu Ser
                245                 250

```
<210> SEQ ID NO 3
<211> LENGTH: 45
<212> TYPE: DNA
<213> ORGANISM: Artificial Sequence
```

```
<220> FEATURE:
<223> OTHER INFORMATION: oligonucleotide

<400> SEQUENCE: 3
gagagagaga gagagagaga tctcgagttt tttttttttt ttttt                45

<210> SEQ ID NO 4
<211> LENGTH: 888
<212> TYPE: DNA
<213> ORGANISM: Petunia

<400> SEQUENCE: 4
cacttctcta ttttcttgaa aagcaccctc aatttgaata ttactaccaa ggatttract     60
gaagcaatga caggcaaaac cgcccaccct ggcattcttc gaagtgatgc cctcaggaag    120
tacattttgg aaacctcagt ttatccaaga gagcatgagc tactcaaaga actaacaaaa    180
gcttcattcg agaattataa agcagcgagc tttatgggtc ttcctcaaga tgaagcccag    240
tttctatcga tgttcctaaa gctcataaat gcaaagaaaa cactagagat tggagttttc    300
actggttact ctctgcttgt tactgctctt gctttgccag aagatgggaa agtaatagca    360
attgacccgg acagagaggc atatgaggtt ggattacctt atattcagaa ggctggtgtg    420
gaacataaga tcgagttcat tcaatcagaa gccgtgcccg ttcttgaaaa actcctctct    480
aacgagaaag aagcagggac atttgatttc gtgttcattg atgctgataa ggagaattat    540
ttgaagtacc atgagatagt gctaaaattg gtgaaagttg gaggagtgat aggatatgac    600
aacaccttat ggtttgggac agtggcactt tcagaggatg atccaatgcc agaaggttta    660
agagcattaa ggggacatgt tatgaaggtc aatagctttt tagctactga ccctcgtgtt    720
gaagtagctc aactttcaat tggtgatggc cttacccttt gcaggcgtct ctcctaggtc    780
cagttaattg gtgcaatgcc aagtcaacgc gaagatatgt actagatgta tgtcaggggt    840
tgaatttatt gaatttatgt tgttgagaag aaaaaaaaaa aaaaaaaa                888

<210> SEQ ID NO 5
<211> LENGTH: 263
<212> TYPE: PRT
<213> ORGANISM: Petunia

<400> SEQUENCE: 5

Ile Pro Leu Leu Ser His Phe Ser Ile Phe Leu Lys Ser Thr Leu Asn
1               5                   10                  15

Leu Asn Ile Thr Thr Lys Asp Phe Thr Glu Ala Met Thr Gly Lys Thr
            20                  25                  30

Ala His Pro Gly Ile Leu Arg Ser Asp Ala Leu Arg Lys Tyr Ile Leu
        35                  40                  45

Glu Thr Ser Val Tyr Pro Arg Glu His Glu Leu Leu Lys Glu Leu Thr
    50                  55                  60

Lys Ala Ser Phe Glu Asn Tyr Lys Ala Ala Ser Phe Met Gly Leu Pro
65                  70                  75                  80

Gln Asp Glu Ala Gln Phe Leu Ser Met Phe Leu Lys Leu Ile Asn Ala
                85                  90                  95

Lys Lys Thr Leu Glu Ile Gly Val Phe Thr Gly Tyr Ser Leu Leu Val
            100                 105                 110

Thr Ala Leu Ala Leu Pro Glu Asp Gly Lys Val Ile Ala Ile Asp Pro
        115                 120                 125

Asp Arg Glu Ala Tyr Glu Val Gly Leu Pro Tyr Ile Gln Lys Ala Gly
    130                 135                 140
```

```
Val Glu His Lys Ile Glu Phe Ile Gln Ser Glu Ala Val Pro Val Leu
145                 150                 155                 160

Glu Lys Leu Leu Ser Asn Glu Lys Glu Ala Gly Thr Phe Asp Phe Val
            165                 170                 175

Phe Ile Asp Ala Asp Lys Glu Asn Tyr Leu Lys Tyr His Glu Ile Val
        180                 185                 190

Leu Lys Leu Val Lys Val Gly Val Ile Gly Tyr Asp Asn Thr Leu
    195                 200                 205

Trp Phe Gly Thr Val Ala Leu Ser Glu Asp Asp Pro Met Pro Glu Gly
    210                 215                 220

Leu Arg Ala Leu Arg Gly His Val Met Lys Val Asn Ser Phe Leu Ala
225                 230                 235                 240

Thr Asp Pro Arg Val Glu Val Ala Gln Leu Ser Ile Gly Asp Gly Leu
                245                 250                 255

Thr Leu Cys Arg Arg Leu Ser
            260
```

<210> SEQ ID NO 6
<211> LENGTH: 1077
<212> TYPE: DNA
<213> ORGANISM: Petunia

<400> SEQUENCE: 6

```
attttctgga caagttcgat tacctttgaa tctccaagga ctttactgaa tcaatggcag      60
gcaaaagcgg acatggctcc attcttcaaa gtgaagccct caagaagtac atcttcgaaa    120
ctagtgtgta ccaagagaaa cacgagcaac tcaaagaact cacacaagcc tcattcgata    180
agtataaaat agtgagcttg atgggtgtgc ctccagatga agcccaattt ctctcgatgc    240
tcttaaaaat aatgaatgca aagaagacaa tggagattgg agttttttacc ggttattctc    300
ttctggctac tgctcttgca ttgccagaag atggaaaaat tatagcgatt gatccggaca    360
gagaagcata tgaggttgga ttgccatata ttcagaaggc tggtgtggag cataagattg    420
aatttattca atcagaagcc ttaccagtac tcgaaaaact cctctaacgg tgaggaagaa    480
ggaacatttg atttcatatt cattgatgct gataaggaga actatctgaa gtaccatgag    540
atagtactaa aattggtgaa agtgggagga gtgataggca tgacaacac attatggttt    600
gggaccgtgg cactttcaga tgatgatcct ataccacaag gcttaagaga attgaggaga    660
tcggttttga agatcaacag tttttagct actgatcctc gcattgaatt agctcatctt    720
tcaattggtg atggtcttac ccttggcagg cgtctcagct agtttatttt tcgtataatc    780
atctgaattc cggaatccat tatctttata gttttttgtt tttcagtact agtgatattt    840
ttcagtcccc acttatggat aacactgggt aatgagtatt gttgcagaag tagtgacatt    900
tttaagtttg ttcgtccat ctgctaaaga agtcacgatt cgtcttgta gacgagctat    960
agtatgcatt tgcattttgg ttaatttcgc atgtagtgtt gaaatgtgaa ttaccaaaag   1020
caaaagtaat aaaatgttta catttgttgt gttttaaaaa aaaaaaaaa aaaaaaa       1077
```

<210> SEQ ID NO 7
<211> LENGTH: 244
<212> TYPE: PRT
<213> ORGANISM: Petunia

<400> SEQUENCE: 7

```
Ile Ser Lys Asp Phe Thr Glu Ser Met Ala Gly Lys Ser Gly His Gly
1               5                   10                  15
```

```
Ser Ile Leu Gln Ser Glu Ala Leu Lys Lys Tyr Ile Phe Glu Thr Ser
            20                  25                  30

Val Tyr Pro Arg Glu His Glu Gln Leu Lys Glu Leu Thr Gln Ala Ser
        35                  40                  45

Phe Asp Lys Tyr Lys Ile Val Ser Leu Met Gly Val Pro Pro Asp Glu
    50                  55                  60

Ala Gln Phe Leu Ser Met Leu Leu Lys Ile Met Asn Ala Lys Lys Thr
65                  70                  75                  80

Met Glu Ile Gly Val Phe Thr Gly Tyr Ser Leu Leu Ala Thr Ala Leu
                85                  90                  95

Ala Leu Pro Glu Asp Gly Lys Ile Ile Ala Ile Asp Pro Asp Arg Glu
            100                 105                 110

Ala Tyr Glu Val Gly Leu Pro Tyr Ile Gln Lys Ala Gly Val Glu His
        115                 120                 125

Lys Ile Glu Phe Ile Gln Ser Glu Ala Leu Pro Val Leu Glu Lys Leu
    130                 135                 140

Leu Ser Asn Gly Glu Glu Gly Thr Phe Asp Phe Ile Phe Ile Asp
145                 150                 155                 160

Ala Asp Lys Glu Asn Tyr Leu Lys Tyr His Glu Ile Val Leu Lys Leu
                165                 170                 175

Val Lys Val Gly Gly Val Ile Gly Tyr Asp Asn Thr Leu Trp Phe Gly
            180                 185                 190

Thr Val Ala Leu Ser Asp Asp Pro Ile Pro Gln Gly Leu Arg Glu
        195                 200                 205

Leu Arg Arg Ser Val Leu Lys Ile Asn Ser Phe Leu Ala Thr Asp Pro
    210                 215                 220

Arg Ile Glu Leu Ala His Leu Ser Ile Gly Asp Gly Leu Thr Leu Gly
225                 230                 235                 240

Arg Arg Leu Ser

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
cttgctttgc cagaagatgg                                            20

<210> SEQ ID NO 9
<211> LENGTH: 32
<212> TYPE: DNA
<213> ORGANISM: Artificial Sequence
<220> FEATURE:
<223> OTHER INFORMATION: oligonucleotide

<400> SEQUENCE: 9
gcatggatcc acaggcaaaa ccgcccaccc tg                              32

<210> SEQ ID NO 10
<211> LENGTH: 31
<212> TYPE: DNA
<213> ORGANISM: Artificial Sequence
<220> FEATURE:
<223> OTHER INFORMATION: oligonucleotide

<400> SEQUENCE: 10
```

-continued

```
gcatctgcag ctaggagaga cgcctgcaaa g                                    31
```

<210> SEQ ID NO 11
<211> LENGTH: 1006
<212> TYPE: DNA
<213> ORGANISM: Torenia

<400> SEQUENCE: 11

```
ttcaattccg ccattttctc caataataac attcataaat acaatcagca gcagcaaaaa     60
tgaaagataa gttctatggc accattttgc agagcgaagc cctcgcaaag tatctgttag    120
agacaagtgc ctatccacga gaacatccgc agctcaaaga actaaggagc gcaactgtgg    180
acaagtatca atattggagc ttgatgaatg ttccagctga tgagggcag ttcatttcaa     240
tgttactgaa aattatgaac gcaaaaaga caattgaagt tggagttttc acaggctact    300
cactcctatc aactgctctg ctctacctg atgatggcaa aatcgttgcc attgatcctg    360
atagagaagc ttatgagact ggtttgccat ttatcaagaa agcaaacgtg gctcataaaa    420
tccaatacat acaatctgat gccatgaaag tcatgaatga cctcattgct gccaagggag    480
aagaagaaga ggggagcttt gactttgggt tcgtggatgc agacaaagaa aactacataa    540
actaccacga gaaactgttg aagctggtta aggttggagg gatcatagga tacgacaaca    600
ctctgtggtc tggaacagtt gctgcatctg aagacgatga gaataatatg cgagactact    660
taagaggttg cagagggcat atcctcaaac taaactcctt tctcgcaaac gatgatcgga    720
ttgaattggc tcacctctct attggagatg gactcacctt gtgcaaacgt ctcaaataat    780
aattttcaac tttattatta ttgtttcata aaagcatttt actgctggcc tggcctggcc    840
tgtttcagca tcttatattt ctattgttct aaatattta gttatcttgt ttatcaactt    900
gtctgtctta tatgtttaaa agaaagatgt catgtaattg taactcgatc gggctcttgt    960
aatattataa tgaattttat tgattttcaa aaaaaaaaa aaaaaa                   1006
```

<210> SEQ ID NO 12
<211> LENGTH: 239
<212> TYPE: PRT
<213> ORGANISM: Torenia

<400> SEQUENCE: 12

```
Met Lys Asp Lys Phe Tyr Gly Thr Ile Leu Gln Ser Glu Ala Leu Ala
1               5                   10                  15

Lys Tyr Leu Leu Glu Thr Ser Ala Tyr Pro Arg Glu His Pro Gln Leu
            20                  25                  30

Lys Glu Leu Arg Ser Ala Thr Val Asp Lys Tyr Gln Tyr Trp Ser Leu
        35                  40                  45

Met Asn Val Pro Ala Asp Glu Gly Gln Phe Ile Ser Met Leu Leu Lys
    50                  55                  60

Ile Met Asn Ala Lys Lys Thr Ile Glu Val Gly Val Phe Thr Gly Tyr
65                  70                  75                  80

Ser Leu Leu Ser Thr Ala Leu Ala Leu Pro Asp Asp Gly Lys Ile Val
                85                  90                  95

Ala Ile Asp Pro Asp Arg Glu Ala Tyr Glu Thr Gly Leu Pro Phe Ile
            100                 105                 110

Lys Lys Ala Asn Val Ala His Lys Ile Gln Tyr Ile Gln Ser Asp Ala
        115                 120                 125

Met Lys Val Met Asn Asp Leu Ile Ala Ala Lys Gly Glu Glu Glu Glu
    130                 135                 140
```

```
Gly Ser Phe Asp Phe Gly Phe Val Asp Ala Asp Lys Glu Asn Tyr Ile
145                 150                 155                 160

Asn Tyr His Glu Lys Leu Leu Lys Leu Val Lys Val Gly Gly Ile Ile
            165                 170                 175

Gly Tyr Asp Asn Thr Leu Trp Ser Gly Thr Val Ala Ala Ser Glu Asp
        180                 185                 190

Asp Glu Asn Asn Met Arg Asp Tyr Leu Arg Gly Cys Arg Gly His Ile
    195                 200                 205

Leu Lys Leu Asn Ser Phe Leu Ala Asn Asp Asp Arg Ile Glu Leu Ala
    210                 215                 220

His Leu Ser Ile Gly Asp Gly Leu Thr Leu Cys Lys Arg Leu Lys
225                 230                 235

<210> SEQ ID NO 13
<211> LENGTH: 37
<212> TYPE: DNA
<213> ORGANISM: Artificial Sequence
<220> FEATURE:
<223> OTHER INFORMATION: oligonucleotide

<400> SEQUENCE: 13
gcatggatcc aaagataagt tctatggcac cattttg                             37

<210> SEQ ID NO 14
<211> LENGTH: 35
<212> TYPE: DNA
<213> ORGANISM: Artificial Sequence
<220> FEATURE:
<223> OTHER INFORMATION: oligonucleotide

<400> SEQUENCE: 14
gcatctgcag ttatttgaga cgtttgcaca aggtg                               35

<210> SEQ ID NO 15
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (18)..(18)
<223> OTHER INFORMATION: N = A or G or C or T
<220> FEATURE:
<221> NAME/KEY: misc_feature
<222> LOCATION: (24)..(24)
<223> OTHER INFORMATION: N = A or G or C or T

<400> SEQUENCE: 15
accatcgaga tcggcgtntt ycangg                                         26

<210> SEQ ID NO 16
<211> LENGTH: 27
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (19)..(19)
<223> OTHER INFORMATION: Y = C or T
<220> FEATURE:
<221> NAME/KEY: misc_feature
<222> LOCATION: (22)..(22)
<223> OTHER INFORMATION: N = A or G or C or T
<220> FEATURE:
<221> NAME/KEY: misc_feature
```

```
<222> LOCATION: (25)..(25)
<223> OTHER INFORMATION: Y = C or T

<400> SEQUENCE: 16
cgacttcgcc ttcgtggayg cngayaa                                          27

<210> SEQ ID NO 17
<211> LENGTH: 31
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (23)..(23)
<223> OTHER INFORMATION: N = A or G or C or T
<220> FEATURE:
<221> NAME/KEY: misc_feature
<222> LOCATION: (26)..(26)
<223> OTHER INFORMATION: N = A or G or C or T
<220> FEATURE:
<221> NAME/KEY: misc_feature
<222> LOCATION: (29)..(29)
<223> OTHER INFORMATION: Y = C or T

<400> SEQUENCE: 17
tgaagttgat cttgtgctcc acnccngcyt t                                     31

<210> SEQ ID NO 18
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (17)..(18)
<223> OTHER INFORMATION: N = A or G or C or T
<220> FEATURE:
<221> NAME/KEY: misc_feature
<222> LOCATION: (21)..(21)
<223> OTHER INFORMATION: R = A or G
<220> FEATURE:
<221> NAME/KEY: misc_feature
<222> LOCATION: (24)..(24)
<223> OTHER INFORMATION: N = A o rG or C or T

<400> SEQUENCE: 18
cgccggcaga aggtganncc rtcncc                                           26

<210> SEQ ID NO 19
<211> LENGTH: 45
<212> TYPE: DNA
<213> ORGANISM: Artificial Sequence
<220> FEATURE:
<223> OTHER INFORMATION: oligonucleotide

<400> SEQUENCE: 19
ctgagagaac tagtctcgag ctctagaaca agcttttttt ttttt                      45

<210> SEQ ID NO 20
<211> LENGTH: 36
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (24)..(25)
<223> OTHER INFORMATION: n = deoxyinosine
<220> FEATURE:
```

<220> FEATURE:
<221> NAME/KEY: misc_feature
<222> LOCATION: (29)..(30)
<223> OTHER INFORMATION: n = deoxyinosine
<220> FEATURE:
<221> NAME/KEY: misc_feature
<222> LOCATION: (34)..(35)
<223> OTHER INFORMATION: n = deoxyinosine

<400> SEQUENCE: 20
ggccacgcgt cgactagtac gggnngggnn gggnng          36

<210> SEQ ID NO 21
<211> LENGTH: 780
<212> TYPE: DNA
<213> ORGANISM: Fuchsia

<400> SEQUENCE: 21
accatcgaga tcggcgtctt cactggctat tctcttcttt gcactgcact tgctttgcct      60
cccgatggca agataacagc gatcgacccc gacaaagaag cttacgagac cgggctgcca     120
tttattcaga agctggagt gggacataag atcaacttca tcaatggtga cgcacttgca     180
gtactcgacg atcttattgc agacggaaaa gatcaagagg ggagttttga ttttgcgttc    240
gtggatgcta acaaggaaga ttacatcaag taccacgaac agctgcttaa acttgtcaag    300
gtaggtggct tgatctgcta cgacaacacc ctgtggttcg gtcggtggc gctcccgaa     360
gaagatccca tggacgagtt tatgagaagc ggcagggtcc cgcttaggaa gttgaacgac    420
ttcctcgcaa atgaccccg tatcgagtca tgccttgttt ccatcggtga tggcctcacc    480
ctctgccgcc gccgcctcta atgcatctcg agagagttac tggcccctag ctagctagct    540
agctcgttgt tgttatatat atattatccg attgatatgt ggattctcac catatgtacg    600
tggattctgc gtactatcca gtggcgcctt tgttgcatc tatctatatt tctagtttat    660
tatatgtacc atattcgctt ccgatatgtg cgaataagtc ggatgccatg cttccgatgg    720
ggtatcgttc ttattttcaa tcgttagtga tttttaagtt gagcaaaaaa aaaaaaaaaa    780

<210> SEQ ID NO 22
<211> LENGTH: 166
<212> TYPE: PRT
<213> ORGANISM: Fuchsia

<400> SEQUENCE: 22

Thr Ile Glu Ile Gly Val Phe Thr Gly Tyr Ser Leu Leu Cys Thr Ala
1               5                   10                  15

Leu Ala Leu Pro Pro Asp Gly Lys Ile Thr Ala Ile Asp Pro Asp Lys
            20                  25                  30

Glu Ala Tyr Glu Thr Gly Leu Pro Phe Ile Gln Lys Ala Gly Val Gly
        35                  40                  45

His Lys Ile Asn Phe Ile Asn Gly Asp Ala Leu Ala Val Leu Asp Asp
    50                  55                  60

Leu Ile Ala Asp Gly Lys Asp Gln Glu Gly Ser Phe Asp Phe Ala Phe
65                  70                  75                  80

Val Asp Ala Asn Lys Glu Asp Tyr Ile Lys Tyr His Glu Gln Leu Leu
                85                  90                  95

Lys Leu Val Lys Val Gly Gly Leu Ile Cys Tyr Asp Asn Thr Leu Trp
            100                 105                 110

Phe Gly Ser Val Ala Leu Ser Glu Glu Asp Pro Met Asp Glu Phe Met
        115                 120                 125

Arg Ser Gly Arg Val Pro Leu Arg Lys Leu Asn Asp Phe Leu Ala Asn

```
            130                 135                 140
Asp Pro Arg Ile Glu Ser Cys Leu Val Ser Ile Gly Asp Gly Leu Thr
145                 150                 155                 160

Leu Cys Arg Arg Arg Leu
            165

<210> SEQ ID NO 23
<211> LENGTH: 27
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (17)..(17)
<223> OTHER INFORMATION: Y = C or T
<220> FEATURE:
<221> NAME/KEY: misc_feature
<222> LOCATION: (19)..(19)
<223> OTHER INFORMATION: N = A or G or C or T
<220> FEATURE:
<221> NAME/KEY: misc_feature
<222> LOCATION: (22)..(22)
<223> OTHER INFORMATION: R = A or G
<220> FEATURE:
<221> NAME/KEY: misc_feature
<222> LOCATION: (25)..(25)
<223> OTHER INFORMATION: R = A or G
<220> FEATURE:
<221> NAME/KEY: misc_feature
<222> LOCATION: (26)..(26)
<223> OTHER INFORMATION: Y = C or T

<400> SEQUENCE: 23
ccgggagcac gagcacytna argaryt                                        27

<210> SEQ ID NO 24
<211> LENGTH: 28
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (18)..(18)
<223> OTHER INFORMATION: R = A or G
<220> FEATURE:
<221> NAME/KEY: misc_feature
<222> LOCATION: (21)..(21)
<223> OTHER INFORMATION: R = A or G
<220> FEATURE:
<221> NAME/KEY: misc_feature
<222> LOCATION: (24)..(24)
<223> OTHER INFORMATION: N = A or G or C or T
<220> FEATURE:
<221> NAME/KEY: misc_feature
<222> LOCATION: (27)..(27)
<223> OTHER INFORMATION: N = A or G or C or T

<400> SEQUENCE: 24
ggcctgccct tcatccaraa rgcnggng                                       28

<210> SEQ ID NO 25
<211> LENGTH: 34
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (26)..(26)
<223> OTHER INFORMATION: R = A or G
```

<220> FEATURE:
<221> NAME/KEY: misc_feature
<222> LOCATION: (32)..(32)
<223> OTHER INFORMATION: R = A or G
<220> FEATURE:
<221> NAME/KEY: misc_feature
<222> LOCATION: (29)..(29)
<223> OTHER INFORMATION: N = A or G or C or T

<400> SEQUENCE: 25
cgtggtagtt cacgtagttg ctcttrtcng crtc                                34

<210> SEQ ID NO 26
<211> LENGTH: 1079
<212> TYPE: DNA
<213> ORGANISM: Petunia

<400> SEQUENCE: 26
attttctgga caagttcgat tacctttgaa tctccaagga ctttactgaa tcaatggcag     60
gcaaaagcgg acatggctcc attcttcaaa gtgaagccct caagaagtac atcttcgaaa    120
ctagtgtgta tccaagagaa cacgagcaac tcaaagaact cacacaagcc tcattcgata    180
agtataaaat agtgagcttg atgggtgtgc ctccagatga agcccaattt ctctcgatgc    240
tcttaaaaat aatgaatgca agaagacaa tggagattgg agttttttacc ggttattctc    300 ttctggctac tgctcttgca ttgccagaag atggaaaaat tatagcgatt gatccggaca    360
gagaagcata tgaggttgga ttgccatata ttcagaaggc tggtgtggag cataagattg    420
aatttattca atcagaagcc ttaccagtac tcgaaaaact cctctctaac ggtgaggaag    480
aaggaacatt tgatttcata ttcattgatg ctgataagga gaactatctg aagtaccatg    540
agatagtact aaaattggtg aaagtgggag gagtgatagg ctatgacaac acattatggt    600
ttgggaccgt ggcactttca gatgatgatc ctataccaca aggcttaaga gaattgagga    660
gatcggtttt gaagatcaac agtttttttag ctactgatcc tcgcattgaa ttagctcatc    720
tttcaattgg tgatggtctt acccttggca ggcgtctcag ctagtttatt tttcgtataa    780
tcatctgaat tccggaatcc attatcttta tagttttttg ttttttcagta ctagtgatat    840 ttttcagtcc ccacttatgg ataacactgg gtaatgagta ttgttgcaga agtagtgaca    900
tttttaagtt tggttcgtcc atctgctaaa gaagtcacga tttcgtcttg tagacgagct    960
atagtatgca tttgcatttt ggttaatttc gcatgtagtg ttgaaatgtg aattaccaaa   1020
agcaaaagta ataaaatgtt tacatttgtt gtgttttaaa aaaaaaaaa aaaaaaaa     1079

<210> SEQ ID NO 27
<211> LENGTH: 20
<212> TYPE: DNA
<213> ORGANISM: Artificial Sequence
<220> FEATURE:
<223> OTHER INFORMATION: oligonucleotide

<400> SEQUENCE: 27
ctgagagaac tagtctcgag                                               20

<210> SEQ ID NO 28
<211> LENGTH: 28
<212> TYPE: DNA
<213> ORGANISM: Artificial Sequence
<220> FEATURE:
<223> OTHER INFORMATION: oligonucleotide

<400> SEQUENCE: 28

-continued

```
ccctcgagtt tctattttgt gtgtgttg                                    28

<210> SEQ ID NO 29
<211> LENGTH: 26
<212> TYPE: DNA
<213> ORGANISM: Artificial Sequence
<220> FEATURE:
<223> OTHER INFORMATION: oligonucleotide

<400> SEQUENCE: 29
gggaattcta gagctcgagg atcacg                                      26

<210> SEQ ID NO 30
<211> LENGTH: 24
<212> TYPE: DNA
<213> ORGANISM: Artificial Sequence
<220> FEATURE:
<223> OTHER INFORMATION: oligonucleotide

<400> SEQUENCE: 30
actaccaagg atcctactga agca                                        24

<210> SEQ ID NO 31
<211> LENGTH: 20
<212> TYPE: DNA
<213> ORGANISM: Artificial Sequence
<220> FEATURE:
<223> OTHER INFORMATION: oligonucleotide

<400> SEQUENCE: 31
ctcgaatgaa gcttttgtta                                             20

<210> SEQ ID NO 32
<211> LENGTH: 24
<212> TYPE: DNA
<213> ORGANISM: Artificial Sequence
<220> FEATURE:
<223> OTHER INFORMATION: oligonucleotide

<400> SEQUENCE: 32
cataaatagg atccgcagca gcaa                                        24

<210> SEQ ID NO 33
<211> LENGTH: 20
<212> TYPE: DNA
<213> ORGANISM: Artificial Sequence
<220> FEATURE:
<223> OTHER INFORMATION: oligonucleotide

<400> SEQUENCE: 33
agtctcataa gcttctctat                                             20

<210> SEQ ID NO 34
<211> LENGTH: 22
<212> TYPE: DNA
<213> ORGANISM: Artificial Sequence
<220> FEATURE:
<223> OTHER INFORMATION: oligonucleotide

<400> SEQUENCE: 34
gcaagtgcag tgcaaagaag ag                                          22

<210> SEQ ID NO 35
<211> LENGTH: 20
<212> TYPE: DNA
<213> ORGANISM: Artificial Sequence
```

```
<220> FEATURE:
<223> OTHER INFORMATION: oligonucleotide

<400> SEQUENCE: 35
gatcttatgt tccactccgc                                                    20

<210> SEQ ID NO 36
<211> LENGTH: 20
<212> TYPE: DNA
<213> ORGANISM: Artificial Sequence
<220> FEATURE:
<223> OTHER INFORMATION: oligonucleotide

<400> SEQUENCE: 36
gagagatctg accagtaagg                                                    20

<210> SEQ ID NO 37
<211> LENGTH: 24
<212> TYPE: DNA
<213> ORGANISM: Artificial Sequence
<220> FEATURE:
<223> OTHER INFORMATION: oligonucleotide

<400> SEQUENCE: 37
ggatattttt cggccgtgac ctcc                                               24

<210> SEQ ID NO 38
<211> LENGTH: 24
<212> TYPE: DNA
<213> ORGANISM: Artificial Sequence
<220> FEATURE:
<223> OTHER INFORMATION: oligonucleotide

<400> SEQUENCE: 38
atcttagaga cgactgctta tccc                                               24

<210> SEQ ID NO 39
<211> LENGTH: 68
<212> TYPE: DNA
<213> ORGANISM: Artificial Sequence
<220> FEATURE:
<223> OTHER INFORMATION: oligonucleotide

<400> SEQUENCE: 39
aattcgcagc aaaaatgaaa gataagttct atggcaccat tttgcagagc gaagccctcg        60
caaagtat                                                                 68

<210> SEQ ID NO 40
<211> LENGTH: 63
<212> TYPE: DNA
<213> ORGANISM: Artificial Sequence
<220> FEATURE:
<223> OTHER INFORMATION: oligonucleotide

<400> SEQUENCE: 40
tactttgcga gggcttcgct ctgcaaaatg gtgccataga acttatcttt catttttgct        60
gcg                                                                      63

<210> SEQ ID NO 41
<211> LENGTH: 841
<212> TYPE: DNA
<213> ORGANISM: Fuchsia

<400> SEQUENCE: 41
```

```
atcttagaga cgactgctta tcccggagaa aatgagcatc tgaagcaact ccgggaggtc    60
acggccgaaa aatatcctta ctggagcatg atgaatgtgt caattgacga gggacaactt   120
atatcgctaa tattgaagct catgaacgcg agaaagacat tagagatcgg cgtcttcact   180
ggctattctc ttctttgcac tgcacttgct ttgcctcccg atggcaagat aacagcgatc   240
gaccccgaca agaagcttta cgagaccggg ctgccattta ttcagaaagc tggagtggaa   300
cataagatca acttcatcaa tggtgacgca cttgcagtac tcgacgatct tattgcagac   360
ggaaaagatc aagaggggag ttttgatttt gcgttcgtgg atgctaacaa ggaagattac   420
atcaagtacc acgaacagct gcttaaactg gtcaaggtag gtggcttgat ctgctacgac   480
aacaccctgt ggttcgggtc ggtggcgctc tccgaagaag atcccatgga tgagtttatg   540
aggagcggca gggtcccaat taggaagttg aacgacttcc tcgcaaatga ccccgtatc    600
gagtcatgcc ttgtttccat cggtgatggc atcaccctct gccgccgccg cctctaatgc   660
atctcgagag agttactggc ccctagctag ctagctcgtt gttgttatat atatatatta   720
tccgattgat atgtggattc tcaccatatg tacgtggatt ctgtgtacta ccagtggcg    780
ccttttgttg catctatcta tatttctagt ttattttatg taccaaaaaa aaaaaaaaa    840
a                                                                   841
```

<210> SEQ ID NO 42
<211> LENGTH: 218
<212> TYPE: PRT
<213> ORGANISM: Fuchsia

<400> SEQUENCE: 42

```
Ile Leu Glu Thr Thr Ala Tyr Pro Gly Glu Asn Glu His Leu Lys Gln
1               5                   10                  15

Leu Arg Glu Val Thr Ala Glu Lys Tyr Pro Tyr Trp Ser Met Met Asn
            20                  25                  30

Val Ser Ile Asp Glu Gly Gln Leu Ile Ser Leu Ile Leu Lys Leu Met
        35                  40                  45

Asn Ala Arg Lys Thr Leu Glu Ile Gly Val Phe Thr Gly Tyr Ser Leu
    50                  55                  60

Leu Cys Thr Ala Leu Ala Leu Pro Pro Asp Gly Lys Ile Thr Ala Ile
65                  70                  75                  80

Asp Pro Asp Lys Glu Ala Tyr Glu Thr Gly Leu Pro Phe Ile Gln Lys
                85                  90                  95

Ala Gly Val Glu His Lys Ile Asn Phe Ile Asn Gly Asp Ala Leu Ala
            100                 105                 110

Val Leu Asp Asp Leu Ile Ala Asp Gly Lys Asp Gln Glu Gly Ser Phe
        115                 120                 125

Asp Phe Ala Phe Val Asp Ala Asn Lys Glu Asp Tyr Ile Lys Tyr His
    130                 135                 140

Glu Gln Leu Leu Lys Leu Val Lys Val Gly Gly Leu Ile Cys Tyr Asp
145                 150                 155                 160

Asn Thr Leu Trp Phe Gly Ser Val Ala Leu Ser Glu Glu Asp Pro Met
                165                 170                 175

Asp Glu Phe Met Arg Ser Gly Arg Val Pro Ile Arg Lys Leu Asn Asp
            180                 185                 190

Phe Leu Ala Asn Asp Pro Arg Ile Glu Ser Cys Leu Val Ser Ile Gly
        195                 200                 205

Asp Gly Ile Thr Leu Cys Arg Arg Arg Leu
    210                 215
```

<210> SEQ ID NO 43
<211> LENGTH: 943
<212> TYPE: DNA
<213> ORGANISM: Fuchsia

<400> SEQUENCE: 43

```
aattcgcagc aaaaatgaaa gataagttct atggcaccat tttgcagagc gaagccctcg      60
caaagtatat cttagagacg accgcttatc ccggagaaaa tgagcatctg aagcaactcc     120
gggaggtcac ggccgaaaaa tatccttact ggagcatgat gaatgtgtca attgacgagg     180
gacaacttat atcgctaata ttgaagctca tgaacgcgag aaagacatta gagatcggcg     240
tcttcactgg ctattctctt ctttgcactg cacttgcttt gcctcccgat ggcaagataa     300
cagcgatcga ccccgacaaa gaagcttacg agaccgggct gccatttatt cagaaagctg     360
gagtggaaca taagatcaac ttcatcaatg gtgacgcact tgcagtactc gacgatctta     420
ttgcagacgg aaaagatcaa gaggggagtt ttgattttgc gttcgtggat gctaacaagg     480
aagattacat caagtaccac gaacagctgc ttaaactggt caaggtaggt ggcttgatct     540
gctacgacaa caccctgtgg ttcgggtcgg tggcgctctc cgaagaagat cccatggatg     600
agtttatgag gagcggcagg gtcccaatta ggaagttgaa cgacttcctc gcaaatgacc     660
cccgtatcga gtcatgcctt gtttccatcg gtgatggcat caccctctgc cgccgccgcc     720
tctaatgcat ctcgagagag ttactggccc ctagctagct agctcgttgt tgttatatat     780
atatattatc cgattgatat gtggattctc accatatgta cgtggattct gtgtactatc     840
cagtggcgcc ttttgttgca tctatctata tttctagttt attttatgta ccaaaaaaaa     900
aaaaaaaaag cttgttctac agctcgagac tagttctctc aaa                       943
```

<210> SEQ ID NO 44
<211> LENGTH: 236
<212> TYPE: PRT
<213> ORGANISM: Fuchsia

<400> SEQUENCE: 44

```
Met Lys Asp Lys Phe Tyr Gly Thr Ile Leu Gln Ser Glu Ala Leu Ala
1               5                   10                  15
Lys Tyr Ile Leu Glu Thr Thr Ala Tyr Pro Gly Glu Asn Glu His Leu
            20                  25                  30
Lys Gln Leu Arg Glu Val Thr Ala Glu Lys Tyr Pro Tyr Trp Ser Met
        35                  40                  45
Met Asn Val Ser Ile Asp Glu Gly Gln Leu Ile Ser Leu Ile Leu Lys
    50                  55                  60
Leu Met Asn Ala Arg Lys Thr Leu Glu Ile Gly Val Phe Thr Gly Tyr
65                  70                  75                  80
Ser Leu Leu Cys Thr Ala Leu Ala Leu Pro Pro Asp Gly Lys Ile Thr
                85                  90                  95
Ala Ile Asp Pro Asp Lys Glu Ala Tyr Glu Thr Gly Leu Pro Phe Ile
            100                 105                 110
Gln Lys Ala Gly Val Glu His Lys Ile Asn Phe Ile Asn Gly Asp Ala
        115                 120                 125
Leu Ala Val Leu Asp Asp Leu Ile Ala Asp Gly Lys Asp Gln Glu Gly
    130                 135                 140
Ser Phe Asp Phe Ala Phe Val Asp Ala Asn Lys Glu Asp Tyr Ile Lys
145                 150                 155                 160
```

```
Tyr His Glu Gln Leu Leu Lys Leu Val Lys Val Gly Leu Ile Cys
                165                 170                 175

Tyr Asp Asn Thr Leu Trp Phe Gly Ser Val Ala Leu Ser Glu Glu Asp
            180                 185                 190

Pro Met Asp Glu Phe Met Arg Ser Gly Arg Val Pro Ile Arg Lys Leu
        195                 200                 205

Asn Asp Phe Leu Ala Asn Asp Pro Arg Ile Glu Ser Cys Leu Val Ser
    210                 215                 220

Ile Gly Asp Gly Ile Thr Leu Cys Arg Arg Arg Leu
225                 230                 235

<210> SEQ ID NO 45
<211> LENGTH: 8
<212> TYPE: DNA
<213> ORGANISM: Artificial Sequence
<220> FEATURE:
<223> OTHER INFORMATION: oligonucleotide

<400> SEQUENCE: 45 gggatccc                                                              8

<210> SEQ ID NO 46
<211> LENGTH: 8
<212> TYPE: DNA
<213> ORGANISM: Artificial Sequence
<220> FEATURE:
<223> OTHER INFORMATION: oligonucleotide

<400> SEQUENCE: 46 ggcgcgcc                                                              8

<210> SEQ ID NO 47
<211> LENGTH: 8
<212> TYPE: DNA
<213> ORGANISM: Artificial Sequence
<220> FEATURE:
<223> OTHER INFORMATION: oligonucleotide

<400> SEQUENCE: 47 ggtcgacc                                                              8

<210> SEQ ID NO 48
<211> LENGTH: 8
<212> TYPE: PRT
<213> ORGANISM: Artificial Sequence
<220> FEATURE:
<223> OTHER INFORMATION: Synthetic peptide

<400> SEQUENCE: 48

Met Thr Gly Lys Thr Ala His Pro
1               5

<210> SEQ ID NO 49
<211> LENGTH: 19
<212> TYPE: PRT
<213> ORGANISM: Artificial Sequence
<220> FEATURE:
<223> OTHER INFORMATION: Synthetic peptide

<400> SEQUENCE: 49

Met Arg Gly Ser His His His His His His Gly Ser Thr Gly Lys Thr
1               5                   10                  15

Ala His Pro
```

```
<210> SEQ ID NO 50
<211> LENGTH: 8
<212> TYPE: PRT
<213> ORGANISM: Artificial Sequence
<220> FEATURE:
<223> OTHER INFORMATION: Synthetic peptide

<400> SEQUENCE: 50

Met Lys Asp Lys Phe Tyr Gly Thr
1               5

<210> SEQ ID NO 51
<211> LENGTH: 19
<212> TYPE: PRT
<213> ORGANISM: Artificial Sequence
<220> FEATURE:
<223> OTHER INFORMATION: Synthetic peptide

<400> SEQUENCE: 51

Met Arg Gly Ser His His His His His His Gly Ser Lys Asp Lys Phe
1               5                   10                  15

Tyr Gly Thr
```